United States Patent
Reiner et al.

(10) Patent No.: US 10,500,180 B2
(45) Date of Patent: *Dec. 10, 2019

(54) MODIFIED RELEASE ORALLY ADMINISTERED AMINO ACID FORMULATIONS

(71) Applicant: APR APPLIED PHARMA RESEARCH S.A., Balerna (CH)

(72) Inventors: Alberto Reiner, Como (IT); Giorgio Reiner, Como (IT)

(73) Assignee: APR Applied Pharma Research S.A., Balerna (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/938,837

(22) Filed: Mar. 28, 2018

(65) Prior Publication Data
US 2018/0318244 A1 Nov. 8, 2018

Related U.S. Application Data

(63) Continuation of application No. PCT/IB2016/055773, filed on Sep. 27, 2016.

(60) Provisional application No. 62/233,695, filed on Sep. 28, 2015.

(51) Int. Cl.

| | |
|---|---|
| *A61K 31/198* | (2006.01) |
| *A61K 9/00* | (2006.01) |
| *A61K 9/16* | (2006.01) |
| *A61K 9/50* | (2006.01) |
| *A61K 31/401* | (2006.01) |
| *A61K 31/405* | (2006.01) |
| *A61K 31/4172* | (2006.01) |
| *A23L 33/175* | (2016.01) |
| *A21D 13/80* | (2017.01) |
| *A61P 3/00* | (2006.01) |
| *A61K 9/51* | (2006.01) |
| *A61K 31/00* | (2006.01) |
| *A61K 33/00* | (2006.01) |
| *A61K 9/20* | (2006.01) |
| *A23L 33/15* | (2016.01) |
| *A23L 33/16* | (2016.01) |
| *A21D 2/24* | (2006.01) |

(52) U.S. Cl.
CPC ............ *A61K 31/198* (2013.01); *A21D 2/245* (2013.01); *A21D 13/80* (2017.01); *A23L 33/15* (2016.08); *A23L 33/16* (2016.08); *A23L 33/175* (2016.08); *A61K 9/0053* (2013.01); *A61K 9/0056* (2013.01); *A61K 9/1635* (2013.01); *A61K 9/1652* (2013.01); *A61K 9/205* (2013.01); *A61K 9/5015* (2013.01); *A61K 9/5047* (2013.01); *A61K 9/5073* (2013.01); *A61K 9/5115* (2013.01); *A61K 9/5123* (2013.01); *A61K 9/5138* (2013.01); *A61K 9/5161* (2013.01); *A61K 31/00* (2013.01); *A61K 31/401* (2013.01); *A61K 31/405* (2013.01); *A61K 31/4172* (2013.01); *A61K 33/00* (2013.01); *A61P 3/00* (2018.01); *A23V 2002/00* (2013.01); *A61K 2300/00* (2013.01)

(58) Field of Classification Search
None
See application file for complete search history.

(56) References Cited

FOREIGN PATENT DOCUMENTS

| | | |
|---|---|---|
| EP | 1774858 A1 | 4/2007 |
| GB | 1217365 A | 12/1970 |
| WO | 2000/67797 A1 | 11/2000 |
| WO | 2011/043647 A1 | 4/2011 |
| WO | 2016/112170 A1 | 7/2016 |

OTHER PUBLICATIONS

Amidon G.L. Lennernäs H. Shah V.P. Crison J.R. A theoretical basis for a biopharmaceutical drug classification: the correlation of in vitro drug product dissolution and in vivo bioavailability. Pharm. Res. 12:414-420 (1995).
Baracos V.E. Animal models of amino acids metabolism: a focus on the intestine. J. Nutria. 134:1656S-1659S (2004).
Brosnan JT. Brosnan ME. Branched-chain amino acids: enzyme and substrate regulation. J Nutr. Jan. 2006;136(1 Suppl):207S-11S.
Cynober LA. Plasma amino acid levels with a note on membrane transport: characteristics. regulation. and metabolic significance. Nutrition. Sep. 2002;18(9):761-6.
Dioguardi F.S. Clinical use of amino acids as dietary supplement: pros and cons. J. Cochexia Sarcopenia Muscle. 2:75-80 (2011).
Public Summary Document—Nov. 2015 PBAC Meeting; Amino Acid Formula Without Phenylalanine, 110g modified release tablet x 4, bottle, PKU Easy Microtabs®, Orphamia Pty Ltd.
Giovannini M. Riva E. Salvatici E. Cefalo G. Radaelli G. Randomized controlled trial of a protein substitute with prolonged release on the protein statatus of children with phenylketonuria. J. Am. Coll. Nutr. 33. 103-110 (2014).
Gropper S.S. Acosta P.B. Effect of simultaneous ingestion of L-amino acids and whole protein on plasma amino acid and urea nitrogen concentrations in humans. J. Parenteral Enteral Nutr. 15:48-53 (1991).
Keohane P. P. Grimble G. K. Brown B. Spiller R. C. Influence of protein composition and hydrolysis method on intestinal absorption of protein in man. Gut. 26:907-913 (1985).
Cole, Jeffery T. Metabolism of BCAAs. R. Rajendram et al. (eds.), Branched Chain Amino Acids in Clinical Nutrition: 13 vol. 1, Nutrition and Health, DOI 10.10071978-1-4939-1923-9_2.
Ney D.M. Blank R.D. Hansen K.E. Advances in the nutritional and pharmacological management of phenylketonuria. Co-Clinical Nutrition. Com. 17:61-68 (2014).
Ney DM. Does the PKU diet contribute to impaired renal function? J Inherit Metab Dis. Sep. 2013;36(5):903-4.

(Continued)

*Primary Examiner* — Brian J Davis
(74) *Attorney, Agent, or Firm* — Clark Sullivan

(57) ABSTRACT

Methods and formulations of modified release amino acids are provided for the treatment or management of diseases defined by impaired amino acid metabolism, with improved pharmacokinetics, metabolism and utilization.

21 Claims, 21 Drawing Sheets
(17 of 21 Drawing Sheet(s) Filed in Color)

(56) References Cited

OTHER PUBLICATIONS

Pena MJ. Rocha JC and Borges N. Amino Acids. Glucose Metabolism and Clinical Relevance for Phenylketonuria Management. Ann Nutr Disord & Ther—vol. 2 Issue 3—2015.
Van Spronsen FJ. De Groot MJ. Hoeksma M. Reijngoud DJ. Van Rijn M. Large neutral amino acids in the treatment of PKU: from theory to practice. J Inherit Metab Dis. Dec. 2010;33(6):671-6.
Vliet D. Van. Derks T.G.J. Rijn M. Van. De Groot M.J. McDonald A. et al. Single amino acid supplementation in aminoacidopatients: a systemic review. Orphanet J. Rare Dis. 9:1-14 (2014).
Waisbren S. E. Noel K. Fahrdach K. Cella C. Frame D. Dorenbaum A. Levy H. Phenylalanine blood levels and clinical outcomes in phenylketonuria: a systemic literature review and meta-analysis. Mol. Genet. Metab. 92:63-70 (2007).
Whang K.Y. and Easter R.A. Asian-Aus. J. Anim. Sci. 2000 vol. 13. No. 6:811-816.
MacDonald, Anita; The Dietary Management of Phenylketonuria; Thesis; Department of Reproductive and Child Health School of Medicine; University of Birmingham, Aug. 1999.
International Search Report and Written Opinion issued in corresponding International Application No. PCT/IB2016/055773 dated Dec. 21, 2016.
Anonymous: "Afenil Micro 3H", Internet citation, 2014, XP002765113, Retrieved from the Inernet: URL: http://www.piamfarmaceutici.com/Internet/medifood/Prodotti.aspx?P=100&C=12 (Translation of Abstract).

FIGURE 1
Prior Art

Classification of amino acids present in proteins

| | general structure of amino acids | 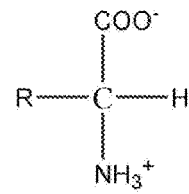 | | |
|---|---|---|---|---|
| Name | Abbreviation R- | $pK_a$ values | | |
| Aliphatic amino acids | | -COO⁻ | -NH₃⁺ | Others |
| Glycine | Gly  H— | 2.34 | 9.60 | - |
| Alanine | Ala  CH₃— | 2.35 | 9.69 | - |
| Valine | Val  H₃C—CH— / CH₃ | 2.32 | 9.62 | - |
| Leucine | Leu  H₃C—CH—CH₂— / CH₃ | 2.36 | 9.60 | - |
| Isoleucine | Ile  H₃C—CH₂—CH— / CH₃ | 2.36 | 9.68 | - |
| Serine | Ser  HO—CH₂— | 2.21 | 9.15 | - |
| Threonine | Thr  HO—CH— / CH₃ | 2.09 | 9.10 | - |
| Aromatic amino acids | | | | |
| Phenylalanine | Phe | 1.83 | 9.13 | - |
| Tyrosine | Tyr | 2.20 | 9.11 | 10.07 |
| Tryptophan | Trp | 2.38 | 9.38 | - |

FIGURE 1 (continued)

| Acid amino acids | | | | | |
|---|---|---|---|---|---|
| Aspartic acid | Asp | —CH₂—COO⁻ | 2.01 | 9.93 | 3.80 |
| Asparagine | Asn | —CH₂—C(=O)—NH₂ | 2.02 | 8.80 | - |
| Glutamic acid | Glu | —CH₂—CH₂—COO⁻ | 2.13 | 9.76 | 4.31 |
| Glutamine | Gln | —CH₂—CH₂—C(=O)—NH₂ | 2.17 | 9.13 | |
| Basic amino acids | | | | | |
| Lysine | Lys | H₂C—CH₂—CH₂—CH₂— / NH₃⁺ | 2.18 | 8.95 | 10.53 |
| Arginine | Arg | ⁺H₃N—C(=NH)—NH—CH₂—CH₂—CH₂— | 2.17 | 9.04 | 12.48 |
| Histidine | His | (imidazole)—CH₂— | 1.82 | 9.17 | 6.0 |
| Sulphurated amino acids | | | | | |
| Cysteine | Cys | HS—CH₂— | 1.91 | 10.36 | 8.24 |
| Methionine | Met | H₃C—S—CH₂—CH₂— | 2.28 | 9.21 | |
| Imino acids | | | | | |
| Proline | Pro | (pyrrolidine)—COO⁻ | 1.95 | 10.64 | |
| Other amino acids | | | | | |
| Hydroxylysine | | H₂C—CH(OH)—CH—CH₂— / NH₃⁺ | 2.13 | 8.62 | 9.67 |
| Cystine | | H₂C—S—S—CH₂ | 1.04 | 8.02 | |
| | | | 2.1 | 8.71 | |

| Hydroxyproline |  | 1.92 | 9.73 |

Essential amino acids for humans

| Amino acids | |
|---|---|
| Arginine  | Essential amino acids only for infants |
| Histidine | |
| Isoleucine  | |
| Leucine | |
| Threonine | |
| Lysine | Essential amino acids for adults |
| Methionine | |
| Phenylalanine | |
| Tryptophan | |
| Valine | |

Dissolution Test PKU
TPP coated without Mannitol 630μ
pH 1.2

MODIFIED RELEASE ORALLY ADMINISTERED AMINO ACID FORMULATIONS

FIELD OF THE INVENTION

This invention pertains to orally administered formulations and dosage forms of amino acids with improved dosing accuracy, improved palatability, and improved pharmacokinetics for optimum therapeutic effect.

BACKGROUND

Amino acids are necessary building blocks in the synthesis of proteins by the human body, derived principally from dietary sources of proteins. The human body uses nineteen separate L-configuration amino acids to synthesize proteins. Some of these amino acids are referred to as "essential amino acids" because the body cannot independently synthesize them. Other amino acids are not "essential" because the body can synthesize them.

The digestion of dietary proteins to amino acids starts in the stomach, thanks to the combined activity of pepsinogen, pepsine and hydrochloric acid leading to oligopeptides. The digestion continues in the duodenum after transit from the stomach through the pylorus, where the combined activity of biliary secretion, bicarbonates and pancreatic enzymes is able to produce individual amino acids. Montgomery R. et al., 1988; Baracos, 2004. The liberated amino acids are then absorbed from the small intestine into the portal vein according to active stereospecific transport processes specific for amino acids. The secretion into the intestine of amino acids is a concomitant mechanism. Dipeptides and tripeptides can also be absorbed from the small intestine, but they too are eventually hydrolyzed into amino acids in the enterocyte. These processes are largely pH dependent. When food is ingested, the stomach secretes hydrochloric acid and the pH decreases to around 2. After the pyloric valve, the pH progressively increases from 4 to approximately 7 as a consequence of alkaline biliary secretion. A buffer system operates to prevent pH values larger than approximately 7.5-7.8.

The time required to digest dietary proteins is the sum of the time spent in the gastric emptying phase and the time required for hydrolysis in the small intestine. The time needed for both of these processes can vary depending on food intake, protein intake, illness, and concomitant drug treatments, with food intake being the most common determining factor. Amidon et al., 1995 reports a gastric emptying time of approximately 3.5 hours after a high fat meal, approximately 1.5 hours after an average meal, and approximately 10 to 20 minutes after 250 ml of water. Keohane et al., 1985 reports the time required to hydrolyze amino acids in the small intestine, on average, is approximately three hours, and that this time varies for individual proteins and amino acids. This hydrolysis starts to occur immediately after gastric emptying, after transit through the pyloric valve, and lasts for several hours in the first tract of the small intestine, namely the jejunum.

Amino acids are commonly administered as supplements to the diet to facilitate protein synthesis, particularly where increases in muscle mass are intended. Specially formulated combinations of amino acids are also administered to support the nutritional health of individuals with special dietary intake limitations and requirements. In phenylketonuria, for example, the body is unable to metabolize phenylalanine to tyrosine due to the lack of necessary enzymes. The phenylalanine instead decomposes to several toxic by-products. Montgomery et al., 1988; Waisbren et al., 2007.

Phenylalanine is an essential amino acid that is normally metabolized to tyrosine by the enzyme phenylalanine hydroxylase. In phenylketonuria this enzyme is absent or not functioning properly, and the phenylalanine is decarboxylated to various compounds, three of them being toxic: phenylpyruvate, phenyl lactate and phenyl acetate. Because of this metabolic inhibition, the dietary intake of phenylalanine must be reduced while providing the amino acid tyrosine with the diet as it is indispensable. Ney D. M. et al., 2014; Dioguardi, 2011; Waisbren et al., 2007.

An effective management strategy for phenylketonuria consists of specially formulated amino acid formulations that omit phenylalanine while supplementing tyrosine. Because phenylalanine cannot be removed from most dietary sources of protein, these amino acid supplements will usually take the place of dietary proteins, which are eliminated from the diet entirely. Vliet Van D. et al., 2014. These patients can, however, also be treated with a carefully controlled diet of proteins that have very little phenylalanine. Gropper S. S. et al., 1991.

Examples of amino acid formulations sold for the management of phenylketonuria include formulations sold as Antifen™, Nutricia XP2™ (Maxamaid) and Milupa PKU2™ (Secunda). Nutricia XP2™ and Milupa PKU2™ also contain vitamins and minerals. The following Table A gives the formulations of these products, based on about 100 g of amino acids in each formulation, omitting the vitamin and mineral content.

TABLE A

| Component | Antifen ™ [1] g | Nutricia XP2 ™ [2] g | Milupa PKU2 ™ [3] g |
|---|---|---|---|
| Alanine | 7.60 | 4.05 | 4.03 |
| Arginine | 7.83 | 7.20 | 3.32 |
| Aspartic Acid | 11.30 | 6.70 | 9.48 |
| Cystine | 1.17 | 2.66 | 2.25 |
| Glutamic Acid | — | — | 19.92 |
| Glutamine | 12.50 | 4.94 | — |
| Glycine | 4.80 | 6.35 | 2.25 |
| Histidine | 2.73 | 4.11 | 2.25 |
| Isoleucine | 3.23 | 6.35 | 5.69 |
| Leucine | 7.20 | 10.86 | 9.37 |
| Lysine | 8.19 | 7.37 | 6.64 |
| Methionine | 2.14 | 1.73 | 2.25 |
| Proline | 4.89 | 7.70 | 9.01 |
| Serine | 8.10 | 4.66 | 4.98 |
| Taurine | 0.25 | 1.17 | — |
| Threonine | 3.80 | 5.33 | 4.51 |
| Tryptophan | 1.25 | 2.14 | 1.66 |
| Tyrosine | 7.50 | 9.64 | 5.57 |
| Valine | 5.40 | 6.97 | 6.64 |
| Carnitine | 0.11 | 0.06 | 0.18 |

[1] http://www.dmfmetabolic.it/wp-content/uploads/2013/10/AntifenIntegrale.pdf
[2] http://www.nutricia.it/prodotti/xp2-maxamaid/
[3] http://www.nutricia.it/prodotti/pku-2-secunda/

Other conditions for which specially formulated amino acid preparations are manufactured and administered, using the same strategy to provide all essential and non-essential amino acids but omitting amino acids that the body is unable to metabolize, include tyrosinemia, leucinosis, methylmalonic acidemia, homocistinuria, hyperglycinemia, isovaleric acidemia, propionic acidemia, and glutaric acidemia (types II, IIA or IIB).

Free amino acids potentially present numerous disadvantages over naturally occurring proteins, due to the rapid absorption of the amino acids, imposing a higher dietary acid load, particularly when higher doses are administered.

In addition the taste and the odor and taste of some commercial amino acid formulations is not good, which makes them extremely difficult for many people to ingest on a regular basis, particularly infants and children. In addition, these formulations are released immediately when ingested, leading to a very different absorption pattern than when proteins are ingested.

One object of the present invention is to limit the amino acid catabolism caused when free amino acids are ingested and overwhelm the body's metabolic capacity.

Another object of the present invention is to improve the taste of amino acid formulations when orally ingested.

Still another object of the present invention is to provide unique dosage forms of amino acids that can be eaten directly without the need for reconstitution.

Yet another object of the present invention is to provide formulations of amino acids with modified release properties, that more closely mimic the absorption pattern of proteins when orally ingested.

SUMMARY OF THE INVENTION

Modified release amino acid formulations have been developed that overcome the foregoing drawbacks. The formulations are more palatable and, most importantly, mimic the release profile of amino acids from naturally derived food sources. In particular, the formulations employ a release retarding mechanism that modifies the release of amino acids from the formulation to mimic the release rate of amino acids from naturally occurring proteins.

In the limited trials done to date, several individual amino acids and combinations of amino acids, when modified to achieve specific in vitro release criteria, have demonstrated statistically superior improvements in plasma concentrations of amino acids over comparable free amino acid formulations. Thus, in a first principal embodiment, the invention provides an orally administered amino acid formulation comprising one or more modified release amino acids, wherein the formulation comprising 2 g of the modified release amino acids releases no more than x % of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein x % is 90%, 80%, 70%, 60%, 50% or even 40%.

In an in vivo animal bioavailability study, it has unexpectedly been discovered that isoleucine, leucine, tyrosine, and valine, when modified for release as described herein, consistently have a maximum concentration in blood that is significantly less than the maximum concentration produced by a comparable free amino acid formulation. Thus, in a second principal embodiment the invention provides an orally administered amino acid formulation comprising a modified release amino acid selected from arginine, isoleucine, leucine, tyrosine and valine, wherein the formulation comprising 2 g of the modified release amino acids releases no more than x % of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein x % is 90%, 80%, 70%, 60%, 50%, or even 40%.

Another principal embodiment relates to a particular grouping of amino acids—the branched chain amino acids—and the unexpected discovery that the branched chain amino acids, in aggregate, when modified for release as described herein, produce a significantly lower $C_{max}$ and higher $C_{last}$ than the $C_{max}$ and $C_{last}$ produced by a comparable free amino acid formulation. Thus, in another principal embodiment the invention provides an orally administered amino acid formulation comprising one or more modified release branched chain amino acids, wherein the formulation comprising 2 g of the modified branched chain release amino acids releases no more than x % of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein x % is 90%, 80%, 70%, 60%, 50% or even 40%.

Yet another principal embodiment relates to another particular grouping of amino acids—essential amino acids—which, when modified for release as described herein, unexpectedly produce a significantly lower $C_{max}$ and significantly higher $C_{last}$ when compared to a comparable free amino acid formulation. Thus, in still another principal embodiment, the invention provides an orally administered amino acid formulation comprising one or more modified release essential amino acids, wherein the formulation comprising 2 g of the modified release essential amino acids releases no more than x % of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein x % is 90%, 80%, 70%, 60%, 50% or even 40%.

Still another principal embodiment relates to another grouping of amino acids—large neutral amino acids (excluding Phenylalanine, Tyrosine and Methionine)—which, when modified for release as described herein, unexpectedly produce a significantly lower $C_{max}$ and significantly higher $C_{last}$ when compared to a comparable free amino acid formulation. Thus, in still another principal embodiment, the invention provides an orally administered amino acid formulation comprising one or more modified release large neutral amino acids, wherein the formulation comprising 2 g of the modified release large neutral amino acids releases no more than x % of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein x % is 90%, 80%, 70%, 60%, 50% or even 40%.

In a seventh principal embodiment the invention provides an orally administered amino acid formulation comprising a combination of modified release non-essential amino acids wherein the formulation comprising 2 g of the modified release amino acids releases no more than x % of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein x % is 90%, 80%, 70%, 60%, 50% or even 40%.

The formulations are preferably in the form of edible granules that can be mixed with other foods such as yogurt, or large chewable tablets that cannot be swallowed whole, but must be eaten like a biscuit in several bites. The quantity of amino acids in the unit dose formulations will depend on the metabolic demands of the individual being treated generally depending on the individual's age, sex, weight, and physical activities, and whether the individual suffers from a metabolic disorder limiting his or her intake of one or more amino acids, as described in greater detail herein.

The formulation may comprise one, all, or any combination of essential and non-essential amino acids, and can be specifically designed for any application where amino acid supplementation is desired. The formulations are particularly well suited for the treatment of people with amino acid processing disorders such as phenylketonuria, tyrosinemia, leucinosis, methylmalonic acidemia, homocystinuria, hyperglycinemia, isovaleric acidemia, propionic acidemia, and glutamic acidemia.

The modified release can be accomplished by ingredients referred to herein variously as release retarding agents, means for preferentially releasing the amino acids in the jejunum, etc. These agents are capable of causing a modified release of amino acids from the formulation when ingested or when tested in dissolution media. Alternatively, they are capable of extending or delaying the release of amino acids so that some of the amino acids are not released until later in the digestive process, such as after the formulation has reached the higher pH environment of the small intestine. These agents are even capable, in a suitably designed formulation, of releasing a subset of amino acids in the formulation at a different release rate than other amino acids. The formulations are preferably released based on their modified release pattern when tested at a fixed pH value.

Other aspects of the present invention involve the use of the formulations to treat or manage a disease that requires close management of amino acid intake, commonly due to an impaired amino acid metabolism. Thus, in another embodiment, the invention provides a method of treating a metabolic disorder selected from the group consisting of phenylketonuria, tyrosinemia, leucinosis, methylmalonic acidemia, homocystinuria, hyperglycinemia, isovaleric acidemia, propionic acidemia, and glutamic acidemia, in a patient in need thereof, comprising orally administering to the patient an amino acid formulation of the present invention.

Yet another embodiment provides methods of making the formulations of the present invention, and in this embodiment the invention provides a method of making a formulation of the present invention comprising: (a) providing a first mixture comprising a single or plurality of amino acids; (b) contacting said mixture with a wetting agent or solvent (e.g. an alcohol and/or an organic solvent and/or water) and a binder to form a wet mixture; (c) optionally passing said wet mixture through a sieve to form a uniform wet granulate; (d) drying said uniform wet granulate to form a dry granulate; (e) optionally passing said dry granulate through a sieve to form a uniform dry granulate, and (f) optionally coating the dry granulate with one or more coating agents to provide a modified release to said dry granulate. Suitable coating agents include, for example, cellulose polymers, fatty acids, waxes and other coating agent able to provide a modified release to said dry granulate. Suitable coating techniques include, for example, fluid bed coating and melt granulation. The dry granulates can be incorporated into any conventional dosage form but preferably are used as the dosage form, without further modification, where they can easily be mixed with other ingredients such as flavors and inactive excipients or additives, or active ingredients such as vitamins, minerals and carbohydrates. Alternatively, the dry granulates can be compressed into a chewable tablet.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE FIGURES

This patent application file contains at least one drawing executed in color. Copies of this patent application with color drawings will be provided by the Office upon request and payment of the necessary fee.

FIG. 12 plots the aggregate amino acid ponderal dissolution profile from four separate ethylcellulose/glyceryl dibehenate coated modified release amino acid formulations, manufactured and tested as described in Example 12, having the compositions described in Table 11a.

DETAILED DESCRIPTION

Definitions

Figure 1:
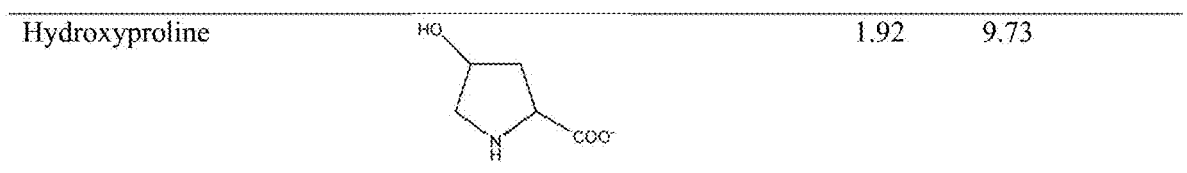
FIG. 1 tabulates the 19 amino acids used by the human body to synthesize proteins, and classifies them according to structure and properties, namely aliphatic, aromatic, acid, basic, sulphurated and $pK_a$.
Figure 2:
FIG. 2 tabulates essential amino acids, i.e. those amino acids that are not produced in the body through biochemical synthesis, but must be ingested with the diet, as reported by Montgomery et al., 1988.
Figure 2:

When the singular forms "a," "an" and "the" or like terms are used herein, they will be understood to include plural referents unless the context clearly dictates otherwise. Thus, for example, reference to "a hydrocarbon" includes mixtures of two or more such hydrocarbons, and the like. The word "or" or like terms as used herein means any one member of a particular list and also includes any combination of members of that list.

When used herein the term "about" or "ca." will compensate for variability allowed for in the pharmaceutical industry and inherent in pharmaceutical products, such as differences in product strength and bioavailability due to manufacturing variations and time-induced product degradation. The term allows for any variation which in the practice of pharmaceuticals would allow the product being evaluated to be considered pharmaceutically equivalent or bioequivalent, or both if the context requires, to the recited strength of a claimed product. It will be understood that all numeric values expressed in this document can be prefaced by the term "about."

The term "independently" is used to mean that the particular elements modified by a set of potential variables may or may not be defined by the same variable. Thus, for example, if a composition comprises z % of element A and z % of element B, and z can independently be 10% or 20%, the composition can comprise 10% of element A and 10% of element B, or 10% of element A and 20% of element B, etc.

The term "amino acid" refers to any naturally occurring amino acid capable of participating in the synthesis of peptides and proteins. For ease of drafting, the amino acid will frequently be written without its stereo-configuration, although it will be understood that the amino acid should be present as its naturally occurring stereoisomer.

In the formulations of the present invention, amino acids can be present as the free base, as the hydrochloride salt, or as another suitable salt. The term essential amino acid refers to any amino acid that the body is incapable of making itself, which must be derived from an external source. Essential amino acids that can be included in the formulations of the present invention include L-Isoleucine, L-Leucine, L-Lysine, L-Threonine, L-Tryptophan, L-Valine, L-Methionine, L-Phenylalanine, L-Histidine and L-Arginine or any of their pharmaceutically acceptable salts (these last two are considered essential only for infants although, for simplification, they are referred to as "essential amino acids herein").

The term non-essential amino acid refers to any amino acid other than an essential amino acid, and thus includes for example L-Alanine, L-Aspartic Acid, L-Cystine, L-Glutamine and/or L-Glutamic acid, Glycine, L-Proline, L-Serine, Taurine, L-Tyrosine, and L-Carnitine or any of their pharmaceutically acceptable salts. Any of these amino acids can be present, as the free base, the hydrochloride salt, or any other suitable salt.

The term "branched chain amino acids" refers to valine, isoleucine, and leucine, or any of their pharmaceutically acceptable salts.

The term "large neutral amino acids" in one embodiment refers to tryptophan, threonine, valine, isoleucine, leucine, and histidine, or any of their pharmaceutically acceptable salts. In another embodiment the term also includes phenylalanine, methionine and tyrosine.

The term "formulation" refers to a finished or semi-finished combination of pharmaceutical or medical food or food ingredients, including both active ingredients and inactive excipients or additives. The term refers to in-process formulations, finished formulations, and formulations packaged as a final unit dose.

Throughout the description and claims of this specification, the word "comprise" and variations of the word, such as "comprising" and "comprises," means "including but not limited to," and is not intended to exclude, for example, other additives, components, integers or steps.

The terms "treating" and "treatment," when used herein, refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. The term include also dietary management of a patient who, because of a specific disease or medical condition, has limited or impaired capacity to ingest, digest, adsorb or metabolize foodstuffs or nutrients or who has other special medically determined nutrient requirements, the dietary management of which cannot be achieved by the modification of the normal diet alone.

The term "modified release" refers to any pharmaceutical formulation in which the release rate is intentional altered to achieve a desired therapeutic or pharmacokinetic response. The term thus includes extended release formulations, in which the release of the drug is extended over time, or a release rate that is independent of the pH of the surrounding environment. The term also includes delayed release formulations, where the release of active ingredient from the formulation (or a portion thereof) is delayed to occur after the initial ingestion. A delayed release formulation is typically designed so that release occurs predominantly once the formulation reaches the small intestine.

As used herein, "therapeutically effective amount" refers to an amount sufficient to elicit the desired biological response. The therapeutically effective amount or dose will depend on the age, sex and weight of the patient, and the current medical condition of the patient. The skilled artisan will be able to determine appropriate dosages depending on these and other factors in addition to the present disclosure.

When used to refer to nutrients such as amino acids, minerals, vitamins, etc., the term refers to that amount generally recognized as necessary to support the human body's metabolic needs.

"Pharmaceutically acceptable" means that which is useful in preparing a pharmaceutical composition that is generally safe, non-toxic and neither biologically nor otherwise undesirable and includes that which is acceptable for veterinary use as well as human medical food, food and pharmaceutical use. "Pharmaceutically acceptable salts" means salts that are pharmaceutically or medical food or food acceptable, as defined above, and which possess the desired pharmacological or nutritive activity.

When ranges are expressed herein by specifying alternative upper and lower limits of the range, it will be understood that the endpoints can be combined in any manner that is mathematically feasible. Thus, for example, a range of from 50 or 80 to 100 or 70 can alternatively be expressed as a series of ranges of from 50 to 100, from 50 to 70, and from 80 to 100. When a series of upper bounds and lower bounds are related using the phase and/or, it will be understood that the upper bounds can be unlimited by the lower bonds or combined with the lower bounds, and vice versa. Thus, for example, a range of greater than 40% and/or less than 80% includes ranges of greater than 40%, less than 80%, and greater than 40% but less than 80%.

When a specific testing methodology is given from the United States Pharmacopoeia or other industry-accepted compendium herein, it will be understood that the test method can be modified according to usual and customary practices without altering the basic physical principals or end-results based on the conventional skill of the skilled artisan, and the examples provided herein, as, for example, may be needed to test different dosage forms.

When percentages are given herein, it will be understood that the percentages are weight percent, and that proportions are based on weight, unless otherwise stated to the contrary.

Discussion

The invention is defined in terms of principal embodiments and subembodiments, and it will be understood that the principal embodiments can be combined to define other principal embodiments, that the subembodiments can be combined to define additional subembodiments, and that the subembodiments and combinations of subembodiments can be combined with all of the principal embodiments to define further embodiments of the present invention. The ability to combine embodiments and subembodiments is limited only by what is mathematically or physically impossible.

In a first principal embodiment the invention provides an orally administered amino acid formulation comprising one or more modified release amino acids wherein the formulation comprising 2 g of the modified release amino acids releases no more than x % of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein x % is 90%, 80%, 70%, 60%, 50% or even 40%.

In a second principal embodiment the invention provides an orally administered amino acid formulation comprising a modified release amino acid selected from arginine, isoleucine, leucine, tyrosine and valine, wherein the formulation comprising 2 g of the modified release amino acids releases no more than x % of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein x % is 90%, 80%, 70%, 60%, 50%, or even 40%.

In a third principal embodiment the invention provides an orally administered amino acid formulation comprising modified release branched chain amino acids, wherein the formulation comprising 2 g of the modified release amino acids releases no more than x % of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein x % is 90%, 80%, 70%, 60%, 50% or even 40%. In a preferred embodiment the formulation includes modified release valine, isoleucine and leucine.

In a fourth principal embodiment, the invention provides an orally administered amino acid formulation comprising a combination of modified release essential amino acids wherein the formulation comprising 2 g of the modified release amino acids releases no more than x % of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein x % is 90%, 80%, 70%, 60%, 50% or even 40%. In a preferred embodiment the modified release amino acids include Arginine, Histidine, Isoleucine, Leucine, Threonine, Lysine and Tryptophan.

In a fifth principal embodiment, the invention provides an orally administered amino acid formulation comprising modified release large neutral amino acids, wherein the formulation comprising 2 g of the modified release large neutral amino acids releases no more than x % of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein x % is 90%, 80%, 70%, 60%, 50% or even 40%. In a preferred embodiment the formulation includes modified release tryptophan, threonine, valine, isoleucine, leucine, and histidine.

In a sixth principal embodiment the invention provides a method of treating a metabolic disorder selected from the group consisting of phenylketonuria, tyrosinemia, leucinosis, methylmalonic acidemia, homocystinuria, hyperglycinemia, isovaleric acidemia, propionic acidemia, and glutamic acidemia, in a patient in need thereof, comprising orally administering to the patient a formulation of the present invention defined by any of the principal embodiments or subembodiments.

In a seventh principal embodiment the invention provides an orally administered amino acid formulation comprising a combination of modified release non-essential amino acids wherein the formulation comprising 2 g of the modified release amino acids releases no more than x % of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein x % is 90%, 80%, 70%, 60%, 50% or even 40%.

In various subembodiments, the formulation may comprise one, all, or any combination of essential and non-essential amino acids, and can be specifically designed for any application where amino acid supplementation is desired. The formulations are particularly well suited for the treatment of people with amino acid processing disorders such as phenylketonuria, tyrosinemia, leucinosis, methylmalonic acidemia, homocystinuria, hyperglycinemia, isovaleric acidemia, propionic acidemia, and glutamic acidemia. Other more particular subembodiments are described more specifically in Tables B-D. It will be understood, however, that some flexibility should be incorporated in these formulation to account, for example, for the amino acid requirements of infants and children, which could cause some of the amino acid to fall out of the recited proportions.

Table B presents relative weight parts of nineteen amino acids, for use generally as modified release amino acids in formulations intended for amino acid supplementation, as well as phenylketonuria and tyrosinemia. Column A presents preferred ranges of suitable proportions of amino acids, while column B presents more preferred range of suitable proportions. Table B only describes the relative proportions of amino acids in the formulation. Thus, other ingredients can be included. The aggregate rates of amino acid release from any of the formulations described in Table B are preferably as recited in the first principal embodiment.

essential amino acids, the branched chain amino acids, or the large neutral amino acids encompassed by the general formulations of Table B (defined by Column A or B) in the proportions recited in columns A or B.

Further embodiments are defined when the first principal embodiment includes as modified release amino acids three or more, five or more, 10 or more, or 15 or more, or even all of the amino acids encompassed by the phenylketonuria formulations of Table B (defined by Column A or B) in the proportions recited in columns A or B.

Further embodiments are defined when the first principal embodiment includes as modified release amino acids the essential amino acids, the branched chain amino acids, or the large neutral amino acids encompassed by the phenylketonuria formulations of Table B (defined by Column A or B) in the proportions recited in columns A or B.

Further embodiments are defined when the first principal embodiment includes as modified release amino acids three or more, five or more, 10 or more, or 15 or more, or even all of the amino acids encompassed by the tyrosinemia formulations of Table B (defined by Column A or B) in the proportions recited in columns A or B.

Further embodiments are defined when the first principal embodiment includes as modified release amino acids the essential amino acids, the branched chain amino acids, or the large neutral amino acids encompassed by the tyrosinemia formulations of Table B (defined by Column A or B) in the proportions recited in columns A or B.

Table C presents relative weight parts of nineteen amino acids for use as modified release amino acids in leucinosis,

TABLE B

| | General | | Phenylketonuria | | Tyrosinemia | |
|---|---|---|---|---|---|---|
| | A | B | A | B | A | B |
| L-Alanine | 2.0-12.0 | 2.0-7.0 | 2.0-12.0 | 2.0-7.0 | 2.0-12.0 | 3.5-5.0 |
| L-Arginine | 3.0-10.5 | 3.0-8.2 | 3.0-10.5 | 3.0-8.0 | 3.0-10.5 | 7.0-8.0 |
| L-Aspartic Acid | 5.0-10.5 | 5.0-10.5 | 5.0-10.5 | 5.0-8.5 | 5.0-10.5 | 6.0-8.0 |
| L-Cystine | 1.5-4.0 | 1.5-4.0 | 1.5-4.0 | 1.0-3.0 | 1.5-4.0 | 2.5-3.5 |
| L-Glutamic Acid + Glutamine | 7.0-25.0 | 10.0-22.0 | 7.0-25.0 | 11.0-22.0 | 7.0-25.0 | 8.0-12.0 |
| Glycine | 3.5-15.0 | 4.0-8.0 | 3.5-15.0 | 4.0-6.0 | 3.5-15.0 | 6.0-8.0 |
| L-Histidine | 2.0-6.5 | 2.5-5.0 | 2.0-6.5 | 2.0-3.5 | 2.0-6.5 | 4.0-5.0 |
| L-Isoleucine | 2.0-8.5 | 4.0-7.0 | 2.0-8.5 | 4.5-6.5 | 2.0-8.5 | 6.0-8.0 |
| L-Leucine | 8.0-15.0 | 8.0-14.0 | 8.0-15.0 | 8.0-13.0 | 8.0-15.0 | 10.0-12.5 |
| L-Lysine | 4.5-10.5 | 4.9-9.0 | 4.5-10.5 | 4.9-8.0 | 4.5-10.5 | 7.5-9.5 |
| L-Methionine | 1.0-3.0 | 1.0-3.0 | 1.0-3.0 | 1.0-3.0 | 1.0-3.0 | 1.5-2.5 |
| L-Phenylalanine | 4.0-7.5 | 4.5-7.0 | 0.0 | 0.0 | 0.0 | 0.0 |
| L-Proline | 3.5-15.0 | 4.0-10.0 | 3.5-15.0 | 5.0-8.2 | 3.5-15.0 | 7.5-9.0 |
| L-Serine | 2.0-8.5 | 3.0-7.0 | 2.0-8.5 | 3.0-7.0 | 2.0-8.5 | 4.5-6.0 |
| L-Threonine | 4.0-7.5 | 4.0-6.5 | 4.0-7.5 | 4.0-6.0 | 4.0-7.5 | 5.0-6.5 |
| L-Tryptophan | 1.0-4.0 | 1.5-3.0 | 1.0-4.0 | 1.5-3.0 | 1.0-4.0 | 1.5-3.0 |
| L-Tyrosine | 2.5-14.0 | 6.5-12.0 | 2.5-14.0 | 6.5-12.0 | 0.0 | 0.0 |
| L-Valine | 2.5-10.0 | 4.0-8.0 | 2.5-10.0 | 4.0-8.0 | 2.5-10.0 | 6.5-8.0 |
| L-Carnitine | 0.0-0.2 | 0.05-0.2 | 0.0-0.2 | 0.05-0.2 | 0.0-0.2 | 0.0-0.2 |
| Taurine | 0.05-1.0 | 0.1-0.7 | 0.05-1.0 | 0.2-0.5 | 0.05-1.0 | 0.05-0.5 |

Further embodiments are defined when the first principal embodiment includes as modified release amino acids three or more, five or more, 10 or more, or 15 or more, or even all of the amino acids encompassed by the general formulations of Table B (defined by Column A or B) in the proportions recited in columns A or B.

Further embodiments are defined when the first principal embodiment includes as modified release amino acids the methylmalonic acidemia, propionic acidemia, and glutaric acidemia. Column A presents preferred ranges of suitable proportions of amino acids for each of these metabolic disorders, while column B presents more preferred range of suitable proportions. Table C only describes the relative proportions of amino acids in the formulation. Thus, other ingredients can be included. The aggregate rates of amino acid release from any of the formulations described in Table C are preferably as recited in the first principal embodiment.

TABLE C

| | Leucinosis | | Methylmalonic Acidemia or Propionic Acidemia | | Glutaric Acidemia | |
|---|---|---|---|---|---|---|
| | A | B | A | B | A | B |
| L-Alanine | 2.0-12.0 | 4.5-6.0 | 2.0-12.0 | 9.0-11.0 | 2.0-12.0 | 4.0-5.0 |
| L-Arginine | 3.0-10.5 | 8.5-10.5 | 3.0-10.5 | 8.0-10.0 | 3.0-10.5 | 7.0-8.5 |
| L-Aspartic Acid | 5.0-10.5 | 7.0-8.5 | 5.0-10.5 | 7.0-9.0 | 5.0-10.5 | 6.0-7.0 |
| L-Cystine | 1.5-4.0 | 3.0-4.0 | 1.5-4.0 | 3.0-4.0 | 1.5-4.0 | 2.5-3.5 |
| L-Glutamic Acid + Glutamine | 7.0-25.0 | 9.0-13.0 | 7.0-25.0 | 9.0-11.0 | 7.0-25.0 | 8.0-10.0 |
| Glycine | 3.5-15.0 | 7.5-9.5 | 3.5-15.0 | 3.5-4.5 | 3.5-15.0 | 6.5-8.0 |
| L-Histidine | 2.0-6.5 | 4.5-6.0 | 2.0-6.5 | 5.5-7.0 | 2.0-6.5 | 3.5-5.5 |
| L-Isoleucine | 0.0 | 0.0 | 0.0-0.5 | 0.0-0.5 | 2.0-8.5 | 6.0-8.5 |
| L-Leucine | 0.0 | 0.0 | 10.0-15.0 | 12.0-15.0 | 10.0-15.0 | 10.5-13.0 |
| L-Lysine | 4.5-10.5 | 8.5-10.5 | 4.5-10.5 | 8.0-10.5 | 0.0 | 0.0 |
| L-Methionine | 1.0-3.0 | 1.5-3.0 | 0.0 | 0.0 | 1.0-3.0 | 1.5-2.5 |
| L-Phenylalanine | 4.0-7.5 | 5.5-7.0 | 4.0-7.5 | 5.5-7.5 | 4.0-7.5 | 4.5-6.0 |
| L-Proline | 3.5-15.0 | 9.5-11.0 | 3.5-15.0 | 3.5-5.0 | 3.5-15.0 | 7.5-9.0 |
| L-Serine | 2.0-8.5 | 5.5-7.5 | 2.0-8.5 | 5.0-6.5 | 2.0-8.5 | 4.5-6.0 |
| L-Threonine | 4.0-7.5 | 6.5-8.0 | 0.0 | 0.0 | 4.0-7.5 | 5.0-6.5 |
| L-Tryptophan | 1.0-4.0 | 2.5-3.5 | 1.0-4.0 | 2.0-3.5 | 0.0-0.5 | 0.0-0.5 |
| L-Tyrosine | 2.5-14.0 | 2.5-7.0 | 2.5-14.0 | 5.0-7.0 | 2.5-14.0 | 4.5-6.0 |
| L-Valine | 0.0 | 0.0 | 0.0 | 0.0 | 2.5-10.0 | 6.5-8.0 |
| L-Carnitine | 0.0-0.2 | 0.02-0.12 | 0.0-0.2 | 0.0-0.15 | 0.0-0.2 | 0.0-0.2 |
| Taurine | 0.05-1.0 | 0.05-1.0 | 0.05-1.0 | 0.05-1.0 | 0.05-1.0 | 0.5-0.5 |

Further embodiments are defined when the first principal embodiment includes as modified release amino acids three or more, five or more, 10 or more, or 15 or more, or even all of the amino acids encompassed by the leucinosis formulations of Table C (defined by Column A or B) in the proportions recited in columns A or B.

Further embodiments are defined when the first principal embodiment includes as modified release amino acids the essential amino acids, the branched chain amino acids, or the large neutral amino acids encompassed by the leucinosis formulations of Table C (defined by Column A or B) in the proportions recited in columns A or B.

Further embodiments are defined when the first principal embodiment includes as modified release amino acids three or more, five or more, 10 or more, or 15 or more, or even all of the amino acids encompassed by the methylmalonic acidemia formulations of Table C (defined by Column A or B) in the proportions recited in columns A or B.

Further embodiments are defined when the first principal embodiment includes as modified release amino acids the essential amino acids, the branched chain amino acids, or the large neutral amino acids encompassed by the methylmalonic acidemia formulations of Table C (defined by Column A or B) in the proportions recited in columns A or B.

Further embodiments are defined when the first principal embodiment includes as modified release amino acids three or more, five or more, 10 or more, or 15 or more, or even all of the amino acids encompassed by the propionic acidemia formulations of Table C (defined by Column A or B) in the proportions recited in columns A or B.

Further embodiments are defined when the first principal embodiment includes as modified release amino acids the essential amino acids, the branched chain amino acids, or the large neutral amino acids encompassed by the propionic acidemia formulations of Table C (defined by Column A or B) in the proportions recited in columns A or B.

Further embodiments are defined when the first principal embodiment includes as modified release amino acids three or more, five or more, 10 or more, or 15 or more, or even all of the amino acids encompassed by the glutaric acidemia formulations of Table C (defined by Column A or B) in the proportions recited in columns A or B.

Further embodiments are defined when the first principal embodiment includes as modified release amino acids the essential amino acids, the branched chain amino acids, or the large neutral amino acids encompassed by the glutaric acidemia formulations of Table C (defined by Column A or B) in the proportions recited in columns A or B.

Table D presents relative weight parts of nineteen amino acids for use as modified release amino acids in isovaleric acidemia, homocystinuria, and hyperglycinemia. Column A presents preferred ranges of suitable proportions of amino acids for each of these metabolic disorders, while column B presents more preferred ranges of suitable proportions. Table D only describes the relative proportions of amino acids in the formulation. Thus, other ingredients can be included. The aggregate rates of amino acid release from any of the formulations described in Table D are preferably as recited in the first principal embodiment.

TABLE D

| | Isovaleric Acidemia | | Homcystinuria | | Hyperglycinemia | |
|---|---|---|---|---|---|---|
| | A | B | A | B | A | B |
| L-Alanine | 2.0-12.0 | 4.0-6.0 | 2.0-12.0 | 3.0-5.0 | 2.0-12.0 | 3.5-5.0 |
| L-Arginine | 3.0-10.5 | 7.0-9.0 | 3.0-10.5 | 6.5-8.0 | 3.0-10.5 | 6.5-8.5 |
| L-Aspartic Acid | 5.0-10 | 6.0-7.0 | 5.0-10.0 | 5.0-7.0 | 5.0-10.0 | 6.0-8.0 |
| L-Cystine | 1.5-4.0 | 2.5-3.5 | 1.5-4.0 | 2.0-3.0 | 1.5-4.0 | 2.0-3.5 |

TABLE D-continued

|  | Isovaleric Acidemia | | Homcystinuria | | Hyperglycinemia | |
| --- | --- | --- | --- | --- | --- | --- |
|  | A | B | A | B | A | B |
| L-Glutamic Acid + Glutamine | 7.0-25.0 | 8.0-9.5 | 7.0-25.0 | 7.5-9.0 | 7.0-25.0 | 7.0-10.0 |
| Glycine | 3.5-15.0 | 13.0-16.0 | 3.5-15.0 | 5.5-7.0 | 0.0 | 0.0 |
| L-Histidine | 2.0-6.5 | 4.0-5.0 | 2.0-6.5 | 3.5-4.5 | 2.0-6.5 | 4.0-5.0 |
| L-Isoleucine | 2.0-8.5 | 2.0-3.5 | 2.0-8.5 | 5.5-7.0 | 2.0-8.5 | 6.0-8.5 |
| L-Leucine | 0.0 | 0.0 | 10.0-15.0 | 10.0-12.0 | 10.0-15.0 | 10.0-12.5 |
| L-Lysine | 4.5-10.5 | 6.0-7.5 | 4.5-10.5 | 7.0-8.0 | 4.5-10.5 | 7.0-8.5 |
| L-Methionine | 1.0-3.0 | 1.5-2.5 | 0.0 | 0.0 | 1.0-3.0 | 1.0-2.5 |
| L-Phenylalanine | 4.0-7.5 | 5.0-6.0 | 4.0-7.5 | 4.0-5.5 | 4.0-7.5 | 4.5-6.0 |
| L-Proline | 3.5-15.0 | 13.0-15.0 | 3.5-15.0 | 7.0-8.5 | 3.5-15.0 | 7.0-9.0 |
| L-Serine | 2.0-8.5 | 4.0-5.0 | 2.5-8.5 | 5.0-8.5 | 2.5-8.5 | 4.5-5.5 |
| L-Threonine | 4.0-7.5 | 4.0-5.5 | 4.0-7.5 | 5.0-6.0 | 4.0-7.5 | 5.0-6.5 |
| L-Tryptophan | 1.0-4.0 | 1.5-2.5 | 1.0-4.0 | 1.5-2.5 | 1.0-4.0 | 2.0-3.0 |
| L-Tyrosine | 2.5-14.0 | 4.5-6.0 | 2.5-14.0 | 4.5-6.0 | 2.5-14.0 | 4.0-6.0 |
| L-Valine | 2.5-10.0 | 2.5-4.0 | 2.5-8.0 | 6.0-8.0 | 2.5-10.0 | 6.0-8.0 |
| L-Carnitine | 0.0-0.2 | 0.0-0.15 | 0.0-0.2 | 0.0-0.1 | 0.0-0.2 | 0.05-0.2 |
| Taurine | 0.05-1.0 | 0.05-0.5 | 0.05-1.0 | 0.5-0.5 | 0.05-1.0 | 0.1-0.5 |

Further embodiments are defined when the first principal embodiment includes as modified release amino acids three or more, five or more, 10 or more, or 15 or more, or even all of the amino acids encompassed by the isovaleric acidemia formulations of Table D (defined by Column A or B) in the proportions recited in columns A or B.

Further embodiments are defined when the first principal embodiment includes as modified release amino acids the essential amino acids, the branched chain amino acids, or the large neutral amino acids encompassed by the isovaleric acidemia formulations of Table D (defined by Column A or B) in the proportions recited in columns A or B.

Further embodiments are defined when the first principal embodiment includes as modified release amino acids three or more, five or more, 10 or more, or 15 or more, or even all of the amino acids encompassed by the homocystinuria formulations of Table D (defined by Column A or B) in the proportions recited in columns A or B.

Further embodiments are defined when the first principal embodiment includes as modified release amino acids the essential amino acids, the branched chain amino acids, or the large neutral amino acids encompassed by the homocystinuria formulations of Table D (defined by Column A or B) in the proportions recited in columns A or B.

Further embodiments are defined when the first principal embodiment includes as modified release amino acids three or more, five or more, 10 or more, or 15 or more, or even all of the amino acids encompassed by the hyperglycinemia formulations of Table D (defined by Column A or B) in the proportions recited in columns A or B.

Further embodiments are defined when the first principal embodiment includes as modified release amino acids the essential amino acids, the branched chain amino acids, or the large neutral amino acids encompassed by the hyperglycinemia formulations of Table D (defined by Column A or B) in the proportions recited in columns A or B.

Additional subembodiments are defined when the third principal embodiment is limited by the relative proportions of branched chain amino acids recited in table E1-E3.

TABLE E1

|  | General | | Phenylketonuria | | Tyrosinemia | |
| --- | --- | --- | --- | --- | --- | --- |
|  | A | B | A | B | A | B |
| L-Isoleucine | 2.0-8.5 | 4.0-7.0 | 2.0-8.5 | 4.5-6.5 | 2.0-8.5 | 6.0-8.0 |
| L-Leucine | 8.0-15.0 | 8.0-14.0 | 8.0-15.0 | 8.0-13.0 | 8.0-15.0 | 10.0-12.5 |
| L-Valine | 2.5-10.0 | 4.0-8.0 | 2.5-10.0 | 4.0-8.0 | 2.5-10.0 | 6.5-8.0 |

TABLE E2

|  | Leucinosis | | Methylmalonic Acidemia or Propionic Acidemia | | Glutaric Acidemia | |
| --- | --- | --- | --- | --- | --- | --- |
|  | A | B | A | B | A | B |
| L-Isoleucine | 0.0 | 0.0 | 0.0-0.5 | 0.0-0.5 | 2.0-8.5 | 6.0-8.5 |
| L-Leucine | 0.0 | 0.0 | 10.0-15.0 | 12.0-15.0 | 10.0-15.0 | 10.5-13.0 |
| L-Valine | 0.0 | 0.0 | 0.0 | 0.0 | 2.5-10.0 | 6.5-8.0 |

TABLE E3

|  | Isovaleric Acidemia | | Homcystinuria | | Hyperglycinemia | |
| --- | --- | --- | --- | --- | --- | --- |
|  | A | B | A | B | A | B |
| L-Isoleucine | 2.0-8.5 | 2.0-3.5 | 2.0-8.5 | 5.5-7.0 | 2.0-8.5 | 6.0-8.5 |
| L-Leucine | 0.0 | 0.0 | 10.0-15.0 | 10.0-12.0 | 10.0-15.0 | 10.0-12.5 |
| L-Valine | 2.5-10.0 | 2.5-4.0 | 2.5-8.0 | 6.0-8.0 | 2.5-10.0 | 6.0-8.0 |

Additional subembodiments are defined when the fourth principal embodiment is limited by the relative porportions of essential amino acids (Arginine, Histidine, Isoleucine, Leucine, Lysine, Threonine, Tryptophan and Valine) recited in tables F1-F3.

TABLE F1

|  | General | | Phenylketonuria | | Tyrosinemia | |
| --- | --- | --- | --- | --- | --- | --- |
|  | A | B | A | B | A | B |
| L-Arginine | 3.0-10.5 | 3.0-8.2 | 3.0-10.5 | 3.0-8.0 | 3.0-10.5 | 7.0-8.0 |
| L-Histidine | 2.0-6.5 | 2.5-5.0 | 2.0-6.5 | 2.0-3.5 | 2.0-6.5 | 4.0-5.0 |
| L-Isoleucine | 2.0-8.5 | 4.0-7.0 | 2.0-8.5 | 4.5-6.5 | 2.0-8.5 | 6.0-8.0 |
| L-Leucine | 8.0-15.0 | 8.0-14.0 | 8.0-15.0 | 8.0-13.0 | 8.0-15.0 | 10.0-12.5 |
| L-Lysine | 4.5-10.5 | 4.9-9.0 | 4.5-10.5 | 4.9-8.0 | 4.5-10.5 | 7.5-9.5 |
| L-Threonine | 4.0-7.5 | 4.0-6.5 | 4.0-7.5 | 4.0-6.0 | 4.0-7.5 | 5.0-6.5 |
| L-Tryptophan | 1.0-4.0 | 1.5-3.0 | 1.0-4.0 | 1.5-3.0 | 1.0-4.0 | 1.5-3.0 |
| L-Valine | 2.5-10.0 | 4.0-8.0 | 2.5-10.0 | 4.0-8.0 | 2.5-10.0 | 6.5-8.0 |

TABLE F2

|  | Leucinosis | | Methylmalonic Acidemia or Propionic Acidemia | | Glutaric Acidemia | |
| --- | --- | --- | --- | --- | --- | --- |
|  | A | B | A | B | A | B |
| L-Arginine | 3.0-10.5 | 8.5-10.5 | 3.0-10.5 | 8.0-10.0 | 3.0-10.5 | 7.0-8.5 |
| L-Histidine | 2.0-6.5 | 4.5-6.0 | 2.0-6.5 | 5.5-7.0 | 2.0-6.5 | 3.5-5.5 |
| L-Isoleucine | 0.0 | 0.0 | 0.0-0.5 | 0.0-0.5 | 2.0-8.5 | 6.0-8.5 |
| L-Leucine | 0.0 | 0.0 | 10.0-15.0 | 12.0-15.0 | 10.0-15.0 | 10.5-13.0 |
| L-Lysine | 4.5-10.5 | 8.5-10.5 | 4.5-10.5 | 8.0-10.5 | 0.0 | 0.0 |
| L-Threonine | 4.0-7.5 | 6.5-8.0 | 0.0 | 0.0 | 4.0-7.5 | 5.0-6.5 |
| L-Tryptophan | 1.0-4.0 | 2.5-3.5 | 1.0-4.0 | 2.0-3.5 | 0.0-0.5 | 0.0-0.5 |
| L-Valine | 0.0 | 0.0 | 0.0 | 0.0 | 2.5-10.0 | 6.5-8.0 |

TABLE F3

|  | Isovaleric Acidemia | | Homcystinuria | | Hyperglycinemia | |
| --- | --- | --- | --- | --- | --- | --- |
|  | A | B | A | B | A | B |
| L-Arginine | 3.0-10.5 | 7.0-9.0 | 3.0-10.5 | 6.5-8.0 | 3.0-10.5 | 6.5-8.5 |
| L-Histidine | 2.0-6.5 | 4.0-5.0 | 2.0-6.5 | 3.5-4.5 | 2.0-6.5 | 4.0-5.0 |
| L-Isoleucine | 2.0-8.5 | 2.0-3.5 | 2.0-8.5 | 5.5-7.0 | 2.0-8.5 | 6.0-8.5 |
| L-Leucine | 0.0 | 0.0 | 10.0-15.0 | 10.0-12.0 | 10.0-15.0 | 10.0-12.5 |
| L-Lysine | 4.5-10.5 | 6.0-7.5 | 4.5-10.5 | 7.0-8.0 | 4.5-10.5 | 7.0-8.5 |
| L-Threonine | 4.0-7.5 | 4.0-5.5 | 4.0-7.5 | 5.0-6.0 | 4.0-7.5 | 5.0-6.5 |
| L-Tryptophan | 1.0-4.0 | 1.5-2.5 | 1.0-4.0 | 1.5-2.5 | 1.0-4.0 | 2.0-3.0 |
| L-Valine | 2.5-10.0 | 2.5-4.0 | 2.5-8.0 | 6.0-8.0 | 2.5-10.0 | 6.0-8.0 |

Additional subembodiments are defined when the fifth principal embodiment is limited by the relative proportions of large neutral amino acids recited in table G1-G3.

TABLE G1

|  | General | | Phenylketonuria | | Tyrosinemia | |
| --- | --- | --- | --- | --- | --- | --- |
|  | A | B | A | B | A | B |
| L-Histidine | 2.0-6.5 | 2.5-5.0 | 2.0-6.5 | 2.0-3.5 | 2.0-6.5 | 4.0-5.0 |
| L-Isoleucine | 2.0-8.5 | 4.0-7.0 | 2.0-8.5 | 4.5-6.5 | 2.0-8.5 | 6.0-8.0 |
| L-Leucine | 8.0-15.0 | 8.0-14.0 | 8.0-15.0 | 8.0-13.0 | 8.0-15.0 | 10.0-12.5 |
| L-Threonine | 4.0-7.5 | 4.0-6.5 | 4.0-7.5 | 4.0-6.0 | 4.0-7.5 | 5.0-6.5 |
| L-Tryptophan | 1.0-4.0 | 1.5-3.0 | 1.0-4.0 | 1.5-3.0 | 1.0-4.0 | 1.5-3.0 |
| L-Valine | 2.5-10.0 | 4.0-8.0 | 2.5-10.0 | 4.0-8.0 | 2.5-10.0 | 6.5-8.0 |

TABLE G3

|  | Leucinosis | | Methylmalonic Acidemia or Propionic Acidemia | | Glutaric Acidemia | |
| --- | --- | --- | --- | --- | --- | --- |
|  | A | B | A | B | A | B |
| L-Histidine | 2.0-6.5 | 4.5-6.0 | 2.0-6.5 | 5.5-7.0 | 2.0-6.5 | 3.5-5.5 |
| L-Isoleucine | 0.0 | 0.0 | 0.0-0.5 | 0.0-0.5 | 2.0-8.5 | 6.0-8.5 |
| L-Leucine | 0.0 | 0.0 | 10.0-15.0 | 12.0-15.0 | 10.0-15.0 | 10.5-13.0 |
| L-Threonine | 4.0-7.5 | 6.5-8.0 | 0.0 | 0.0 | 4.0-7.5 | 5.0-6.5 |
| L-Tryptophan | 1.0-4.0 | 2.5-3.5 | 1.0-4.0 | 2.0-3.5 | 0.0-0.5 | 0.0-0.5 |
| L-Valine | 0.0 | 0.0 | 0.0 | 0.0 | 2.5-10.0 | 6.5-8.0 |

TABLE G3

|  | Isovaleric Acidemia | | Homcystinuria | | Hyperglycinemia | |
| --- | --- | --- | --- | --- | --- | --- |
|  | A | B | A | B | A | B |
| L-Histidine | 2.0-6.5 | 4.0-5.0 | 2.0-6.5 | 3.5-4.5 | 2.0-6.5 | 4.0-5.0 |
| L-Isoleucine | 2.0-8.5 | 2.0-3.5 | 2.0-8.5 | 5.5-7.0 | 2.0-8.5 | 6.0-8.5 |
| L-Leucine | 0.0 | 0.0 | 10.0-15.0 | 10.0-12.0 | 10.0-15.0 | 10.0-12.5 |
| L-Threonine | 4.0-7.5 | 4.0-5.5 | 4.0-7.5 | 5.0-6.0 | 4.0-7.5 | 5.0-6.5 |
| L-Tryptophan | 1.0-4.0 | 1.5-2.5 | 1.0-4.0 | 1.5-2.5 | 1.0-4.0 | 2.0-3.0 |
| L-Valine | 2.5-10.0 | 2.5-4.0 | 2.5-8.0 | 6.0-8.0 | 2.5-10.0 | 6.0-8.0 |

In another subembodiment for the treatment of phenylketonuria, defined without regard to the proportions of amino acids, the formulation of the present invention comprises three or more of, five or more of, or all of, arginine, histidine, isoleucine, leucine, lysine, methionine, threonine, tryptophan, and valine, or one or more pharmaceutically acceptable salts thereof, as modified release essential amino acids.

In another subembodiment for the treatment of phenylketonuria, again defined without regard to the proportions of amino acids, the formulations of the present invention comprise three or more of, five or more of, or all of, arginine, histidine, isoleucine, leucine, lysine, methionine, threonine, tryptophan, and valine, or one or more pharmaceutically acceptable salts thereof, as modified release essential amino acids; and three or more of, five or more of, or all of, alanine, aspartic acid, carnitine, cystine, glutamine and/or glutamic acid, glycine, proline, serine, taurine, and tyrosine, or one or more pharmaceutically acceptable salts thereof, as modified release non-essential amino acids.

In one particular subembodiment, which is suitable for the treatment of any of the metabolic disorders described herein, defined without regard to the proportions of ingredients, the formulation comprises arginine and histidine, or one or more pharmaceutically acceptable salts thereof, as modified release essential amino acids; and alanine, aspartic acid, carnitine, cystine, glutamine and/or glutamic acid, proline, serine, and taurine, or one or more acceptable salts thereof, as modified release non-essential amino acids.

In a particularly preferred embodiment, the formulation is provided as a single dose, unit dosage form, comprising from 1 to 40 grams of amino acids, wherein the formulation is therapeutically effective to meet the amino acid dietary needs of a human patient when administered three to four times per day. I.e., the formulation is adequate to meet the patient's dietary needs for the amino acids which are actually present in the formulation.

In another principal embodiment, the invention provides a method of making the formulation defined by any of the principal embodiments or subembodiments of the present invention, comprising: (a) providing a first mixture comprising a single or plurality of amino acids; (b) contacting the mixture with a wetting agent and a binder to form a wet mixture; (c) optionally passing the wet mixture through a sieve to form a uniform wet granulate; (d) drying the uniform wet granulate to form a dry granulate; (e) optionally passing the dry granulate through a sieve to form a uniform dry granulate; and (f) optionally coating the uniform dry granulate with a modified release composition.

The method is particularly well suited for mixing large number of amino acids, and could be adapted further by preparing more than one granulate with different mixtures of amino acids, and combining the different granulates to make the final formulation. Thus, in a preferred embodiment of the method of manufacture, the first mixture could comprise only one type of amino acid, or as many as 6 amino acids, further comprising repeating steps (a)-(d) and optionally (e) and (f) with a second different mixture of amino acids comprising only one amino acid, or as many as 6 amino acids to form a second uniform dry granulate, and combining the uniform dry granulates to make the formulation. In one embodiment the granulates are compressed to form a chewable tablet. In another embodiment, after the granulate mixture is formed, it is further processed by, for example the addition of flavorings or nutrients.

The formulations can also be defined based on the percentage of amino acids in the formulation. Thus, for example, the invention further provides formulations comprising greater than 20 wt %, 70 wt % or 90 wt % amino acids, wherein (a) said amino acids comprise from about 10 wt % to about 80 wt %, from about 20 wt % to about 60 wt %, from about 30 to about 50%, or from about 35 to about 45% essential amino acids; and (b) said essential amino acids comprise all or any combination of L-Isoleucine, L-Leucine, L-Lysine, L-Threonine, L-Tryptophan, L-Valine, L-Methionine, L-Histidine and L-Arginine (the last two ones are considered essential only for infants).

Alternatively, the modified release formulation can be defined based on the ratio of essential to non-essential amino acids in the formulation. Thus, in various embodiments the invention provides a modified release orally administered amino acid formulation comprising greater than 20 wt %, 50%, 70 wt % or 90 wt % amino acids, wherein (a) said amino acids comprise essential and non-essential amino acids in a weight ratio of from about 10:90, 20:80. 30:70, 40:60, 50:50, 60:40, 70:30 80:20 to about 90:10, 80:20, 70:30, 60:40, 50:50. 40:60, 30:70, or 20:80; and (b) said essential amino acids comprise all or any combination of L-Isoleucine, L-Leucine, L-Lysine, L-Threonine, L-Tryptophan, L-Valine, L-Methionine, L-Histidine and L-Arginine (the last two ones are considered essential only for infants).

The formulation preferably includes one or more excipients or additives capable of controlling the release of all the amino acids in the formulation, or a subset of the amino acids. These excipients or additives are referred to herein generally as "release retarding excipients or additives," and are capable of providing an extended release profile, a delayed release profile, a combination of immediate release and extended release or delayed release profiles. In one embodiment the excipients or additives are delayed release excipients or additives and are referred to as "means for preferentially releasing said amino acids at a pH between 4 and 7" or "means for preferentially releasing said amino acids in the jejunum when orally administered." In such case the excipient is typically present in an amount effective to cause preferential release of said amino acids from said formulation at a pH between 4 and 7.

The term "preferential release" does not exclude the possibility that some of the excipient will release amino acids in a lower pH environment, or even that the rate of release in a lower pH environment will equal that which occurs in a higher pH environment. The important point is that the excipient reduces the total quantity of amino acids that would otherwise be released in the low pH environment of the stomach versus an immediate release dosage form. Thus, for example, the excipient can yield a slower release profile over time as the formulation travels through the GI tract than would otherwise occur with an immediate release formulation, or as modeled in a suitable in vitro experiment. Alternatively, the excipient can retard the release until the formulation reaches the higher pH environment of the jejunum.

Release modifying excipients or additives/coating agents are well known to those of skill in the art and include, for example, ethylcellulose, cellulose acetate, vinyl acetate/vinyl chloride copolymers, acrylate/methacrylate copolymers, polyethylene oxide, hydroxypropyl methylcellulose, carrageenan, alginic acid and salts thereof, hydroxyethyl cellulose, hydroxypropyl cellulose, karaya gum, acacia gum, tragacanth gum, locust bean gum, guar gum, xanthan gum, sodium carboxymethyl cellulose, methyl cellulose, beeswax, carnauba wax, cetyl alcohol, hydrogenated vegetable oils, stearyl alcohol, acrylic acid copolymers, carrageenan, pectin, one sodium carboxymethyl cellulose, mono and diglycerides of fatty acids, fatty acids and their esters or derivatives including glyceryl behenates and glyceryl dipalmitostearate, starches and their derivatives such as maize acetate.

Formulations

These compositions of the present invention can be prepared in a manner well known in the pharmaceutical and food supplement art, and can be administered by a variety of routes depending upon whether local or systemic treatment is desired. The most preferred route of administration is oral.

The compositions will typically contain, in addition to the amino acids, one or more acceptable carriers (excipients or additives). In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills (including soft and hard gelatin capsules), powders, granulates, microspheres, lozenges, sachets (i.e. packaged powders or granulates or microspheres) sachets, elixirs, suspensions, emulsions, solutions, and syrups, containing, for example, up to 90% by weight amino acids.

Using this technology is possible to design various amino acid products, in which all or only a select portion of amino acids has the modified release profile. For example it is possible to design a formulation where:

- all or only a portion of the amino acids in the formulation are formulated for modified release. I.e., greater than 20%, 40%, 60% or 80%, and/or less than 80%, 60%, 40%, or 20% of the amino acids are formulated for modified release.
- all or only a portion of the essential amino acids in the formulation are formulated for modified release. I.e., greater than 20%, 40%, 60% or 80%, and/or less than 80%, 60%, 40%, or 20% of the essential amino acids are formulated for modified release.
- none of the essential amino acids are formulated for modified release.
- all or only a portion of the non-essential amino acids in the formulation are formulated for modified release. I.e., greater than 20%, 40%, 60% or 80%, and/or less than 80%, 60%, 40%, or 20% of the non-essential amino acids are formulated for modified release.
- none of the non-essential amino acids are formulated for modified release.
- any combination of the foregoing strategies.

For example, using the formulation strategies described in this application, it is possible to formulate amino acid dosage forms, so that only the essential amino acids are formulated for modified release, and the non-essential amino acids are not. Alternatively, it is possible to formulate amino acid dosage forms so that only the non-essential amino acids are formulated for modified release, and the essential amino acids are not. Alternatively, depending on the results of release testing for a particular formulation, it might be best to keep some of the amino acids, such as tyrosine, as immediate release amino acids.

Various strategies are available to control the release of amino acids from the formulation, depending on the desired pharmacokinetic profile. These strategies will typically involve non-pH dependent excipients or additives, so that the formulation releases amino acids independently of its location in the gastrointestinal tract, or pH-dependent excipients or additives, to delay the release of amino acids until the formulation reaches the higher pH environment of the small intestine.

Non-pH-dependent sustained release agents/coatings which may be included in the composition include, but are not limited to, ethylcellulose, cellulose acetate, vinyl acetate/vinyl chloride copolymers, acrylate/methacrylate copolymers, polyethylene oxide, hydroxypropyl methylcellulose, carrageenan, alginic acid and salts thereof, hydroxyethyl cellulose, hydroxypropyl cellulose, xanthan gum, karaya gum, acacia gum, tragacanth gum, locust bean gum, guar gum, sodium carboxymethyl cellulose, methyl cellulose, beeswax, carnauba wax, cetyl alcohol, hydrogenated vegetable oils, stearyl alcohol, fatty acids and their esters or derivatives including for example glyceryl behenates and glyceryl dipalmitostearate, xanthan gum, starches, and derivatives of starches such as maize acetate.

In general, the at least one non-pH-dependent modified release agent is present in the composition in an amount of from about 1 wt % or 5 wt % to about 50 wt % or 25 wt %, preferably from about 1 wt % to about 30 wt %. It is to be understood, however, that the scope of the present invention is not to be limited to any particular non-pH-dependent sustained release agents.

pH-dependent agents that increase the rate of release of the amino acids from the formulation at a pH in excess of 5.5 include, but are not limited to, polymers that swell at a pH in excess of 5.5, enteric agents for coating the amino acid, and agents that increase the solubility of the amino acids at a pH greater than 5.5, by maintaining an acidic microenvironment in the formulation, e.g., an organic acid. Suitable organic acids include, for example, formic acid, acetic acid, propionic acid, butyric acid, valeric acid, caproic acid, oxalic acid, lactic acid, malic acid, citric acid, benzoic acid, and carbonic acid. Any combination of these strategies can be employed to promote the release of amino acids at a pH greater than 5.5. The at least one pH-dependent agent is typically present in the composition in an amount of from about 0.5 wt. % to about 40 wt. %, preferably from about 1 wt. % to about 20 wt. %.

Polymers that swell at a pH in excess of 5.5 include, but are not limited to, acrylic acid copolymers, methacrylic acid copolymers (including for example those sold under the Eudragit® brand), sodium alginate, carrageenan, alginic acid, pectin, and sodium carboxymethyl cellulose.

Enteric agents include, but are not limited to, cellulose acetate phthalate, hydroxypropyl methylcellulose phthalate, polyvinyl acetate phthalate, methacrylic acid copolymers, cellulose acetate trimellitate, hydroxypropyl methylcellulose acetate, succinate, shellac, and zein.

Agents that increase the solubility of the amino acids at a pH greater than 5.5 include, but are not limited to, organic acids. Such organic acids maintain an acidic microenvironment in the tablet, and include, but are not limited to, citric acid, fumaric acid, tartaric acid, adipic acid, glucono deltalactone, and malic acid.

The compositions of the present invention are typically first prepared by wet granulation, coating and, if a biscuit is desired, subsequently compressed into a biscuit dosage form after mixing with other suitable excipients or additives such as lubricants, anti-adherents and disintegrating agents. Flavoring agents can be added during the granulation steps so that they are part of the granules or "intragranular," or subsequently mixed with the granulates, prior to compression of the granulates and optionally before being compressed into a tablet/biscuit.

In the wet granulation method, the at least one amino acid and other ingredients are granulated with a granulating fluid (e.g., isopropyl alcohol, ethyl alcohol, trichloromethane or water) in a planetary mixer, high shear mixer, or fluidized bed granulator. Binding agents may be contained in the granulating fluid, or may be in the dry mix. The wet granules are dried in an oven or fluidized bed dryer, and then sieved through a suitable screen to obtain free flowing granules that can be then be coated with functional excipients or additives able to give a modified or prolonged or delayed release profile.

Bulking agents can be included within the granules or biscuit formulation and include, but are not limited to, microcrystalline cellulose, mannitol, xylitol, dicalcium phosphate, calcium sulfate, starches, lactose, sucrose, dextrose, sorbitol, fructose, and cellulose powder. When present, the bulking agent may be present in the composition in an amount of from about 5 wt. % to about 90 wt. %, preferably from about 10 wt. % to about 50 wt. %.

Disintegrating agents which may be included in the formulations include, but are not limited to, microcrystalline cellulose, starches, crospovidone, sodium starch glycolate, and crosscarmellose sodium. When present, the disintegrating agent may be present in the composition in an amount of from about 0.5 wt. % to about 30 wt %, preferably from about 1 wt. % to about 15 wt. %.

Anti-adherants and glidants which may be employed in the composition include, but are not limited to, talc, corn starch, silicon dioxide, sodium lauryl sulfate, and metallic stearates. When present, the antiadherant or glidant may be present in the composition in an amount of from about 0.2 wt. % to about 15 wt. %, preferably from about 0.5 wt. % to about 5 wt. %.

Lubricants which may be employed in the composition include, but are not limited to, magnesium stearate, calcium stearate, sodium stearate, stearic acid, sodium stearyl fumarate, hydrogenated cotton seed oil, talc, and waxes, including but not limited to, beeswax, carnuba wax, cetyl alcohol, glyceryl stearate, glyceryl palmitate, glyceryl behenate, hydrogenated vegetable oils, and stearyl alcohol. When present, the lubricant may be present in an amount of from about 0.2 wt. % to about 20 wt. %, preferably from about 0.5 wt. % to about 5 wt. %.

Binding agents ("binders") which may be employed include, but are not limited to, polyvinyl pyrrollidone, starch, methylcellulose, hydroxypropyl methylcellulose, carboxymethyl cellulose, sucrose solution, dextrose solution, guar gum, xanthan gum, acacia, tragacanth, locust bean gum and sodium alginate or any other alginic acid salt. When present, the binding agent may be present in the composition in an amount of from about 0.2 wt. % to about 10 wt. %, preferably from about 0.5 wt. % to about 5 wt. %.

Coating agents which may be included in the composition include, but are not limited to, ethylcellulose, cellulose acetate, vinyl acetate/vinyl chloride copolymers, acrylate/methacrylate copolymers, polyethylene oxide, hydroxypropyl methylcellulose, carrageenan, alginic acid and salts thereof, hydroxyethyl cellulose, hydroxypropyl cellulose, karaya gum, acacia gum, tragacanth gum, locust bean gum, guar gum, sodium carboxymethyl cellulose, methyl cellulose, beeswax, carnauba wax, cetyl alcohol, hydrogenated vegetable oils, stearyl alcohol, fatty acids and their esters or derivatives including, glyceryl behenates and glyceryl dipalmitostearate, xanthan gum, starches, and starch derivatives including maize acetate.

Taste-Masking Materials

Amino Acids are inherently bitter tasting and in one embodiment of the present invention, these bitter Amino Acids are microencapsulated with a taste-masking material. Materials useful for masking the taste of pharmaceutical formulations include those materials capable of microencapsulating the Amino Acid, thereby protecting the senses from its bitter taste. Taste-masking materials of the present invention provide superior pharmaceutical formulations by e.g., creating a more palatable pharmaceutical formulation as compared to pharmaceutical formulations and/or by creating a dosage form requiring less of the traditional flavoring or taste masking agents.

Taste-masking materials include, e.g., cellulose hydroxypropyl ethers (HPC); low-substituted hydroxypropyl ethers (L-HPC); cellulose hydroxypropyl methyl ethers (HPMC); methylcellulose polymers; Ethylcelluloses (EC) and mixtures thereof; Polyvinyl alcohol (PVA); hydroxyethylcelluloses; carboxymethylcelluloses and salts of carboxymethylcelluloses (CMC); polyvinyl alcohol and polyethylene glycol co-polymers; monoglycerides, triglycerides, polyethylene glycols, modified food starch, acrylic polymers and mixtures of acrylic polymers with cellulose ethers; cellulose acetate phthalate; sepifilms such as mixtures of HPMC and stearic acid, cyclodextrins, and mixtures of these materials.

In addition to microencapsulating the Amino Acids with a taste-masking material or a material that enhances the shelf-life of the formulation as described herein, the pharmaceutical formulations of the present invention may also comprise one or more flavoring agents. "Flavoring agents" or "sweeteners" useful in the pharmaceutical formulations of the present invention include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, raspberry, root beer, rum, saccharin, safrole, sorbitol, spearmint, spearmint cream, strawberry, strawberry cream, *stevia*, sucralose, sucrose, sodium saccharin, saccharin, aspartame, neotame, acesulfame potassium, mannitol, talin, xylitol, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof. In other embodiments, sodium chloride is incorporated into the pharmaceutical formulation.

Based on the amino acids and excipients or additives, one of skilled in the art would be able to determine the best combination of flavors to provide the optimally flavored product for consumer demand and compliance. See, e.g., Roy et al., Modifying Bitterness: Mechanism, Ingredients, and Applications (1997).

Methods of Microencapsulation

The amino acid may be microencapsulated by methods known by one of ordinary skill in the art. Such known methods include, e.g., spray drying processes, spinning disk processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as dry granulation (i.e., roller compaction and slugging), extrusion/spheronization, or nano particle coating may also be used.

When microencapsulated, the amino acids can be present in particle sizes ranging from 1 micron to 1000 microns, 5 microns to 200 microns, or 10 microns to 100 microns.

Spray drying is often more readily available for scale-up to a commercial scale. In various embodiments, the material used in the spray-dry encapsulation process is emulsified or dispersed into the core material in a concentrated form, e.g., 10-60% solids. In some embodiments of the present invention, the solid loading is between about 10-20%, or between about 10-40%, or between about 40-60%. The microencapsulation material is, in one embodiment, is emulsified until about 1 to 3 μm droplets are obtained. In other embodiments, the microencapsulation material is emulsified until about 1 to 200 μm droplets are obtained, or until about 1 to 100 μm droplets are obtained. Once a dispersion of amino acid and encapsulation material are obtained, the emulsion is fed as droplets into the heated chamber of the spray drier. In some embodiments, the droplets are sprayed into the chamber or spun off a rotating disk. The microspheres are then dried in the heated chamber and fall to the bottom of the spray drying chamber where they are harvested.

Coacervation involves microencapsulation of materials such as active pharmaceutical ingredients and involves a three part process of particle or droplet formation, coascerate wall formation, and capsule isolation. This method can produce very small particle size microcapsules (10-70 microns).

Extrusion/spheronization is another method that involves wet massing of active pharmaceutical ingredients, followed by the extrusion of the wet mass through a perforated plate to produce short cylindrical rods. These rods are subsequently placed into a rapidly rotating spheronizer to shape the cylindrical rods into uniform spheres. The spheres are subsequently dried using a fluid bed drier and then coated with a functional coating using a fluid bed equipped with a Wurster insert and spray nozzle. This method produces smooth, uniform spheres that are ideal for receiving a functional coating. Drug loadings as high as 80% are possible (depending on drug characteristics).

Methods of Dry Coating

In addition to microencapsulation, the stability or release time of the amino acids used in the present invention may be increased by alternative methods such as dry coating and nano-particle coating. Dry coating involves the formation of granules of coated amino acid which are then mixed with other components. Dry granulation is achieved by forming dense compacts which are subsequently milled to a desired particle size and then blended with other components of the pharmaceutical composition. Dry granulation and nano-particle coating can provide enhanced stability and taste masking characteristics to active pharmaceutical by diluting and isolating such components in a granulated matrix of compatible ingredients that can enhance the shelf life of amino acid products as well as taste mask the bitterness if sweetener or flavors are used in coating material.

Typical technique for dry granulation is to use slugging or roller compaction. During slugging process, the dry powders are compressed using a conventional tablet machine, or more usually, a large heavy duty rotary press. The resulting compacts or "slug" are then milled to a desired particle size. Roller compaction is an alternative gentler method; the powder mix being squeezed between two rollers to form a compressed sheet. The sheet normally is weak and brittle and breaks immediately into flakes. These flakes need gentler treatment to break them into granules, and this can be usually be achieved by screening alone. Parikh, D. M., Handbook of Pharmaceutical Granulation Technology, (Marcel Dekker ed. 1997).

Additional Ingredients

Other ingredients can also be incorporated into the formulations of the present invention, including vitamins, minerals, fats, fatty acids such as DHA, EPA and ARA (arachidonic acid), carbohydrates, and other compounds, preferably in therapeutically effective amounts. Suitable minerals include, for example, calcium, chloride, chromium, copper, fluoride, iodine, iron, magnesium, manganese, molybdenum, phosphorus, potassium, selenium, sulfur, sodium, and zinc. Examples of suitable vitamins include Vitamin A (Retinol, retinyl acetate and palmitate, beta-carotene), Thiamin (vitamin B1), Riboflavin (vitamin B2), Niacin (vitamin B3, nicotinic acid), Panthenoic Acid (vitamin B5), Vitamin B6 (pyridoxine), Vitamin B12 (cobalamin), Biotin, Vitamin C (ascorbic acid), Vitamin D (calciferol), Vitamin E (alpha-tocopherol), Folic Acid (folate), and Vitamin K (phylloquinone, menaquinone).

In one embodiment, the formulation comprises one or more, five or more, 10 or more, or all of the following nutrients in addition to the amino acids present in the formulation, in therapeutically effective amounts: choline, inositol, vitamin A, vitamin D, vitamin E, vitamin K, vitamin C, thiamin, riboflavin, niacin, vitamin B6, folate, vitamin B12, biotin, pantothenic acid, potassium, calcium, magnesium, iron, zinc, copper, manganese, selenium, chromium, molybdenum, iodine, sodium, phosphorus, chloride, docosahexaenoic acid, arachidonic acid and lutein.

Of course, it will be understood that any of the foregoing nutrients can be present in a form well known to workers of ordinary skill in the art that provides similar nutritive value, such as salts and chelates and esters and other derivatives of the foregoing nutrients. Table H describes an example of various nutrients, effective nutrient doses, and nutrient derivates capable of incorporation into the formulations of the present invention. The formulation can include any one or combination of these nutrients.

TABLE H

|  | Substance | 1-3 years gr/day | 3-16 years gr/day | over 16 years gr/day |
|---|---|---|---|---|
| Vitamin | vitamin A | 0.00040000 | 0.00065000 | 0.00072000 |
|  | vitamin D | 0.00003200 | 0.00003250 | 0.00003600 |
|  | vitamin E | 0.00360000 | 0.00975000 | 0.02070000 |
|  | vitamin K | 0.00008000 | 0.00032500 | 0.00045000 |
|  | vitamin C | 0.04000000 | 0.07150000 | 0.13500000 |
|  | thiamin | 0.00060000 | 0.00104000 | 0.00135000 |
|  | riboflavin | 0.00060000 | 0.00195000 | 0.00270000 |
|  | niacin | 0.00720000 | 0.01300000 | 0.01800000 |
|  | vitamin B6 | 0.00040000 | 0.00227500 | 0.00135000 |
|  | folate | 0.00012000 | 0.00013000 | 0.00036000 |
|  | vitamin B12 | 0.00000600 | 0.00005200 | 0.00005400 |
|  | biotin | 0.00060000 | 0.00260000 | 0.00315000 |
|  | pantothenic acid | 0.00400000 | 0.02275000 | 0.02700000 |
| Mineral | potassium | 0.16000000 | 0.78000000 | 0.90000000 |
|  | calcium | 0.50000000 | 0.97500000 | 0.76500000 |
|  | magnesium | 0.06000000 | 0.22750000 | 0.19800000 |
|  | iron | 0.01100000 | 0.01625000 | 0.01350000 |
|  | zinc | 0.00320000 | 0.01040000 | 0.01710000 |
|  | copper | 0.00060000 | 0.00084500 | 0.00090000 |
|  | manganese | 0.00040000 | 0.00182000 | 0.00252000 |
|  | selenium | 0.00001400 | 0.00003250 | 0.00009000 |
|  | chromium | 0.00000400 | 0.00003250 | 0.00006300 |
|  | molybdenum | 0.00000200 | 0.00006500 | 0.00007200 |
|  | iodine | 0.00008000 | 0.00011050 | 0.00015300 |
|  | sodium | 0.03600000 | 0.00000000 | 0.00000000 |
|  | phosphorus | 0.20000000 | 0.78000000 | 0.63000000 |
|  | chloride | 0.08000000 | 0.00000000 | 0.00000000 |

TABLE H-continued

|  | Substance | 1-3 years gr/day | 3-16 years gr/day | over 16 years gr/day |
|---|---|---|---|---|
| Other nutrients | DHA docosahexaenoic acid | 0.08000000 | 0.26000000 | 0.27000000 |
|  | ARA arachidonic acid | 0.15000000 | 0.00000000 | 0.00000000 |
|  | Lutein | 0.00600000 | 0.00000000 | 0.00000000 |
|  | coline | 0.07000000 | 0.14950000 | 0.18000000 |
|  | inositol | 0.06000000 | 0.07800000 | 0.09000000 |

Final Formulation

In a particularly preferred embodiment the formulation comprises granulates of amino acids coated by one or release modifying excipients, also referred to herein as "coating means for retarding the amino acid release rate," or "coating means for achieving the recited release rate." The granulates can be made by wet or dry granulation techniques, as discussed above, but they are preferably made by wet granulation. They are also preferably confined to a particular size range, such as 0.1-3 mm, 0.5-2.0 mm, 0.5-1.0 mm, 0.5-2.0 mm, or 1.0-2.0 mm. Each amino acid can be contained within its own granulate, but the modified release amino acids are preferably mixed within the granulates.

The modified release properties are preferably achieved with a suitable release modifying coating or coatings applied to the granulate, in an amount of from 1 wt % to 30 wt %, or from 5 wt % to 25 wt % based on the weight of the amino acids. Suitable release retarding excipients for the coating are described elsewhere in this document, but one preferred composition comprises a coating of from 1 wt % ro 15 wt %, from 2 wt % to 10 wt %, or from 5 wt % to 7.5 wt % ethylcellulose based on the weight of the amino acids. Another preferred composition comprises a first coating of ethylcellulose (as described above) and a second coating of from 5% to 15% or about 10 wt. % glyceryl dibehenate based on the weight of the amino acids.

EXAMPLES

The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for.

Example 1—Exemplary Amino Acid Mixtures for Phenylketonuria

Table 1 lists three separate representative amino acid mixtures for the dietary management of phenylketonuria, on a percentage basis.

TABLE 1

|  | A | B | C |
|---|---|---|---|
| Essential Amino Acids | | | |
| L-Isoleucine | 5.11 | 7.18 | 5.11 |
| L-Leucine | 9.18 | 12.90 | 9.18 |
| L-Lysine HCL | 7.39 | 10.39 | 5.91[1] |
| L-Threonine | 3.8 | 5.34 | 5.28 |
| L-Tryptophan | 1.68 | 2.36 | 1.68 |
| L-Valine | 6.39 | 8.98 | 6.39 |
| L-Methionine | 2.04 | 2.86 | 2.04 |
| L-Histidine HCl | 3.04 | 2.358 | 3.04[1] |
| L-Arginine | 6.14 | 4.764 | 6.14 |
| Total Ess AA | 41.70 | 54.764 | 44.77 |
| Non-Essential Amino Acids | | | |
| L-Alanine | 6.0 | 4.665 | 6.0 |
| L-Aspartic Acid | 9.18 | 7.122 | 9.20 |
| L-Cystine | 2.03 | 1.57 | 2.03 |
| L-Glutamine | 12.49 | 9.691 | 12.49 |
| Glycine | 4.48 | 3.47 | 4.48 |
| L-Proline | 7.21 | 5.594 | 7.21 |
| L-Serine | 5.9 | 4.57 | 5.9 |
| Taurine | 0.300 | 0.232 | 0.25 |
| L-Tyrosine | 7.51 | 5.82 | 7.51 |
| L-Carnitine | 0.16 | 0.124 | 0.16 |
| Total Non-Ess AA | 58.30 | 45.236 | 55.23 |
| Total AA | 100 | 100 | 100 |

[1]weights based on the free base

Example 2—Exemplary Powder Formulations and Manufacturing Process

The following table describes formulations of five separate products containing 18 amino acids (excluding Methionine) using Plasdone K26/32 as a binding agent and a taste masking agent (Products 2, 3, 4, and 5). The reference formulation (Product 1) is without Plasdone K26/32 and without flavors.

TABLE 2a

Composition of Products 1, 2, 3, 4 and 5

| Component | Product 1 g | Product 2 g | Product 3 g | Product 4 g | Product 5 g |
|---|---|---|---|---|---|
| L-Alanine | 5.240 | 5.240 | 5.240 | 5.240 | 5.240 |
| L-Arginine | 6.140 | 6.140 | 6.140 | 6.140 | 6.140 |
| L-Aspartic Acid | 9.180 | 9.180 | 9.180 | 9.180 | 9.180 |
| L-Cystine | 2.030 | 2.030 | 2.030 | 2.030 | 2.030 |
| L-Glutamine | 12.490 | 12.490 | 12.490 | 12.490 | 12.490 |
| Glycine | 4.480 | 4.480 | 4.480 | 4.480 | 4.480 |
| L-Histidine HCl | 3.040 | 3.040 | 3.040 | 3.040 | 3.040 |
| L-Isoleucine | 5.110 | 5.110 | 5.110 | 5.110 | 5.110 |
| L-Leucine | 9.180 | 9.180 | 9.180 | 9.180 | 9.180 |
| L-Lysine HCL | 7.390 | 7.390 | 7.390 | 7.390 | 7.390 |
| L-Proline | 7.210 | 7.210 | 7.210 | 7.210 | 7.210 |
| L-Serine | 5.900 | 5.900 | 5.900 | 5.900 | 5.900 |
| Taurine | 0.188 | 0.188 | 0.188 | 0.188 | 0.188 |
| L-Threonine | 4.540 | 4.540 | 4.540 | 4.540 | 4.540 |
| L-Tryptophan | 1.680 | 1.680 | 1.680 | 1.680 | 1.680 |
| L-Tyrosine | 7.510 | 7.510 | 7.510 | 7.510 | 7.510 |
| L-Valine | 6.360 | 6.360 | 6.360 | 6.360 | 6.360 |
| L-Carnitine | 0.116 | 0.116 | 0.116 | 0.116 | 0.116 |
| Sum | 97.784 | 97.784 | 97.784 | 97.784 | 97.784 |
| Plasdone K26/32 | 0.000 | 1.000 | 1.000 | 1.000 | 1.000 |
| Flavor[1] | 0.000 | 0.000 | 1.250 | 1.400 | 1.500 |

[1]Product 1 no Flavor; Product 2 no Flavor; Product 3 Caramel Flavor; Product 4 Vanilla Flavor; Product 5 Banana Flavor Each of the formulations was manufactured according to the following general method.

Step 1
Manufacturing Equipment:
  Balances of various types
  High share mixer: Diosna Laboratory mixer P1/6
  Sieves
  Static oven
  Mixing machine
Mixture of Amino Acids Product 1
  Accurately weigh the amino acids and mix for 20 minutes with the mixing machine.
Granulate preparation without flavor Product 2
  Accurately weigh the amino acids and mix for 20 minutes with the mixing machine. Transfer the mix to the Diosna, and mix for 1 minutes at a blade speed of 250 rpm. Wet the mixture with an alcoholic solution of Plasdone K26/32 (10% in ethanol solution-10 g for 100 g of Ethanol). After one minute and 30 seconds, add the solution and granulate and mix for three minutes at a blade speed of 250 rpm and a chopper speed of 500 rpm. Discharge the granulate and pass through a sieve with a width of 0.8 mm. Dry in a static oven for about four hours at 40° C. Discharge and pass again through a sieve with a width of 0.8 mm.
Granulate Preparation with Flavor Products 3, 4 and 5
  Weigh accurately the amino acids and mix for 20 minutes with the mixing machine. Transfer the mixture to the Diosna, and mix for 1 minute and 30 seconds at a blade speed of 250 rpm. Wet the mixture with an alcoholic solution of Plasdone K26/32 (10% content in ethanol solution—10 g for 100 g of AA) and flavor. The quantity of flavors added to the alcoholic solution of Plasdone K26/32 are the following:
  1.13 g of 58% content of Caramel in Ethanol (for Product 3)
  1.13 g of 60% content of Vanilla in Ethanol (for Product 4)
  1.46 g of 14% content of Banana in Ethanol (for Product 5)
After one minute and 30 seconds mix the solution and granulate for three minutes at a blade speed of 250 rpm and a chopper speed of 500 rpm. Discharge the granulate and pass through a sieve with a width of 0.8 mm. Dry in a static oven for about four hours at 40° C. Discharge and pass the mixture through a sieve with a width of 0.8 mm.

Step 2
  Preparation of Methionine using a Plasdone K26/32 as binding agent and taste masking agent plus a very small quantity of Caramel flavor using a manufacturing method similar to the method used for Products 3, 4 and 5 reported in step 1.

TABLE 2b

Composition of granulate L-Methionine Product 6

| Component | Product 6 g |
|---|---|
| L-Methionine[1] | 250.0 |
| Plasdone K26/32[2] | 30 |
| Flavor Caramel[3] | 3.6 |
| Sum | 289 |

[1]100 g of L-Methionine corresponds to 103.2 g of L-Methionine granulate
[2]Plasdone K26/32 20% in Ethanol solution: 30 g corresponds to 6 g of Plasdone K29/32
[3]Caramel in 58% ethanol solution: 3.6 g correspond to 2.088 g of pure Caramel Step 3
  Preparation of the final formulation mixing the powder/granulates of Step 1 plus the granulate of Step 2 in the quantity below reported.

TABLE 2c

Composition of final formulation of Products 7, 8, 9, 10 and 11

| Component | Product 7 g | Product 8 g | Product 9 g | Product 10 g | Product 11 g |
|---|---|---|---|---|---|
| L-Alanine | 5.240 | 5.240 | 5.240 | 5.240 | 5.240 |
| L-Arginine | 6.140 | 6.140 | 6.140 | 6.140 | 6.140 |
| L-Aspartic Acid | 9.180 | 9.180 | 9.180 | 9.180 | 9.180 |
| L-Cystine | 2.030 | 2.030 | 2.030 | 2.030 | 2.030 |
| L-Glutamine | 12.490 | 12.490 | 12.490 | 12.490 | 12.490 |
| Glycine | 4.480 | 4.480 | 4.480 | 4.480 | 4.480 |
| L-Histidine HCl | 3.040 | 3.040 | 3.040 | 3.040 | 3.040 |
| L-Isoleucine | 5.110 | 5.110 | 5.110 | 5.110 | 5.110 |
| L-Leucine | 9.180 | 9.180 | 9.180 | 9.180 | 9.180 |
| L-Lysine HCL | 7.390 | 7.390 | 7.390 | 7.390 | 7.390 |
| L-Proline | 7.210 | 7.210 | 7.210 | 7.210 | 7.210 |
| L-Serine | 5.900 | 5.900 | 5.900 | 5.900 | 5.900 |
| Taurine | 0.188 | 0.188 | 0.188 | 0.188 | 0.188 |
| L-Threonine | 4.540 | 4.540 | 4.540 | 4.540 | 4.540 |
| L-Tryptophan | 1.680 | 1.680 | 1.680 | 1.680 | 1.680 |
| L-Tyrosine | 7.510 | 7.510 | 7.510 | 7.510 | 7.510 |
| L-Valine | 6.360 | 6.360 | 6.360 | 6.360 | 6.360 |
| L-Carnitine | 0.116 | 0.116 | 0.116 | 0.116 | 0.116 |
| L-Methionine[1] | 2.115 | 2.115 | 2.115 | 2.115 | 2.115 |
| Sum AA | 99.899 | 99.899 | 99.899 | 99.899 | 99.899 |
| Plasdone K26/32 | 0.050 | 1.050 | 1.050 | 1.050 | 1.050 |
| Flavor[2] | 0.000 | 0.000 | 1.250 | 1.400 | 1.500 |

[1]2.115 g of granulate L-Methionine in Product 7 corresponding to 2.050 g of Methionine
[2]Product 7 no Flavor (only a small quantity of caramel deriving from Methionine powder), Product 8 no Flavor (only a small quantity of caramel deriving from Methionine powder), Product 9 Caramel Flavor, Product 10 Caramel and Vanilla Flavor, Product 11 Caramel and Banana Flavor All the above mentioned Products were manufactured by mixing the powder or granulates of Products 2, 3, 4 and 5 with the granulate of Product 6.

Example 3—Taste Testing

On the final formulations reported in Example 2 (Products 8, 9, 10 and 11), the following trial was performed in 6 healthy adults. The results reported are average values:

TABLE 3

Results of Taste Testing

| | Reference Marketed Product | Product 8 | Product 9 | Product 10 | Product 11 |
|---|---|---|---|---|---|
| Product in Yogurt with banana flavor: | | | | | |
| ODOR | 4.25 | 4.6 | — | — | — |
| TASTE | 3.75 | 4.6 | — | — | — |
| Persistency (bad taste in the mouth) | 3 | 2.2 | — | — | — |
| Product in Orange juice: | | | | | |
| ODOR | 4 | 5 | — | — | — |
| TASTE | 3.25 | 4.125 | — | — | — |
| Persistency (bad taste in the mouth) | 2.5 | 1.75 | — | — | — |

TABLE 3-continued

Results of Taste Testing

| | Reference Marketed Product | Product 8 | Product 9 | Product 10 | Product 11 |
|---|---|---|---|---|---|
| Product in pressed Banana | | | | | |
| ODOR | 3.5 | 5 | — | — | — |
| TASTE | 1 | 4.375 | — | — | — |
| Persistency (bad taste in the mouth) | 2.75 | 2.25 | — | — | — |
| Product dispersed in Water: | | | | | |
| ODOR | 2.4 | — | 4.3 | 4.8 | 4.3 |
| TASTE | 0.8 | — | 3.9 | 3.5 | 5 |
| Persistency (bad taste in the mouth) | 4.6 | — | 2.4 | 2 | 1.4 |
| Dispersibility | 2 | 4 | 4 | 4 | 4 |

Legend:
Odor/Taste: 0 = bad 5 = good
Persistency (bad taste in the mouth): 0 = low persistency 5 = long persistency
Dispersability: 0 = bad 5 = good As the foregoing data shows, the formulations of the present invention are better than the Reference Marketed Product and better than the formulation without Plasdone K26/32 in terms of dispersability and taste.

Example 4—Exemplary Biscuit Formulations and Manufacturing Process

Several biscuit formulations were prepared starting with similar granulate Products to those reported in Example 2 (changing slightly the amounts of flavors).

TABLE 4a

| Component | Product 1 g | Product 2 g | Product 3 g |
|---|---|---|---|
| L-Alanine | 5.240 | 5.240 | 5.240 |
| L-Arginine | 6.140 | 6.140 | 6.140 |
| L-Aspartic Acid | 9.180 | 9.180 | 9.180 |
| L-Cystine | 2.030 | 2.030 | 2.030 |
| L-Glutamine | 12.490 | 12.490 | 12.490 |
| Glycine | 4.480 | 4.480 | 4.480 |
| L-Histidine HCl | 3.040 | 3.040 | 3.040 |
| L-Isoleucine | 5.110 | 5.110 | 5.110 |
| L-Leucine | 9.180 | 9.180 | 9.180 |
| L-Lysine HCL | 7.390 | 7.390 | 7.390 |
| L-Proline | 7.210 | 7.210 | 7.210 |
| L-Serine | 5.900 | 5.900 | 5.900 |
| Taurine | 0.188 | 0.188 | 0.188 |
| L-Threonine | 4.540 | 4.540 | 4.540 |
| L-Tryptophan | 1.680 | 1.680 | 1.680 |
| L-Tyrosine | 7.510 | 7.510 | 7.510 |
| L-Valine | 6.360 | 6.360 | 6.360 |
| L-Carnitine | 0.116 | 0.116 | 0.116 |
| L-Methionine[1] | 2.115 | 2.115 | 2.115 |
| Sum | 99.899 | 99.899 | 99.899 |
| Plasdone K26/32 | 1.050 | 1.050 | 1.050 |
| Flavor[2] | 0.986 | 1.02 | 0.306 |

[1]2.115 g of granulate L-Methionine corresponding to 2,050 g of Methionine
2Product 1 Caramel Flavor, Product 2 Vanilla Flavor, Product 3 Banana Flavor To the above mentioned Products were added saccharose, silicon dioxide and glyceryl dibehenate through a simple mixing procedure. The final formulations were as follows:

TABLE 4b

| Component | Product 4[1] g | Product 5[1] g | Product 6[1] g |
|---|---|---|---|
| L-Alanine | 5.240 | 5.240 | 5.240 |
| L-Arginine | 6.140 | 6.140 | 6.140 |
| L-Aspartic Acid | 9.180 | 9.180 | 9.180 |
| L-Cystine | 2.030 | 2.030 | 2.030 |
| L-Glutamine | 12.490 | 12.490 | 12.490 |
| Glycine | 4.480 | 4.480 | 4.480 |
| L-Histidine HCl | 3.040 | 3.040 | 3.040 |
| L-Isoleucine | 5.110 | 5.110 | 5.110 |
| L-Leucine | 9.180 | 9.180 | 9.180 |
| L-Lysine HCL | 7.390 | 7.390 | 7.390 |
| L-Proline | 7.210 | 7.210 | 7.210 |
| L-Serine | 5.900 | 5.900 | 5.900 |
| Taurine | 0.188 | 0.188 | 0.188 |
| L-Threonine | 4.540 | 4.540 | 4.540 |
| L-Tryptophan | 1.680 | 1.680 | 1.680 |
| L-Tyrosine | 7.510 | 7.510 | 7.510 |
| L-Valine | 6.360 | 6.360 | 6.360 |
| L-Carnitine | 0.116 | 0.116 | 0.116 |
| L-Methionine[2] | 2.115 | 2.115 | 2.115 |
| Sum | 99.899 | 99.899 | 99.899 |
| Plasdone K26/32 | 1.050 | 1.050 | 1.050 |
| Flavor | 0.986 | 1.02 | 0.306 |
| Saccharose | 50.000 | 50.000 | 50.000 |
| Glyceryl di-behenate | 1.500 | 1.500 | 1.500 |

[1]Product 4 Caramel Flavor, Product 5 Vanilla Flavor, Product 6 Banana Flavor
[2]2.115 g of granulate L-Methionine corresponding to 2.050 g of Methionine Tablets were prepared using a mono-punch tableting machine with an average weight between 5.5 and 6.2 g. To correct some sticking problems in the punch, a new formulation starting from Product 1 was prepared:

TABLE 4c

| Component | Product 7 g |
|---|---|
| L-Alanine | 5.240 |
| L-Arginine | 6.140 |
| L-Aspartic Acid | 9.180 |
| L-Cystine | 2.030 |
| L-Glutamine | 12.490 |
| Glycine | 4.480 |
| L-Histidine HCl | 3.040 |
| L-Isoleucine | 5.110 |
| L-Leucine | 9.180 |
| L-Lysine HCL | 7.390 |
| L-Proline | 7.210 |
| L-Serine | 5.900 |
| Taurine | 0.188 |
| L-Threonine | 4.540 |
| L-Tryptophan | 1.680 |
| L-Tyrosine | 7.510 |
| L-Valine | 6.360 |
| L-Carnitine | 0.116 |
| L-Methionine[1] | 2.115 |
| Sum | 99.899 |
| Polyvinylpyrrolidone | 1.050 |
| Flavor Caramel | 0.986 |
| Comprizuker | 50.000 |
| Silicon dioxide | 2.500 |
| Glyceryl di-behenate | 2.500 |

[1]2.115 g of granulate L-Methionine correspond to 2,050 g of Methionine

Example 5—Taste Trial of Biscuit Formulation

Products 4, 5 and 6 reported in Example 4 were tested for odor and taste on 6 healthy adults. The results reported are average values.

TABLE 5

|  | Flavor Product 4 | Flavor Product 5 | Flavor Product 6 |
|---|---|---|---|
| Odor | 4.6 | 3.8 | 4.8 |
| Taste | 4.4 | 3.8 | 3.6 |
| Persistency (bad taste in the mouth) | 2.6 | 3.2 | 3.2 |

Legend:
Odor-Taste-Vista: 0 = bad 5 = good
Persistency (bad taste in mouth): 0 = low persistency 5 = long persistency
Dispersability: 0 = bad 5 = good

Example 6—Preparation of Modified Release Formulations

Mixing Preparation

Weigh and sieve each individual amino acid, diluent (if used) and HPMC and mix for 20 minutes in an appropriate mixing machine.

Granulate Preparation without Flavor

Transfer the mix to the Diosna mixer, mixing for 1 minute with blade speed set at 250 rpm. Wet the mix with an alcoholic solution of EC (15% content). After one minute and 30 seconds add the solution and granulate for three minutes with a blade speed at 250 rpm and chopper speed at 500 rpm. Discharge the granulate and pass through a sieve with a width of 0.63 mm. Dry in a static oven for about four hours at 45° C. Discharge and pass through a sieve with a width of 0.8 mm.

It is also possible to process 4-5 amino acids into granulates at a time, and mix all of the amino acids granulates together to make the final product. Some examples of potential formulations are reported in Example 1 Table 1.

Example 7—Modified Release Formulation

The following formula was prepared to determine the quantity of hydroxypropyl-methylcellulose (HPMC) and ethyl cellulose (EC) needed to modify the release of tryptophan in a Dissolution Test.

TABLE 6

| Composition of Product | |
|---|---|
| Component | g |
| L-Isoleucine | 14 |
| L-Lysine HCL | 20 |
| L-Threonine | 12 |
| L-Tryptophan | 4 |
| Mannitol | 10 |
| HPMC (Methocel 4KM) | 5 |
| Solution of EC at 15% in EtOH | 19.5[1] |

[1]corresponding to 3 g of EC

Mixing Preparation

Weigh and sieve the single amino acids, mannitol and HPMC and mix for 20 minutes in an appropriate container with the mixing machine.

Granulate Preparation without Flavor

Transfer the mixture to the Diosna mixer, mixing for 1 minute with the blade speed at 250 rpm. Wet the mix with an alcoholic solution of EC (ethyl cellulose) (15% content). After one minute and 30 seconds add the solution and granulate for three minutes with the blade speed at 250 rpm and the chopper speed at 500 rpm. Discharge the granulate and pass through a sieve with a width of 0.63 mm. Dry in a static oven for about four hours at 45° C. Discharge and pass through a sieve with a width of 0.8 mm.

Figure 3:
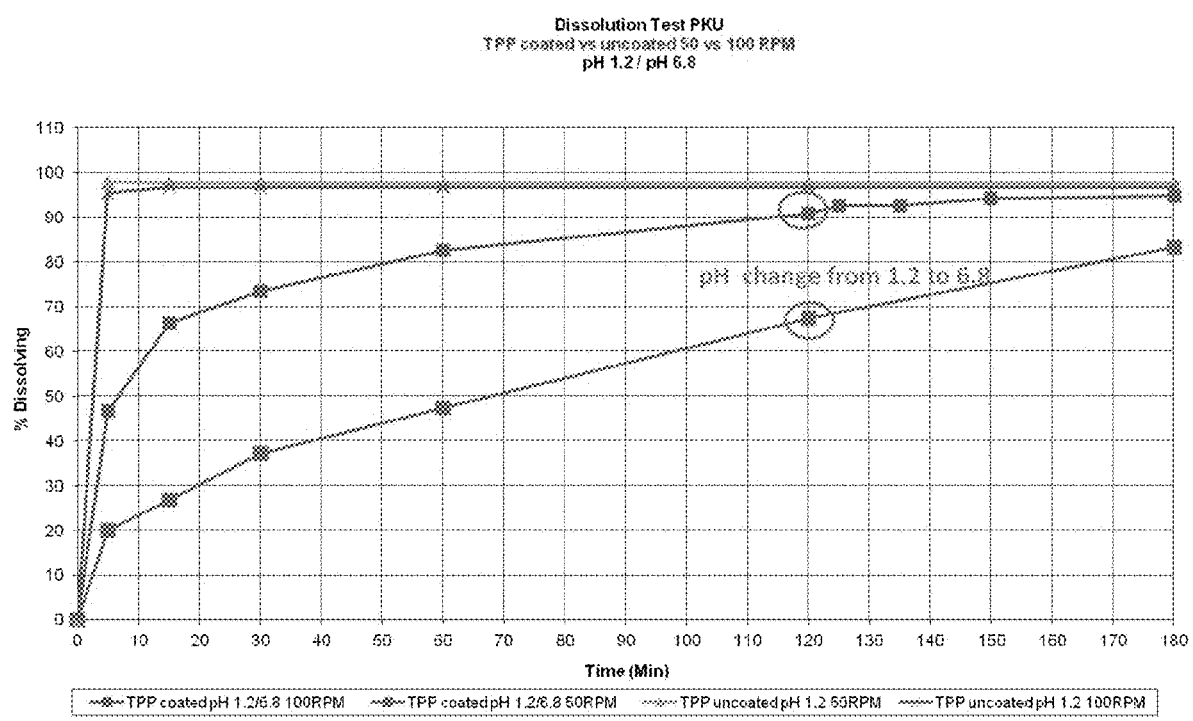
FIG. 3 is a graphical depiction of the release profile over time of uncoated tryptophan made according to the method of Example 7, using two different paddle speeds, as compared to tryptophan formulated in accordance with the present invention.

The formulation was evaluated under the dissolution conditions reported below to determine the release rate of tryptophan from the formulation (pH 1.2 for 2 hours, increased to pH 6.8 after 2 hours) in basket conditions at 50 and 100 rpm versus a simple mixture of uncoated AA. The results of the Dissolution Test are reported in FIG. 3. Analysis was performed by HPLC.

Dissolution Test Conditions
Apparatus: Paddle
Temperature: 37° C.±5° C.
Medium: 0.1 N Hydrochloric Acid
pH adjustment: 0.2 M solution of trisodium phosphate dodecahydrate. Volume medium:
   450 ml 0.1N HCl. After 120 minutes adjust dissolution medium to pH 6.8±0.05 (according to European Pharmacopoeia 2.9.3 Delayed-release solid dosage forms Method A).
Speed: 50 rpm or 100 rpm
Sampling Time: 5 and 15 minutes for uncoated formulation
   5, 15, 30, 60, 120, 125, 135, 150, 180 minutes for coated formulation (after 120 minutes the pH of the medium was changed to pH 6.8)
Vessel concentration: about 90 µg/ml (a fraction of the powder of the retard formulation remains as surnactant during the dissolution test)

Example 8—Modified Release Formulation without Mannitol

Figure 4:
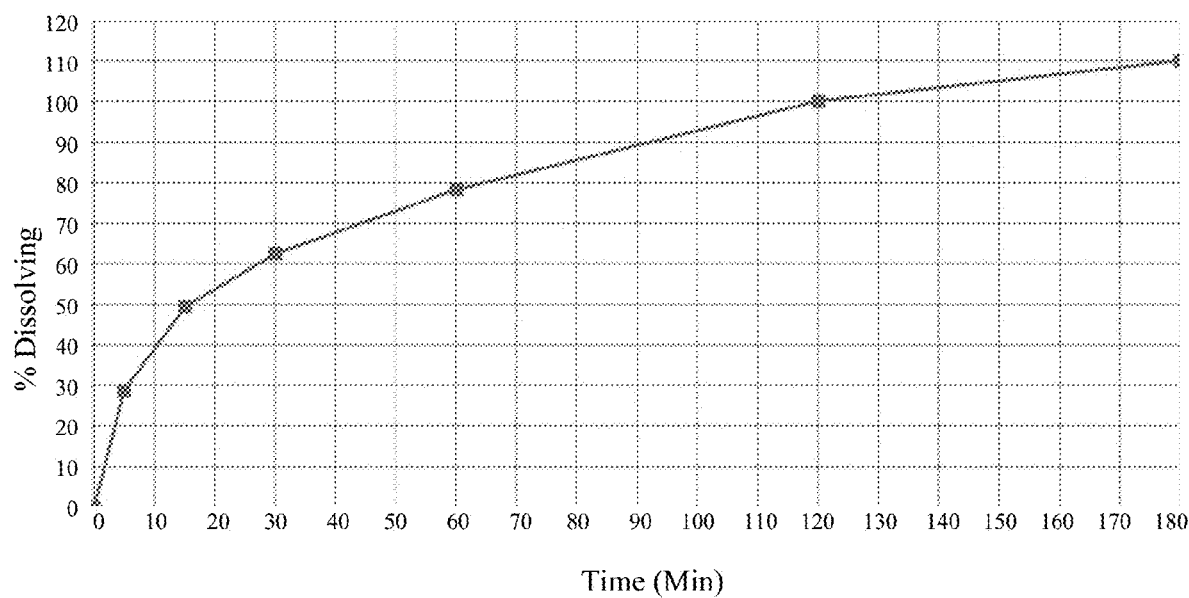
FIG. 4 is a graphical depiction of the release profile of tryptophan over time from the formulation of Example 8 using a dissolution media at pH 1.2 and a paddle speed of 50 rpm.

The following formulation was prepared in accordance with the procedures set forth in Example 7 and subjected to dissolution testing under the conditions reported below. The release rate of tryptophan from the formulation is depicted in FIG. 4. Analysis was performed by HPLC.

TABLE 7

| Composition of the Product | |
|---|---|
| Component | g |
| L-Isoleucine | 56 |
| L-Lysine HCL | 80 |
| L-Threonine | 48 |
| L-Tryptophan | 16 |
| HPMC (Methocel 4KM) | 20 |
| Solution of EC at 15% in ETOH | 80 |

Dissolution Test Conditions
Apparatus: Paddle
Temperature: 37° C.±5° C.
Medium: 0.1 N Hydrochloric Acid
Volume medium: 450 ml
Speed: 50 rpm
Sampling Times: 5', 15', 30', 60', 120', 180' Vessel concentration: about 90 µg/ml (a fraction of the powder of the retard formulation remains as surnactant during the dissolution test)

Example 9—Modified Release Formulation without Mannitol or HPMC (Methocel 4KM)

Figure 5:
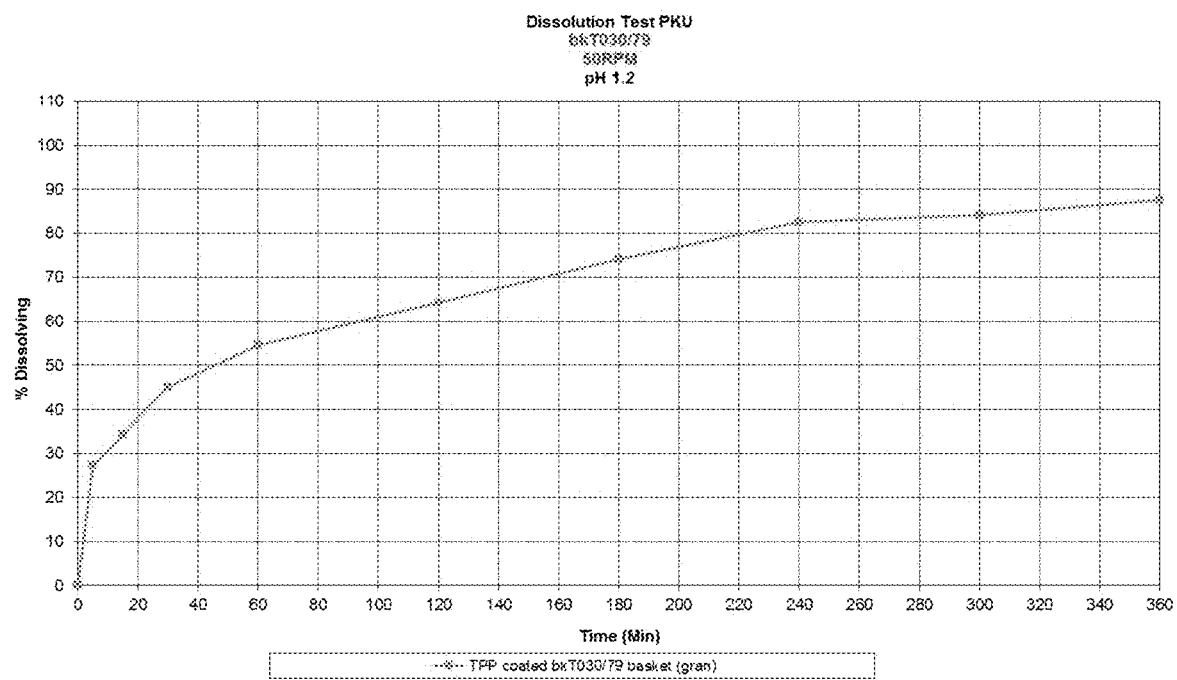
FIG. 5 is a graphical depiction of the release profile of tryptophan over time from the formulation of Example 9 when subjected to the experimental conditions described in Example 8 but using the basket method instead of the paddle.

The following formulation was prepared in accordance with the procedures set forth in Example 7 and subjected to dissolution testing under the conditions reported below. The release rate of tryptophan from the formulation is depicted in FIG. 5. Analysis was performed by HPLC.

TABLE 8

Composition of the Product

| Component | g |
|---|---|
| L-Isoleucine | 56.0 |
| L-Lysine | 80.0 |
| L-Treonine | 48.0 |
| L-Tryptophan | 16.0 |
| Ethylcellulose[1] | 10.0 |
| Total | 210 g |

[1]corresponding to 67 g of an ethanol solution of Ethylcellulose at 15%

Mixing Preparation

Weigh and sieve the single amino acids and mix for 20 minutes in an appropriate container with the mixing machine.

Granulate Preparation without Flavor

Transfer the mixture to the Diosna mixer, mixing for 1 minute with the blade speed at 250 rpm. Wet the mix with an alcoholic solution of EC (ethyl cellulose) (15% content). After one minute and 30 seconds add the solution and granulate for three minutes with the blade speed at 500 rpm and the chopper speed at 1500 rpm. Discharge the granulate and pass through a sieve with a width of 0.8 mm. Dry in a static oven for about 5 hours and 30 minutes at 45° C. Discharge and pass through a sieve with a width of 1.4 mm.

The formulation was evaluated under the dissolution conditions reported below to determine the release rate of tryptophan from the formulation (pH 1.2) in basket conditions at 50 rpm. The results of the dissolution test are reported in FIG. 5.

Dissolution Test Conditions
Apparatus: Basket
Temperature: 37° C.±5° C.
Medium: 0.1 N Hydrochloric Acid
Volume medium: 450 ml
Speed: 50 rpm
Sampling Times: 5', 15', 30', 60', 120', 180', 240', 300' and 360'
Vessel concentration: about 90 µg/ml (a fraction of the powder of the retard formulation remains as surnactant during the dissolution test)

Example 10—Modified Release Formulation on 19 Amino Acids Coated with Ethylcellulose and Glyceryl dibehenate The following formulation was prepared in accordance with the procedures described below.

TABLE 9

Composition of the Product

| Component | Final mix (g) | Final mix (%) |
|---|---|---|
| L-Isoleucine | 3.20 | 4.18 |
| L-Lysine HCl | 4.63 | 6.05[1] |
| L-Treonine | 3.31 | 4.33 |
| L-Tryptophan | 1.05 | 1.37 |
| L-Leucine | 5.75 | 7.52 |
| L-Valine | 4.00 | 5.23 |
| L-Methionine | 1.28 | 1.67 |
| L-Cystine | 1.27 | 1.66 |
| L-Glutamine | 7.82 | 10.22 |
| L-Histidine HCl | 2.35 | 3.07[2] |
| L-Alanine | 3.76 | 4.91 |
| L-Arginine | 3.84 | 5.02 |

TABLE 9-continued

Composition of the Product

| Component | Final mix (g) | Final mix (%) |
|---|---|---|
| L-Serine | 3.69 | 4.82 |
| Glicine | 2.81 | 3.67 |
| Proline | 4.52 | 5.91 |
| L-Aspartic Acid | 5.76 | 7.53 |
| Taurine | 0.16 | 0.21 |
| L-Tyrosine | 4.70 | 6.14 |
| L-Carnitine | 0.10 | 0.13 |
| Glyceryl Dibehenate | 9.12 | 11.92 |
| Sodium Alginate | 0.02 | 0.03 |
| ethylcellulose | 3.37 | 4.40 |
| Total | 76.51 | 100.00[3] |

[1]corresponding to 4.84 g of L-Lysine base
[2]corresponding to 2.49 g of L-Histidine base
[3]corresponding to 98.21 g if L-Lysine and L-Histidine are considered as base Manufacturing Equipment Used for the Preparation of the Product Equipment used for the production:
Balances of various types
ProCepT Mipro 900 ml set-up
Sieves
Static oven
ProCepT Fluid bed bottom-up coating (melt nozzle) (or any other apparatus suitable for the granulate hot melt coating)

Amino Acids Mixture
Mix all amino acids in a suitable apparatus

Granulate Preparation
Transfer the amino acid mixture into the ProCepT Mipro, add the granulating solution composed of a 2% sodium alginate water solution and granulate. After the granulation sieve the granulate; use the fraction having 0.5 mm<PSD<1 mm for the next step.

Coating with Ethylcellulose (Polymer Coating)
Transfer the sieved fraction of granulate in the fluid bed apparatus and spray coat it with a methanol solution at 15% (w/w) of ethylcellulose. The total amount of polymer added should equal approximately 5.00% of the weight of the granulate.

Coating with Glyceryl Dibehenate (Hot Melt Coating)
Transfer the granulate coated with ethylcellulose in the fluid bed apparatus and spray coat it with melted glyceryl dibehenate. The total amount of polymer added should equal approximately 15.00% of the granulate weight.

Figure 6:
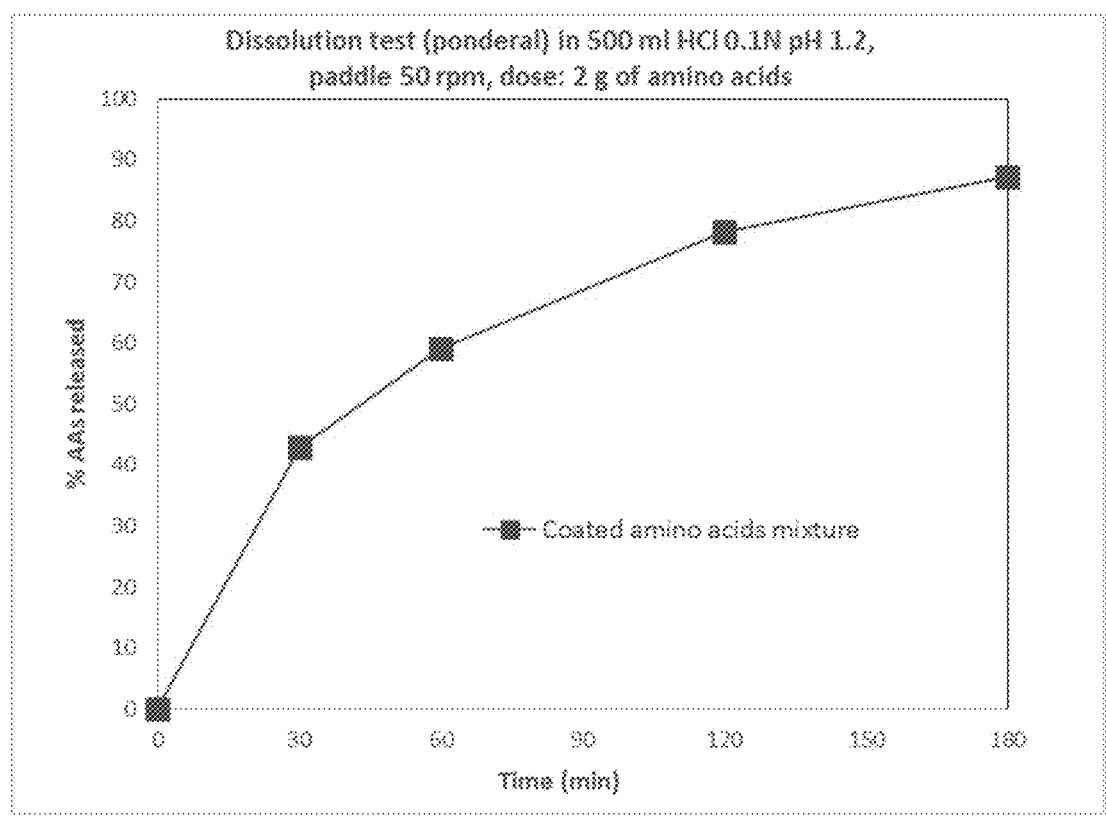
FIG. 6 is a graphical depiction of the ponderal release profiles of a formulation containing the amino acids mixture over time from the formulation of Example 10, when subjected to the experimental conditions described in Example 10.

Dissolution Test on the Product
Dissolution Medium: Medium pH 1.2±0.1 (0.1N Hydrochloric acid)
Apparatus: Paddle Apparatus (Apparatus 2, USP <711> modified); 50 rpm
Time: 30-60-120-180 minutes
Temperature: 37±0.5° C.
Volume Medium: 500 mL
Sample: 2.0 g of Amino Acid mixture
Ponderal dissolution test: 30-60-120-180 minutes The results of the Ponderal Dissolution Test takes into account that ethyl cellulose and glyceryl dibehenate are not soluble in HCl solution. At 30-60-120-180 minutes the dissolution medium were filtered through a paper filter under vacuum. The filtered powder and filter were dried for ±4 hours in a vacuum oven at 50° C. until constant weight achieved and the samples were the weighed. For difference the released quantity of amino acids was calculated and reported in FIG. 6.

Example 11—Manufacturing and Dissolution Testing of Free Amino Acid Formulation and Modified Release Formulations Table 10a reports the qualitative and quantitative composition of a representative amino acid formulation AA mixture (bkT037/71).

TABLE 10a

| Amino Acid | % (with HCl) | Amino Acid | % (As Base) |
|---|---|---|---|
| L-Alanine | 5.87 | L-Alanine | 5.87 |
| L-Arginine | 6.01 | L-Arginine | 6.01 |
| L-Cystine | 1.99 | L-Cystine | 1.99 |
| L-Glutamine | 12.22 | L-Glutamine | 12.22 |
| Glicine | 4.38 | Glicine | 4.38 |
| L-Histidine HCl | 3.67 | L-Histidine | 2.98 |
| L-Aspartic Acid | 9.00 | L-Aspartic Acid | 9.00 |
| L-Proline | 7.06 | L-Proline | 7.06 |
| L-Serine | 5.77 | L-Serine | 5.77 |
| Taurine | 0.24 | Taurine | 0.24 |
| L-Tyrosine | 7.35 | L-Tyrosine | 7.35 |
| L-Carnitine | 0.16 | L-Carnitine | 0.16 |
| L-Isoleucine | 5.00 | L-Isoleucine | 5.00 |
| L-Lysine HCl | 7.23 | L-Lysine | 5.78 |
| L-Treonine | 5.17 | L-Treonine | 5.17 |
| L-Tryptophan | 1.64 | L-Tryptophan | 1.64 |
| L-Leucine | 8.98 | L-Leucine | 8.98 |
| L-Valine | 6.25 | L-Valine | 6.25 |
| L-Methionine | 2.00 | L-Methionine | 2.00 |
| Total | 100 | Total | 97.86 |

Manufacturing Method (General)
Manufacturing Equipment Used for the Preparation of the Product
 Balances of various types
 Sieves
 Static oven
 Mixing machine
Sieve and mix all amino acids in a suitable apparatus
Amino Acids are mechanically passed through a 350 μm stainless sieve and mixed for 30 minutes in the mixer.
Dissolution Test on the Product
Dissolution Medium: Medium pH 1.2±0.1 (0.1N Hydrochloric acid)
Apparatus: Paddle Apparatus (Apparatus 2, USP <711> modified) 50 rpm
Time: 30-60 minutes
Temperature: 37±0.5° C.
Volume Medium: 500 mL
Sample: 2.0 g of Amino Acid mixture
Ponderal dissolution test: 30-60-120-180 minutes
Each time point has its own dissolution vessel. At 30-60-120-180 minutes the dissolution medium were filtered through a paper filter under vacuum. The filtered powder and filter were dried for ±4 hours in a vacuum oven at 50° C. until constant weight achieved and the samples were the weighed. For difference the released quantity of amino acids was calculated.

Results

Figure 7:
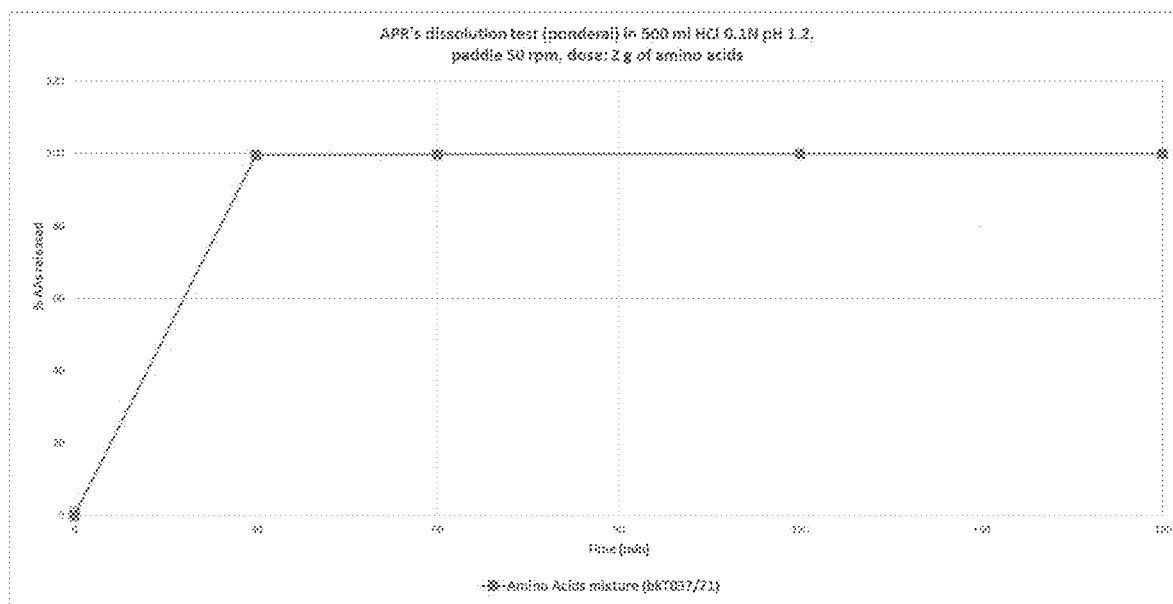
FIG. 7 is a graphical depiction of the ponderal dissolution profile of the free amino acid formulation described in Example 11, Table 10b, tested according to the methods described in Example 11.

The results of ponderal dissolution testing are report in Table 10b and FIG. 7.

TABLE 10b

| Time (min) | % AA released |
|---|---|
| 0 | 0 |
| 30 | 99.96 |
| 60 | 100.00 |
| 120 | 99.95 |
| 180 | 99.99 |

Analytical Conditions:
 HPLC: Agilent series 1200
 Detector: Fluorimeter Agilent series 1200
 Chromatographic Column: YMC-Triart C18 12 nm S (250×4.6 mm-5 μm)

Amino Acids are analyzed after extraction (with different ways) and derivatization with FMOC (9-Fluorenyl methyl chloroformate). Note: Carnitina is analyzed by LC/MS.

Figure 8:
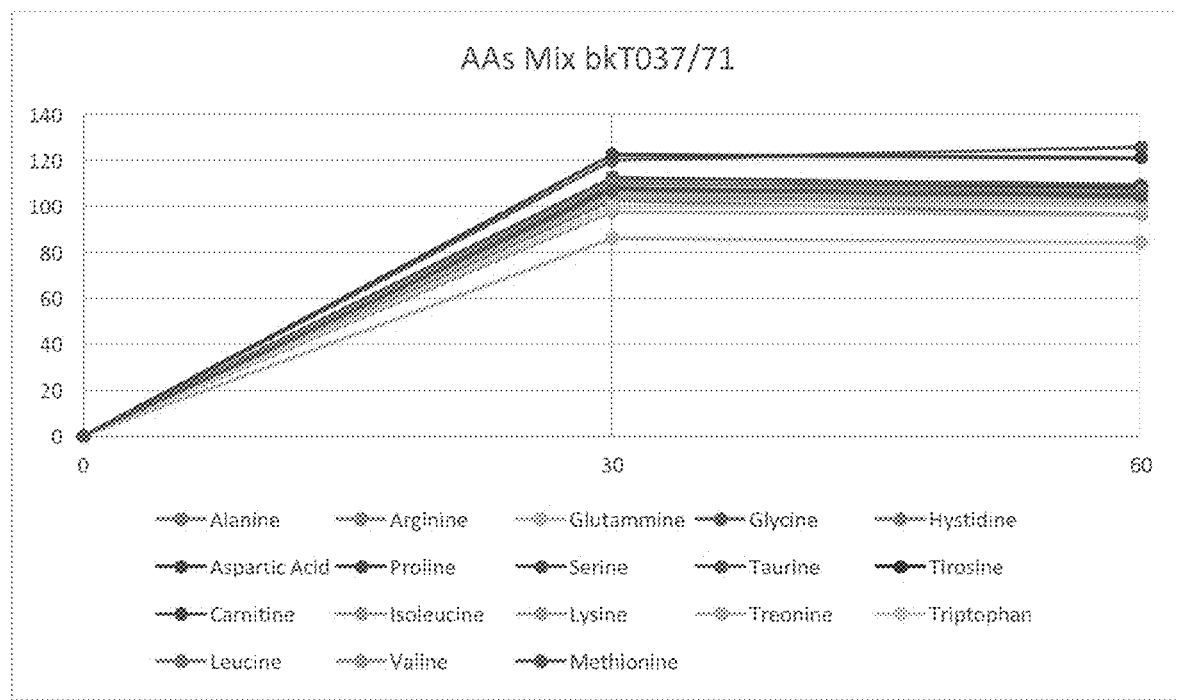
FIG. 8 plots the dissolution profile for the 18 separate amino acids from APR AA mix (bkT037/71)

The results of the dissolution testing for AA Mixture (bkT037/71) are reported in Table 10c and FIG. 8.

TABLE 10c

| Amino Acid | Time (min) 0 | 30 | 60 |
|---|---|---|---|
| Alanine | 0 | 111.8 | 109.0 |
| Arginine | 0 | 110.1 | 107.0 |
| Glutammine | 0 | 85.9 | 84.3 |
| Glycine | 0 | 112.6 | 109.4 |
| Hystidine | 0 | 102.7 | 96.3 |
| Aspartic Acid | 0 | 103.7 | 106.6 |
| Proline | 0 | 109.9 | 108.1 |
| Serine | 0 | 108.1 | 105.2 |
| Taurine | 0 | 120.0 | 125.8 |
| Tirosine | 0 | 103.9 | 101.2 |
| Carnitine | 0 | 122.5 | 121.3 |
| Isoleucine | 0 | 103.6 | 100.6 |
| Lysine | 0 | 103.8 | 101.6 |
| Treonine | 0 | 97.7 | 96.3 |
| Triptophan | 0 | 100.0 | 100.6 |
| Leucine | 0 | 110.1 | 106.6 |
| Valine | 0 | 105.4 | 103.4 |
| Methionine | 0 | 107.0 | 104.5 |

Table 10d reports the quantitative and qualitative formulations of four different batches of ethylcellulose coated amino acid particles.

TABLE 10d

| | Component | | | |
|---|---|---|---|---|
| | APR Batch 1 (bkT037/72-1) | APR Batch 2 (bkT037/72-2) | APR Batch 3 (bkT037/72-3) | APR Batch 4 (bkT037/72-4) |
| | PSD | | | |
| | 0.5 mm < fraction < 1 mm | 0.5 mm < fraction < 1 mm | 1.0 mm < fraction < 1.6 mm | 1.0 mm < fraction < 1.6 mm |
| Alanine | 5.57 | 5.43 | 5.57 | 5.43 |
| Arginine | 5.70 | 5.55 | 5.70 | 5.55 |
| Cystine | 1.89 | 1.84 | 1.89 | 1.84 |

TABLE 10d-continued

| | APR Batch 1 (bkT037/72-1) | APR Batch 2 (bkT037/72-2) | APR Batch 3 (bkT037/72-3) | APR Batch 4 (bkT037/72-4) |
|---|---|---|---|---|
| | PSD | | | |
| | 0.5 mm < fraction < 1 mm | 0.5 mm < fraction < 1 mm | 1.0 mm < fraction < 1.6 mm | 1.0 mm < fraction < 1.6 mm |
| Glutamine | 11.60 | 11.30 | 11.60 | 11.30 |
| Glicine | 4.16 | 4.05 | 4.16 | 4.05 |
| Histidine HCl | 3.48 | 3.39 | 3.48 | 3.39 |
| Aspartic Acid | 8.55 | 8.32 | 8.55 | 8.32 |
| Proline | 6.70 | 6.52 | 6.70 | 6.52 |
| Serine | 5.48 | 5.34 | 5.48 | 5.34 |
| Taurine | 0.23 | 0.23 | 0.23 | 0.23 |
| Tyrosine | 6.98 | 6.79 | 6.98 | 6.79 |
| Carnitine | 0.15 | 0.14 | 0.15 | 0.14 |
| Isoleucine | 4.75 | 4.62 | 4.75 | 4.62 |
| Lysine HCl | 6.86 | 6.68 | 6.86 | 6.68 |
| Threonine | 4.90 | 4.78 | 4.90 | 4.78 |
| Tryptophan | 1.56 | 1.52 | 1.56 | 1.52 |
| Leucine | 8.53 | 8.30 | 8.53 | 8.30 |
| Valine | 5.94 | 5.78 | 5.94 | 5.78 |
| Methionine | 1.90 | 1.85 | 1.90 | 1.85 |
| Sodium alginate | 0.07 | 0.07 | 0.07 | 0.07 |
| Ethylcellulose | 5.00 | 7.50 | 5.00 | 7.50 |
| Total | 100.00 | 100.00 | 100.00 | 100.00 |

Manufacturing Method (General)
Manufacturing Equipment Used for the Preparation of the Product
   Balances of various types
   ProCepT Mipro 900 ml set-up
   Sieves
   Static oven
   ProCepT Fluid bed bottom-up coating (melt nozzle) (or any other apparatus suitable for the granulate hot melt coating)
Amino Acids Mixture
   Mix all amino acids in a suitable apparatus.
Granulate Preparation
   Transfer the amino acid mixture into the ProCepT Mipro. add the granulating solution composed of a 2% sodium alginate water solution and granulate. After the granulation sieve the granulate; use the fraction having 0.5 mm<PSD<1 mm and 0.5 mm<PSD<1.5 mm for the next step.
Coating with Ethylcellulose (Polymer Coating)
   Transfer the sieved fraction of the granulate to the fluid bed apparatus and spray coat it with an ethanol solution at 15% (w/w) of ethylcellulose. The total amount of polymer added should equal approximately 5.00% and 7.50% of the granulate weight.
Dissolution Test on the Product
   Dissolution Conditions:
Dissolution Medium: Medium pH 1.2±0.1 (0.1N Hydrochloric acid)
Apparatus: Paddle Apparatus (Apparatus 2. USP <711> modified); 50 rpm
Time: 30-60-120-180-240 minutes
Temperature: 37±0.5° C.
Volume Medium: 500 mL
Sample: 2.0 g of Amino Acid mixture
Ponderal Dissolution test: Sampling Time: 30-60-120-180 minutes
   Each time point has his own dissolution vessel.

Figure 9:
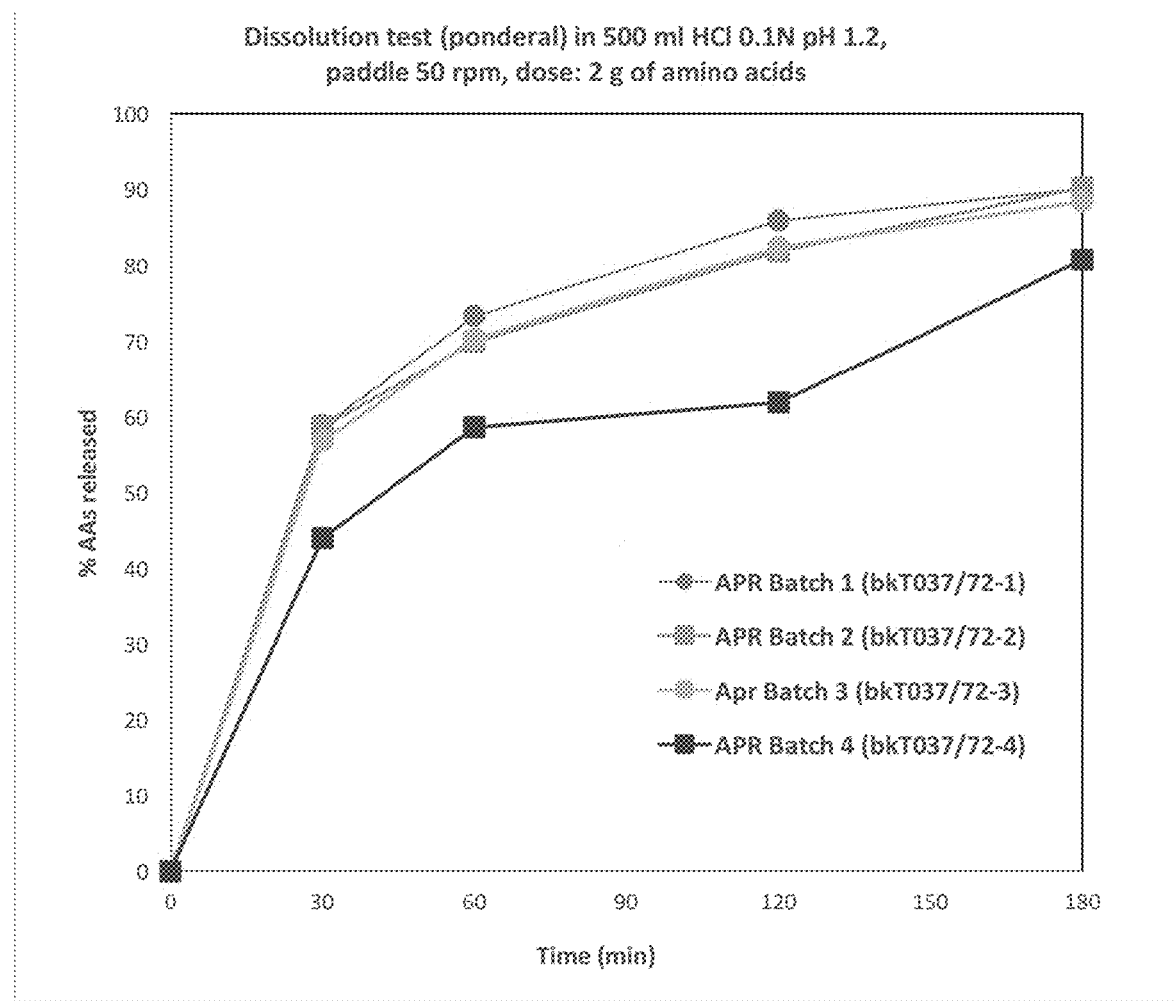
FIG. 9 is a graphical depiction of the ponderal dissolution profile of four separate ethylcellulose coated modified release amino acid formulations, made and tested according to the methods and formulation reported in Example 11 and Table 10d and 10e.

At 30-60-120-180 minutes the dissolution medium were filtered through a paper filter under vacuum. The filtered powder and filter were dried for ±4 hours in a vacuum oven at 50° C. until constant weight achieved and the samples were the weighed. For difference the released quantity of amino acids was calculated. Results The results of ponderal dissolution testing are reported in Table 10e and FIG. 9.

TABLE 10e

| Batch | Time (min) | % Aas released |
|---|---|---|
| APR Batch 1 bkT037/72-1) | 0 | 0 |
| | 30 | 59 |
| | 60 | 73 |
| | 120 | 86 |
| | 180 | 90 |
| APR Batch 2 (bkT037/72-2) | 0 | 0 |
| | 30 | 59 |
| | 60 | 70 |
| | 120 | 82 |
| | 180 | 90 |
| APR Batch 3 (bkT037/72-3) | 0 | 0 |
| | 30 | 57 |
| | 60 | 70 |
| | 120 | 82 |
| | 180 | 88 |
| APR Batch 4 (bkT037/72-4) | 0 | 0 |
| | 30 | 44 |
| | 60 | 59 |
| | 120 | 62 |
| | 180 | 81 |

The analyses of the release of single amino acids have been performed only on prototypes APR Batch 2 and APR Batch 4
Analytical Conditions:
   HPLC: Agilent series 1200
   Detector: Fluorimeter Agilent series 1200
   Chromatographic Column: YMC-Triart C18 12 nm S (250×4.6 mm-5 µm)

Amino Acids are analyzed after extraction (with different ways) and derivatization with FMOC (9-Fluorenyl methyl chloroformate). Note: Carnitina is analyzed by LC/MS.
Results (Single Amino Acids)

Figure 10:
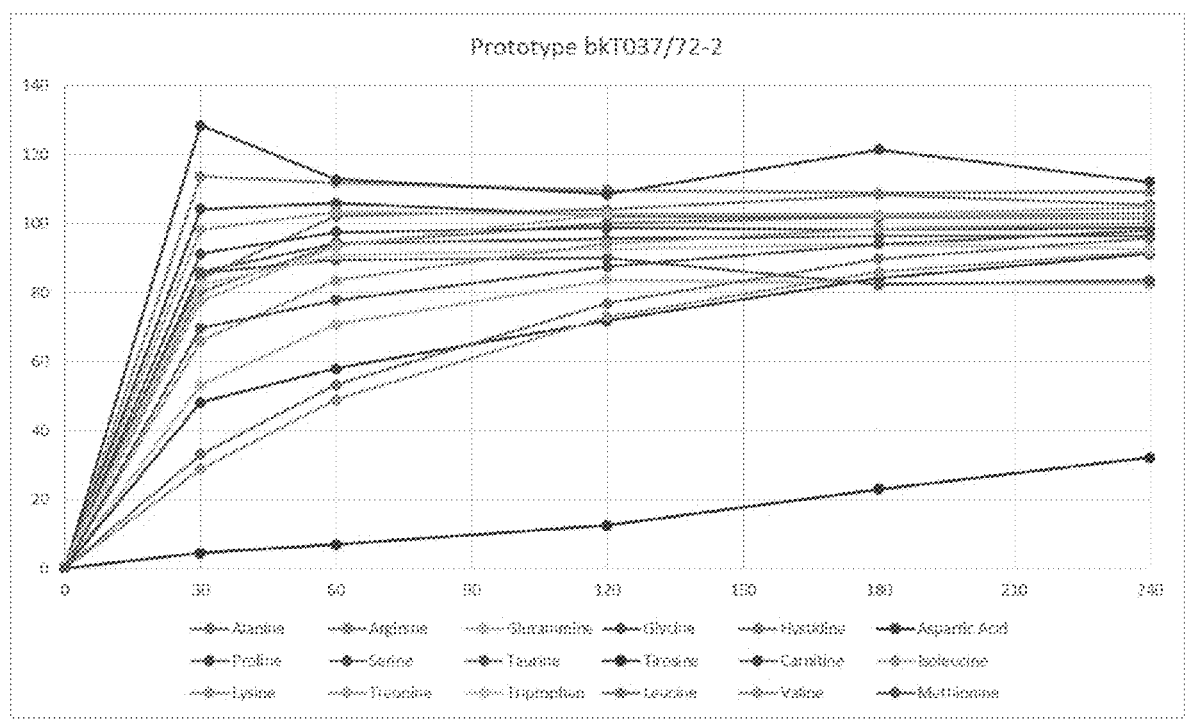
FIG. 10 plots the dissolution profile for the 18 separate amino acids from APR Batch 2 (bkT037/72-2), Table 10f, when tested according to the methods reported in Example 11.

The results of the dissolution testing for APR Batch 2 (bkT037/72-2) are reported in Table 10f and FIG. 10.

TABLE 10f

| Amino Acid | 0 | 30 | 60 | 120 | 180 | 240 |
|---|---|---|---|---|---|---|
| Alanine | 0 | 80.1 | 94.1 | 100.0 | 102.0 | 102.9 |
| Arginine | 0 | 113.7 | 111.9 | 109.7 | 108.8 | 109.2 |
| Glutammine | 0 | 53.2 | 70.7 | 83.7 | 82.8 | 82.5 |
| Glycine | 0 | 85.9 | 94.3 | 95.6 | 96.3 | 96.3 |
| Hystidine | 0 | 84.0 | 102.2 | 104.0 | 108.4 | 105.5 |
| Aspartic Acid | 0 | 48.1 | 57.9 | 71.8 | 84.0 | 91.2 |
| Proline | 0 | 104.1 | 105.8 | 102.3 | 101.8 | 101.5 |
| Serine | 0 | 91.2 | 97.6 | 98.7 | 98.3 | 98.7 |
| Taurine | 0 | 85.7 | 89.6 | 90.0 | 82.2 | 83.5 |
| Tirosine | 0 | 4.5 | 6.8 | 12.4 | 23.0 | 32.1 |
| Carnitine | 0 | 128.6 | 112.9 | 108.6 | 121.4 | 112.1 |
| Isoleucine | 0 | 28.8 | 48.9 | 72.9 | 85.9 | 91.8 |
| Lysine | 0 | 98.1 | 103.4 | 102.8 | 102.2 | 101.7 |
| Treonine | 0 | 77.4 | 93.5 | 102.7 | 102.7 | 104.6 |
| Triptophan | 0 | 82.2 | 90.8 | 92.8 | 94.1 | 92.8 |
| Leucine | 0 | 33.0 | 53.1 | 76.9 | 89.8 | 95.8 |
| Valine | 0 | 65.9 | 83.6 | 94.1 | 98.6 | 100.2 |
| Methionine | 0 | 69.7 | 77.8 | 87.6 | 94.1 | 97.8 |

Figure 11:
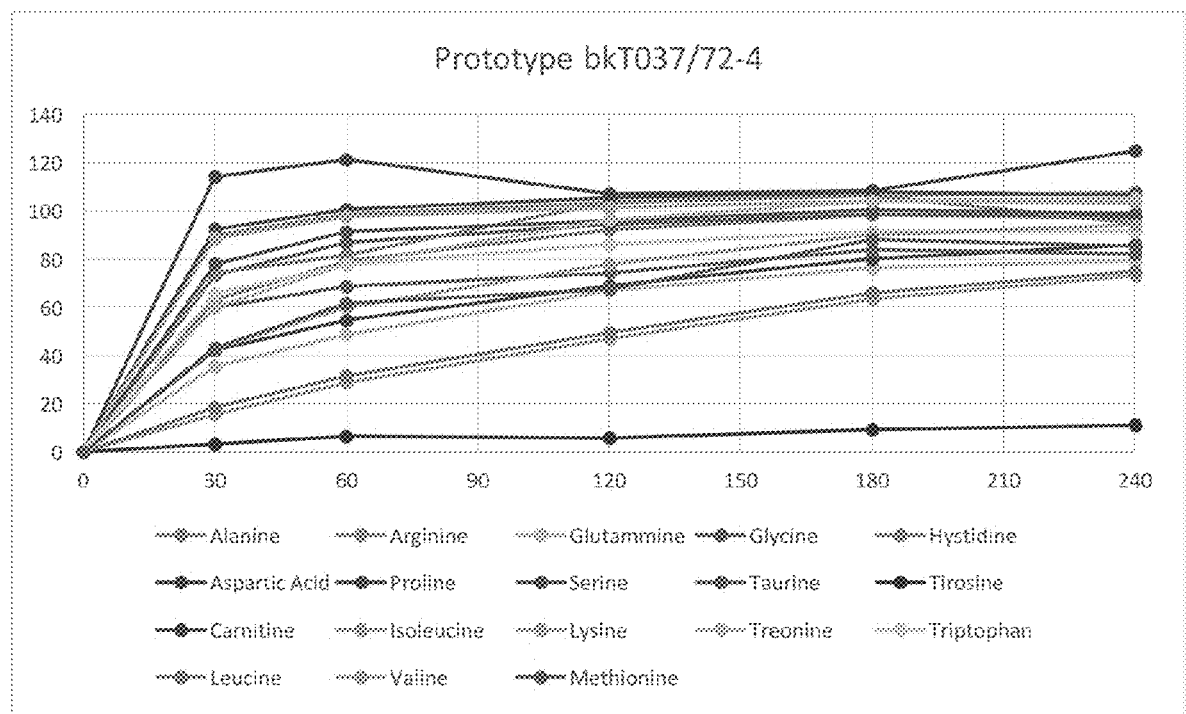
FIG. 11 plots the dissolution profile for the 18 separate amino acids from APR Batch 4 (bkT037/72-4), Table 10g, when tested according to the methods reported in Example 11.

The results of the dissolution testing for APR Batch 4 (bkT037/72-4) are reported in Table 10g and FIG. 11.

TABLE 10g

| Amino Acid | 0 | 30 | 60 | 120 | 180 | 240 |
|---|---|---|---|---|---|---|
| Alanine | 0 | 63.2 | 79.2 | 92.3 | 98.5 | 97.1 |
| Arginine | 0 | 89.9 | 98.7 | 103.4 | 106.5 | 107.7 |
| Glutammine | 0 | 35.6 | 48.8 | 67.1 | 76.5 | 79.5 |
| Glycine | 0 | 73.6 | 86.9 | 94.6 | 98.8 | 97.8 |
| Hystidine | 0 | 74.2 | 81.8 | 103.6 | 106.5 | 94.9 |
| Aspartic Acid | 0 | 42.3 | 54.7 | 68.9 | 80.2 | 86.1 |
| Proline | 0 | 92.5 | 100.6 | 105.4 | 108.0 | 106.7 |
| Serine | 0 | 78.1 | 91.4 | 95.9 | 100.4 | 99.1 |
| Taurine | 0 | 60.0 | 68.7 | 74.3 | 83.9 | 82.2 |
| Tirosine | 0 | 3.2 | 6.5 | 5.8 | 9.4 | 11.1 |
| Carnitine | 0 | 114.3 | 121.4 | 107.1 | 108.6 | 125.0 |
| Isoleucine | 0 | 15.6 | 28.8 | 47.0 | 63.4 | 73.2 |
| Lysine | 0 | 88.8 | 97.8 | 101.5 | 104.3 | 103.6 |
| Treonine | 0 | 60.0 | 78.0 | 96.2 | 104.2 | 105.2 |
| Triptophan | 0 | 65.7 | 77.6 | 86.2 | 91.4 | 91.4 |
| Leucine | 0 | 18.4 | 31.6 | 49.4 | 66.0 | 74.9 |
| Valine | 0 | 42.9 | 60.0 | 77.9 | 90.1 | 94.1 |
| Methionine | 0 | 43.2 | 61.6 | 67.6 | 88.1 | 85.4 |

Example 12—Manufacturing and Dissolution Testing of Modified Release Formulations Using Ethylcellulose and Glyceryl Dibehenate as Coating Agents Table 11a reports the qualitative and quantitative composition of 4 separate amino acid formulation coated with ethylcellulose and glyceryl dibehenate as release rate modifying agents.

TABLE 11a

| | Component | | | |
|---|---|---|---|---|
| | APR Batch 5 (bkT037/73-5) | APR Batch 6 (bkT037/73-6) | APR Batch 7 (bkT037/73-7) | APR Batch 8 (bkT037/73-8) |
| | | | PSD | |
| | 0.5 mm < fraction < 1 mm | 0.5 mm < fraction < 1 mm | 1.0 mm < fraction < 1.6 mm | 1.0 mm < fraction < 1.6 mm |
| Alanine | 5.00 | 4.87 | 5.00 | 4.87 |
| Arginine | 5.12 | 4.98 | 5.12 | 4.98 |
| Cystine | 1.69 | 1.65 | 1.69 | 1.65 |
| Glutamine | 10.41 | 10.13 | 10.41 | 10.13 |
| Glicine | 3.73 | 3.63 | 3.73 | 3.63 |
| Histidine HCl | 3.12 | 3.04 | 3.12 | 3.04 |
| Aspartic Acid | 7.67 | 7.46 | 7.67 | 7.46 |
| Proline | 6.01 | 5.85 | 6.01 | 5.85 |
| Serine | 4.92 | 4.79 | 4.92 | 4.79 |
| Taurine | 0.21 | 0.20 | 0.21 | 0.20 |
| Tyrosine | 6.26 | 6.09 | 6.26 | 6.09 |
| Carnitine | 0.13 | 0.13 | 0.13 | 0.13 |
| Isoleucine | 4.26 | 4.15 | 4.26 | 4.15 |
| Lysine HCl | 6.16 | 6.00 | 6.16 | 6.00 |
| Threonine | 4.40 | 4.28 | 4.40 | 4.28 |
| Tryptophan | 1.40 | 1.36 | 1.40 | 1.36 |
| Leucine | 7.65 | 7.45 | 7.65 | 7.45 |
| Valine | 5.32 | 5.18 | 5.32 | 5.18 |
| Methionine | 1.70 | 1.65 | 1.70 | 1.65 |
| Sodium alginate | 0.06 | 0.06 | 0.06 | 0.06 |
| Ethylcellulose | 4.49 | 6.71 | 4.49 | 6.71 |
| Glyceryl dibehenate | 10.0 | 10.00 | 10.00 | 10.00 |
| Total | 100.00 | 100.00 | 100.00 | 100.00 |

Figure 12:
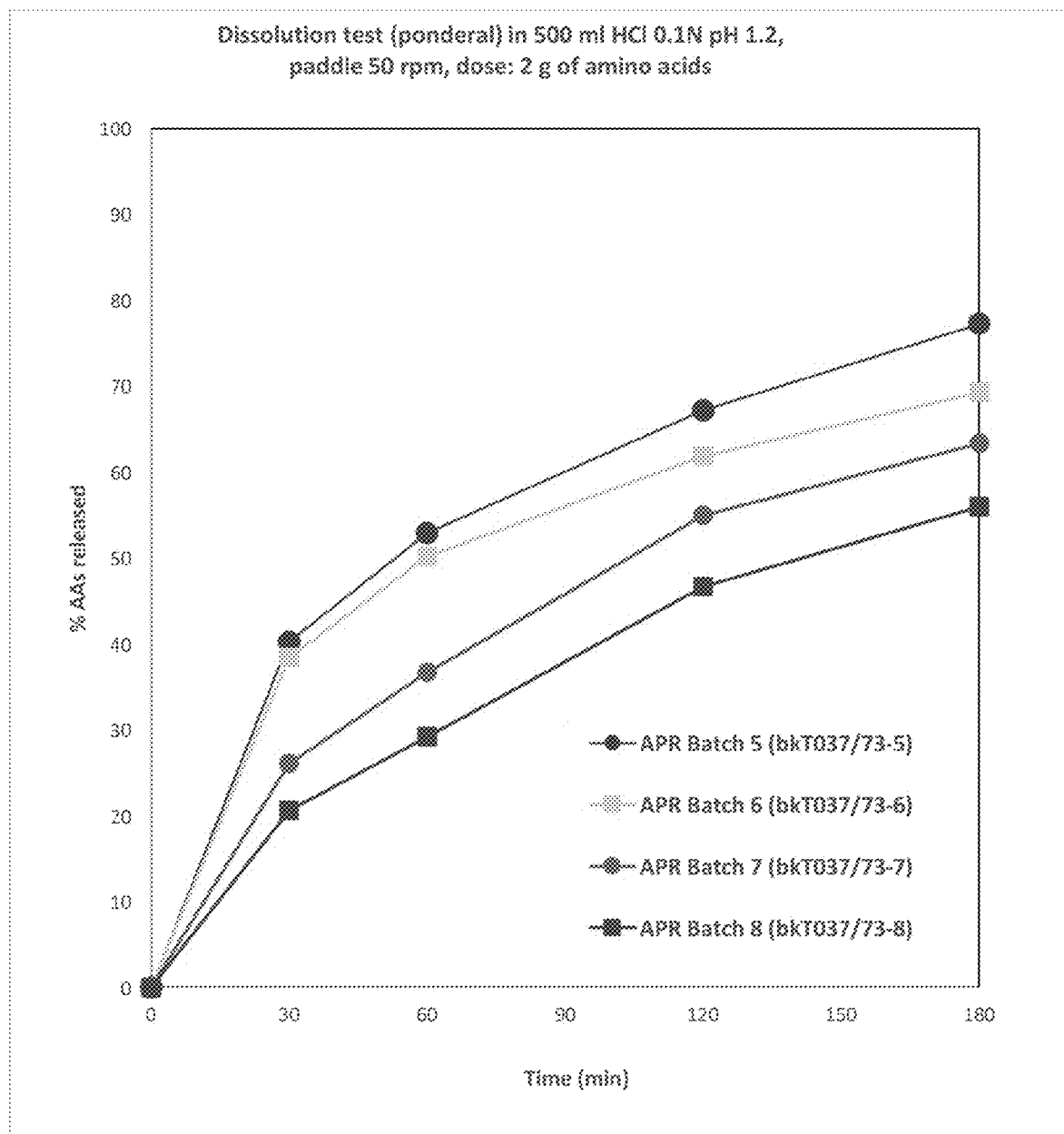

Manufacturing Method (General)
Manufacturing Equipment Used for the Preparation of the Product
  Balances of various types
  ProCepT Mipro 900 ml set-up
  Sieves
  Static oven
  ProCepT Fluid bed bottom-up coating (melt nozzle) (or any other apparatus suitable for the granulate hot melt coating)
Amino Acid Mixture
  Mix all amino acids in a suitable apparatus
Granulate Preparation
  Transfer the amino acids mixture into the ProCepT Mipro. add the granulating solution composed of a 2% sodium alginate water solution and granulate. After the granulation sieve the granulate; use the fraction having 0.5 mm<PSD<1 mm or 0.5 mm<PSD<1.6 mm for the next step.
Coating with Ethylcellulose (Polymer Coating)
  Transfer the sieved fraction of granulate in the fluid bed apparatus and spray coat it with a methanol solution at 15% (w/w) of ethylcellulose. The total amount of polymer added should equal approximately 5.00% and 7.50% of the granulate weight.
Coating with Glyceryl Dibehenate (Hot Melt Coating)
  Transfer the granulate coated with ethylcellulose in the fluid bed apparatus and spray coat it with melted glyceryl dibehenate. The total amount of polymer added should equal approximately 10.00% of the granulate weight.
  Analytical Conditions:
Dissolution test on the Product
Dissolution Medium: Medium pH 1.2±0.1 (0.1N Hydrochloric acid)
Apparatus: Paddle Apparatus (Apparatus 2. USP <711> modified); 50 rpm
Time: 30-60-120-180-240 minutes
Temperature: 37±0.5° C.
Volume Medium: 500 mL
Sample: 2.0 g of Amino Acid mixture
Ponderal dissolution test: Sampling Time: 30-60-120-180 minutes
  At 30-60-120-180 minutes the dissolution medium were filtered through a paper filter under vacuum. The filtered powder and filter were dried for ±4 hours in a vacuum oven at 50° C. until constant weight achieved and the samples were the weighed. For difference the released quantity of amino acids was calculated
Results
  The results of the ponderal dissolution testing are reported in Table 11b and FIG. 12.

TABLE 11b

| Batch | Time (min) | % Aas released |
|---|---|---|
| APR Batch 5 (bkT037/73-5) | 0 | 0 |
|  | 30 | 40 |
|  | 60 | 53 |
|  | 120 | 67 |
|  | 180 | 77 |
| APR Batch 6 (bkT037/73-6) | 0 | 0 |
|  | 30 | 38 |
|  | 60 | 50 |
|  | 120 | 62 |
|  | 180 | 69 |
| APR Batch 7 (bkT037/73-7) | 0 | 0 |
|  | 30 | 26 |
|  | 60 | 37 |
|  | 120 | 55 |
|  | 180 | 63 |
| APR Batch 8 (bkT037/73-8) | 0 | 0 |
|  | 30 | 21 |
|  | 60 | 29 |
|  | 120 | 47 |
|  | 180 | 56 |

Figure 13:
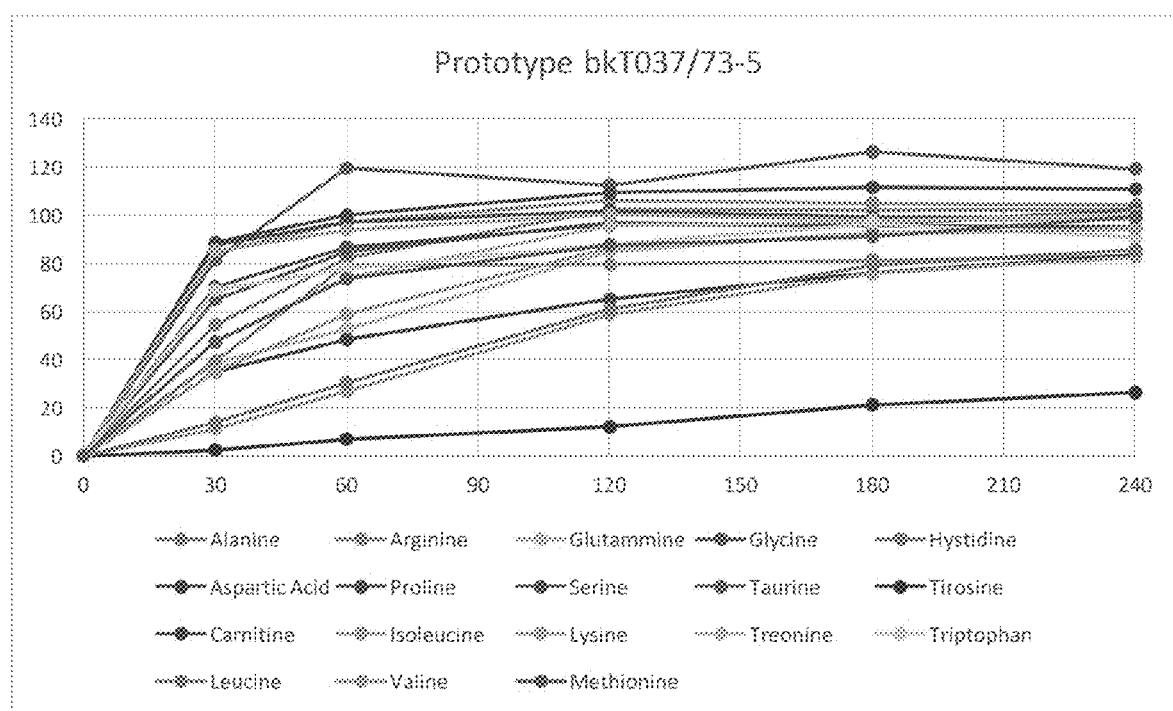
FIG. 13 plots the dissolution profile of 18 separate amino acids from APR Batch 5 (bkT037/73-5) (Table 11c), when tested according to the methods reported in Example 12.

The analyses have been performed on prototypes APR Batch 5 and APR Batch 7
Analytical Conditions:
  HPLC: Agilent series 1200
  Detector: Fluorimeter Agilent series 1200
  Chromatographic Column: YMC-Triart C18 12 nm S (250×4.6 mm-5 μm)
Amino Acids are analyzed after derivatization with FMOC (9-Fluorenyl methyl chloroformate)
Note: Carnitina is analyzed by LC/MS.
Results (Single Amino Acids)
  The single amino acid dissolution test results for APR Batch 5 (bkT037/73-5) are reported in Table 11c and FIG. 13.

TABLE 11c

| Amino Acid | Time (min) | | | | | |
|---|---|---|---|---|---|---|
|  | 0 | 30 | 60 | 120 | 180 | 240 |
| Alanine | 0 | 54.4 | 82.0 | 102.2 | 102.0 | 102.2 |
| Arginine | 0 | 84.6 | 97.1 | 106.1 | 104.9 | 104.1 |
| Glutammine | 0 | 38.5 | 52.6 | 84.9 | 92.9 | 93.9 |
| Glycine | 0 | 64.9 | 84.7 | 96.8 | 95.7 | 102.4 |
| Hystidine | 0 | 39.3 | 79.1 | 79.5 | 81.1 | 83.1 |
| Aspartic Acid | 0 | 34.8 | 48.2 | 65.1 | 76.0 | 83.4 |
| Proline | 0 | 87.7 | 97.2 | 101.8 | 99.2 | 98.7 |
| Serine | 0 | 70.1 | 86.6 | 96.1 | 95.5 | 95.1 |
| Taurine | 0 | 81.4 | 119.5 | 112.4 | 126.2 | 119.0 |
| Tirosine | 0 | 2.4 | 6.9 | 12.0 | 21.2 | 26.4 |
| Carnitine | 0 | 88.5 | 100.0 | 109.2 | 111.5 | 110.8 |
| Isoleucine | 0 | 11.2 | 26.8 | 58.7 | 75.8 | 82.6 |
| Lysine | 0 | 85.2 | 93.9 | 100.2 | 98.2 | 98.4 |
| Treonine | 0 | 47.5 | 74.1 | 95.5 | 97.3 | 100.2 |
| Triptophan | 0 | 68.8 | 77.9 | 87.9 | 96.4 | 90.7 |
| Leucine | 0 | 13.9 | 30.5 | 60.8 | 79.1 | 85.6 |
| Valine | 0 | 35.0 | 58.8 | 86.3 | 91.7 | 94.5 |
| Methionine | 0 | 47.4 | 73.5 | 87.6 | 91.2 | 99.4 |

Figure 14:
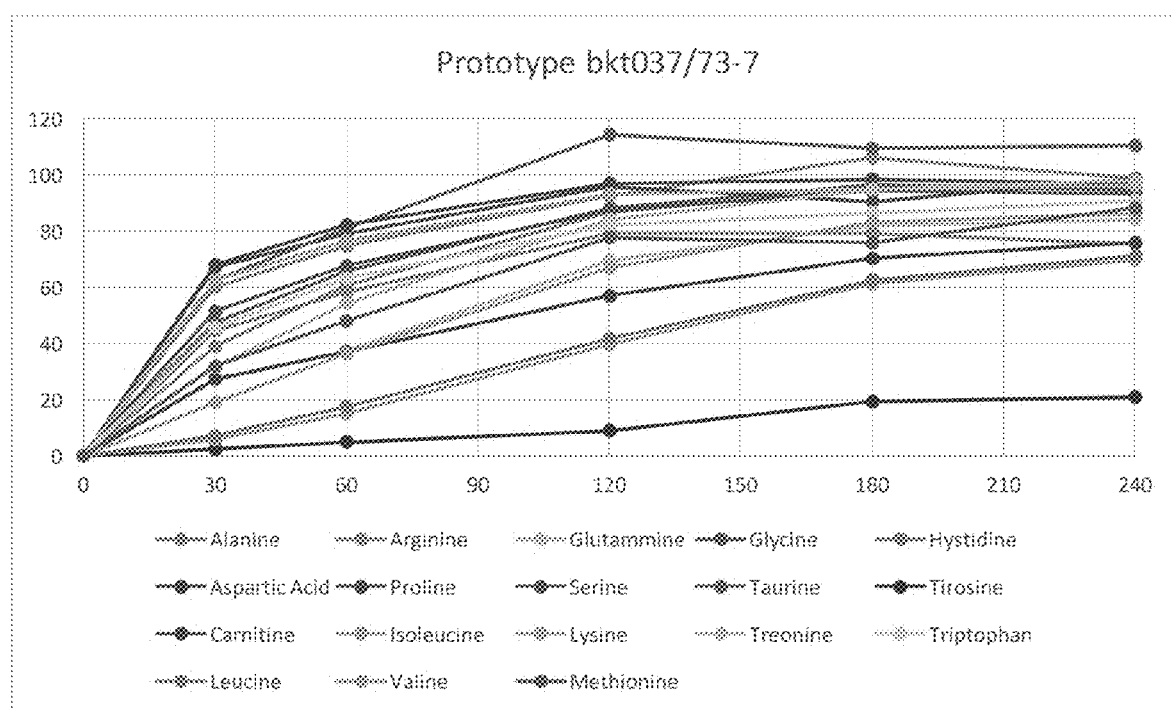
FIG. 14 plots the dissolution profile of 18 separate amino acids from APR Batch 7 (bkT037/72-7) (Table 11d), when tested according to the methods reported in Example 12.

The single amino acid dissolution test results for APR Batch 7 (bkT037/72-7) are reported in Table 11d and FIG. 14.

TABLE 11d

| Amino Acid | Time (min) | | | | | |
|---|---|---|---|---|---|---|
|  | 0 | 30 | 60 | 120 | 180 | 240 |
| Alanine | 0 | 39.0 | 60.8 | 86.8 | 95.0 | 96.0 |
| Arginine | 0 | 60.2 | 74.8 | 92.6 | 106.1 | 98.8 |
| Glutammine | 0 | 27.0 | 37.4 | 69.5 | 81.9 | 84.1 |
| Glycine | 0 | 47.5 | 66.0 | 88.2 | 96.5 | 94.6 |
| Hystidine | 0 | 44.5 | 58.3 | 79.1 | 79.1 | 75.6 |
| Aspartic Acid | 0 | 27.4 | 37.2 | 57.0 | 70.3 | 75.9 |
| Proline | 0 | 67.1 | 79.0 | 95.8 | 91.2 | 98.7 |
| Serine | 0 | 51.4 | 67.7 | 87.2 | 94.3 | 93.3 |
| Taurine | 0 | 62.4 | 81.0 | 114.3 | 109.5 | 110.5 |
| Tirosine | 0 | 2.4 | 4.9 | 8.9 | 19.3 | 20.9 |
| Carnitine | 0 | 68.0 | 82.3 | 96.9 | 98.5 | 96.9 |
| Isoleucine | 0 | 5.8 | 15.0 | 39.7 | 61.3 | 69.7 |
| Lysine | 0 | 62.6 | 76.6 | 93.1 | 94.9 | 96.3 |
| Treonine | 0 | 31.6 | 54.3 | 84.1 | 94.8 | 98.2 |
| Triptophan | 0 | 45.7 | 63.2 | 82.1 | 86.4 | 90.7 |

TABLE 11d-continued

| Amino Acid | Time (min) | | | | | |
|---|---|---|---|---|---|---|
| | 0 | 30 | 60 | 120 | 180 | 240 |
| Leucine | 0 | 7.1 | 17.5 | 41.7 | 62.5 | 71.2 |
| Valine | 0 | 19.0 | 36.5 | 66.9 | 83.3 | 86.1 |
| Methionine | 0 | 31.9 | 48.0 | 77.6 | 75.9 | 88.2 |

Figure 15:
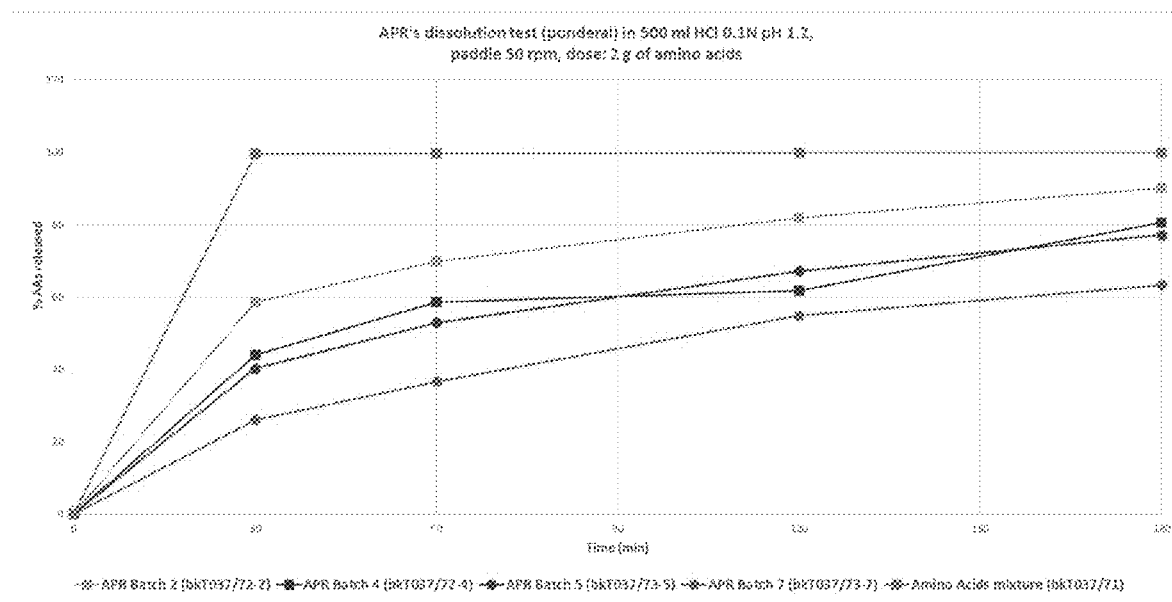
FIG. 15 depicts the aggregate ponderal amino acid dissolution profiles of four separate test formulations of the current inventions (APR Batch 2/bkT037/72-2, APR Batch 4/bkT037/72-4, APR Batch 5/bkT037/73-5, APR Batch 7/bkT037/72-7) and free amino acids mixture bkT037/71, manufactured and tested as described in Examples 11 and 12.

Table 11e and FIG. 15 report the total amino acids released (Ponderal Dissolution Test) at various time points from each of the four test formulations. compared to an immediate release amino acid formulation.

TABLE 11e

| Batch | Time (min) | % Aas released |
|---|---|---|
| APR Batch 2 (bkT037/72-2) | 0 | 0 |
| | 30 | 59 |
| | 60 | 70 |
| | 120 | 82 |
| | 180 | 90 |
| APR Batch 4 (bkT037/72-4) | 0 | 0 |
| | 30 | 44 |
| | 60 | 59 |
| | 120 | 62 |
| | 180 | 81 |
| APR Batch 5 (bkT037/73-5) | 0 | 0 |
| | 30 | 40 |
| | 60 | 53 |
| | 120 | 67 |
| | 180 | 77 |
| APR Batch 7 (bkT037/73-7) | 0 | 0 |
| | 30 | 26 |
| | 60 | 37 |
| | 120 | 55 |
| | 180 | 63 |
| AA mixture (bkT037/71) | 0 | 0 |
| | 30 | 100 |
| | 60 | 100 |
| | 120 | 100 |
| | 180 | 100 |

Tables 11f-11j report the quantity of individual amino acids released from the four different test formulation at distinct time points.

TABLE 11f

| | 30 Minutes | | | | |
|---|---|---|---|---|---|
| Amino Acid | Free AA (bkT037/71) | APR Batch 2 (bkT037/72-2) | APR Batch 4 (bkT037/72-4) | APR Batch 5 (bkT037/73-5) | APR Batch 7 (bkT037/73-7) |
| Alanine | 111.8 | 80.1 | 63.2 | 54.4 | 39.0 |
| Arginine | 110.1 | 113.7 | 89.9 | 84.6 | 60.2 |
| Glutammine | 85.9 | 53.2 | 35.6 | 38.5 | 27.0 |
| Glycine | 112.6 | 85.9 | 73.6 | 64.9 | 47.5 |
| Hystidine | 102.7 | 84.0 | 74.2 | 39.3 | 44.5 |
| Aspartic Acid | 103.7 | 48.1 | 42.3 | 34.8 | 27.4 |
| Proline | 109.9 | 104.1 | 92.5 | 87.7 | 67.1 |
| Serine | 108.1 | 91.2 | 78.1 | 70.1 | 51.4 |
| Taurine | 120.0 | 85.7 | 60.0 | 81.4 | 62.4 |
| Tirosine | 103.9 | 4.5 | 3.2 | 2.4 | 2.4 |
| Carnitine | 122.5 | 128.6 | 114.3 | 88.5 | 68.0 |
| Isoleucine | 103.6 | 28.8 | 15.6 | 11.2 | 5.8 |
| Lysine | 103.8 | 98.1 | 88.8 | 85.2 | 62.6 |
| Treonine | 97.7 | 77.4 | 60.0 | 47.5 | 31.6 |
| Triptophan | 100.0 | 82.2 | 65.7 | 68.8 | 45.7 |
| Leucine | 110.1 | 33.0 | 18.4 | 13.9 | 7.1 |
| Valine | 105.4 | 65.9 | 42.9 | 35.0 | 19.0 |
| Methionine | 107.0 | 69.7 | 43.2 | 47.4 | 31.9 |

TABLE 11g

| | 60 Minutes | | | | |
|---|---|---|---|---|---|
| Amino Acid | Free AA (bkT037/71) | APR Batch 2 (bkT037/72-2) | APR Batch 4 (bkT037/72-4) | APR Batch 5 (bkT037/73-5) | APR Batch 7 (bkT037/73-7) |
| Alanine | 109.0 | 94.1 | 79.2 | 82.0 | 60.8 |
| Arginine | 107.0 | 111.9 | 98.7 | 97.1 | 74.8 |
| Glutammine | 84.3 | 70.7 | 48.8 | 52.6 | 37.4 |
| Glycine | 109.4 | 94.3 | 86.9 | 84.7 | 66.0 |
| Hystidine | 96.3 | 102.2 | 81.8 | 79.1 | 58.3 |
| Aspartic Acid | 106.6 | 57.9 | 54.7 | 48.2 | 37.2 |
| Proline | 108.1 | 105.8 | 100.6 | 97.2 | 79.0 |
| Serine | 105.2 | 97.6 | 91.4 | 86.6 | 67.7 |
| Taurine | 125.8 | 89.6 | 68.7 | 119.5 | 81.0 |
| Tirosine | 101.2 | 6.8 | 6.5 | 6.9 | 4.9 |
| Carnitine | 121.3 | 112.9 | 121.4 | 100.0 | 82.3 |
| Isoleucine | 100.6 | 48.9 | 28.8 | 26.8 | 15.0 |
| Lysine | 101.6 | 103.4 | 97.8 | 93.9 | 76.6 |
| Treonine | 96.3 | 93.5 | 78.0 | 74.1 | 54.3 |
| Triptophan | 100.6 | 90.8 | 77.6 | 77.9 | 63.2 |
| Leucine | 106.6 | 53.1 | 31.6 | 30.5 | 17.5 |

TABLE 11g-continued

| | 60 Minutes | | | | |
|---|---|---|---|---|---|
| Amino Acid | Free AA (bkT037/71) | APR Batch 2 (bkT037/72-2) | APR Batch 4 (bkT037/72-4) | APR Batch 5 (bkT037/73-5) | APR Batch 7 (bkT037/73-7) |
| Valine | 103.4 | 83.6 | 60.0 | 58.8 | 36.5 |
| Methionine | 104.5 | 77.8 | 61.6 | 73.5 | 48.0 |

TABLE 11h

| | 120 Minutes | | | |
|---|---|---|---|---|
| Amino Acid | APR Batch 2 (bkT037/72-2) | APR Batch 4 (bkT037/72-4) | APR Batch 5 (bkT037/73-5) | APR Batch 7 (bkT037/73-7) |
| Alanine | 100.0 | 92.3 | 102.2 | 86.8 |
| Arginine | 109.7 | 103.4 | 106.1 | 92.6 |
| Glutammine | 83.7 | 67.1 | 84.9 | 69.5 |
| Glycine | 95.6 | 94.6 | 96.8 | 88.2 |
| Hystidine | 104.0 | 103.6 | 79.5 | 79.1 |
| Aspartic Acid | 71.8 | 68.9 | 65.1 | 57.0 |
| Proline | 102.3 | 105.4 | 101.8 | 95.8 |
| Serine | 98.7 | 95.9 | 96.1 | 87.2 |
| Taurine | 90.0 | 74.3 | 112.4 | 114.3 |
| Tirosine | 12.4 | 5.8 | 12.0 | 8.9 |
| Carnitine | 108.6 | 107.1 | 109.2 | 96.9 |
| Isoleucine | 72.9 | 47.0 | 58.7 | 39.7 |
| Lysine | 102.8 | 101.5 | 100.2 | 93.1 |
| Treonine | 102.7 | 96.2 | 95.5 | 84.1 |
| Triptophan | 92.8 | 86.2 | 87.9 | 82.1 |
| Leucine | 76.9 | 49.4 | 60.8 | 41.7 |
| Valine | 94.1 | 77.9 | 86.3 | 66.9 |
| Methionine | 87.6 | 67.6 | 87.6 | 77.6 |

TABLE 11i

| | 180 Minutes | | | |
|---|---|---|---|---|
| | APR Batch 2 (bkT037/72-2) | APR Batch 4 (bkT037/72-4) | APR Batch 5 (bkT037/73-5) | APR Batch 7 (bkT037/73-7) |
| Alanine | 102.0 | 98.5 | 102.0 | 95.0 |
| Arginine | 108.8 | 106.5 | 104.9 | 106.1 |
| Glutammine | 82.8 | 76.5 | 92.9 | 81.9 |
| Glycine | 96.3 | 98.8 | 95.7 | 96.5 |
| Hystidine | 108.4 | 106.5 | 81.1 | 79.1 |
| Aspartic Acid | 84.0 | 80.2 | 76.0 | 70.3 |
| Proline | 101.8 | 108.0 | 99.2 | 91.2 |
| Serine | 98.3 | 100.4 | 95.5 | 94.3 |
| Taurine | 82.2 | 83.9 | 126.2 | 109.5 |
| Tirosine | 23.0 | 9.4 | 21.2 | 19.3 |
| Carnitine | 121.4 | 108.6 | 111.5 | 98.5 |
| Isoleucine | 85.9 | 63.4 | 75.8 | 61.3 |
| Lysine | 102.2 | 104.3 | 98.2 | 94.9 |
| Treonine | 102.7 | 104.2 | 97.3 | 94.8 |
| Triptophan | 94.1 | 91.4 | 96.4 | 86.4 |
| Leucine | 89.8 | 66.0 | 79.1 | 62.5 |
| Valine | 98.6 | 90.1 | 91.7 | 83.3 |
| Methionine | 94.1 | 88.1 | 91.2 | 75.9 |

TABLE 11j

| | 240 Minutes | | | |
|---|---|---|---|---|
| | APR Batch 2 (bkT037/72-2) | APR Batch 4 (bkT037/72-4) | APR Batch 5 (bkT037/73-5) | APR Batch 7 (bkT037/73-7) |
| Alanine | 102.9 | 97.1 | 102.2 | 96.0 |
| Arginine | 109.2 | 107.7 | 104.1 | 98.8 |
| Glutammine | 82.5 | 79.5 | 93.9 | 84.1 |
| Glycine | 96.3 | 97.8 | 102.4 | 94.6 |
| Hystidine | 105.5 | 94.9 | 83.1 | 75.6 |
| Aspartic Acid | 91.2 | 86.1 | 83.4 | 75.9 |
| Proline | 101.5 | 106.7 | 98.7 | 98.7 |
| Serine | 98.7 | 99.1 | 95.1 | 93.3 |
| Taurine | 83.5 | 82.2 | 119.0 | 110.5 |
| Tirosine | 32.1 | 11.1 | 26.4 | 20.9 |
| Carnitine | 112.1 | 125.0 | 110.8 | 96.9 |
| Isoleucine | 91.8 | 73.2 | 82.6 | 69.7 |
| Lysine | 101.7 | 103.6 | 98.4 | 96.3 |
| Treonine | 104.6 | 105.2 | 100.2 | 98.2 |
| Triptophan | 92.8 | 91.4 | 90.7 | 90.7 |
| Leucine | 95.8 | 74.9 | 85.6 | 71.2 |
| Valine | 100.2 | 94.1 | 94.5 | 86.1 |
| Methionine | 97.8 | 85.4 | 99.4 | 88.2 |

Example 13—Final Amino Acids Composition

The quantitative composition for phenylketonuria of the amino acid mix has been optimized according to the nutritionists' recommendations; the percentages of the single amino acid are reported in Table 12a.

TABLE 12a

| Amino Acid | % (with HCl) | Amino Acid | % (As Base) |
|---|---|---|---|
| L-Alanine | 2.9 | L-Alanine | 2.9 |
| L-Arginine | 3.9 | L-Arginine | 3.9 |
| L-Cystine | 2.0 | L-Cystine | 2.0 |
| L-Glutamine | 19.5 | L-Glutamine | 19.5 |
| Glicine | 4.9 | Glicine | 4.9 |
| L-Histidine HCl | 3.4 | L-Histidine | 2.76 |
| L-Aspartic Acid | 5.9 | L-Aspartic Acid | 5.9 |
| L-Proline | 5.9 | L-Proline | 5.9 |
| L-Serine | 3.3 | L-Serine | 3.3 |
| Taurine | 0.3 | Taurine | 0.3 |
| L-Tyrosine | 9.8 | L-Tyrosine | 9.8 |
| L-Carnitine | 0.1 | L-Carnitine | 0.1 |
| L-Isoleucine | 5.4 | L-Isoleucine | 5.4 |
| L-Lysine HCl | 8.5 | L-Lysine | 6.80 |
| L-Treonine | 4.9 | L-Treonine | 4.9 |
| L-Tryptophan | 2.0 | L-Tryptophan | 2.0 |
| L-Leucine | 11.2 | L-Leucine | 11.2 |
| L-Valine | 4.9 | L-Valine | 4.9 |
| L-Methionine | 1.4 | L-Methionine | 1.4 |
| Total | 100 | Total | 98 |

Example 14—In Vivo Bioavailability in Pig

An in vivo bioavailability study was undertaken in pigs in order to model the anticipated pharmacokinetics and metabolism of the formulations of the present invention, as compared to a comparable mixture of free amino acids, having similar proportions and total amounts of amino acids, and a commercially available formulation of milk proteins (casein). The following formulations were tested:

APR-04 (bkT037/72-4)
APR-07 (bkT037/73-7)
Free amino acid (bkT037/71)
Casein

In Vivo Study Design:
Subjects: 8 pigs
Design: 4 formulations in crossover
Administration route and method: oral, by gavage. The product dose was administered to each animal mixed with a small amount of water (300 ml) in order to ensure fast (≤5 minutes) assumption. The total amount of the product was administered using syringes. The animals were fasted for 13.5±0.5 hours before the treatment and the access to water was suspended one hour before and one hour after the treatment.
Dose, frequency and duration of administration: The amount of product administered was based on bodyweight and equaled 0.8 g of amino acid/kg body weight for each test product. The products were administered by a single administration in the morning of each day of treatment.
Wash out: 48-72 hours
Blood sampling: 0.75 h before Treatment (T), 0.5 h before T, 0.25 h before T, 0.25 h after T, 0.5 h after T, 0.75 h after T, 1 h after T, 1.25 h after T, 1.5 h after T, 2 h after T, 2.5 h after T, 3 h after T, 4 h after T, 5 h after T
Analysis: The plasma concentrations of 14 amino acids (Alanine, Arginine, Glutamine, Glycine, Histidine, Isoleucine, Leucine, Lysine, Proline, Serine, Threonine, Tryptophan, Tyrosine, Valine) were measured and analyzed. Methionine and Aspartic acid were excluded from the analysis due to stability issues. The following parameters were evaluated: Area Under the concentration/time Curve (AUC0-last), peak concentration ($C_{max}$), time to peak concentration ($T_{max}$) and $C_{last}$. The behavior of the two APR Formulations was compared to the formulation of Free Amino Acids and Casein.

Results:
The plasma concentration of an amino acid (AA) is the result of its rates of appearance (Ra) in and disappearance (Rd) from plasma. Factors controlling Ra include protein intake and tissue release. Factors controlling Rd include tissue uptake and body loss through urine, sweat, etc. Hormones also help to regulate plasma AA concentrations, particularly insulin and glucagon, both of which induce hypoaminoacidemia (but for quite different reasons), and cortisol, which induces hyperaminoacidemia. In addition, in pathologic states, catechol amines, thyroid hormones, and cytokines can modulate plasma AA levels. Peripheral availability of Aas after protein ingestion is controlled by the liver, with an activation of ureagenesis in hyperprotein feeding and repression during a hypoprotein diet (Cynober 2002). All these factors can influence the plasma amino acid concentration reported herein.

1) Mean Aggregate Plasma Amino Acid Concentrations

Figure 16:
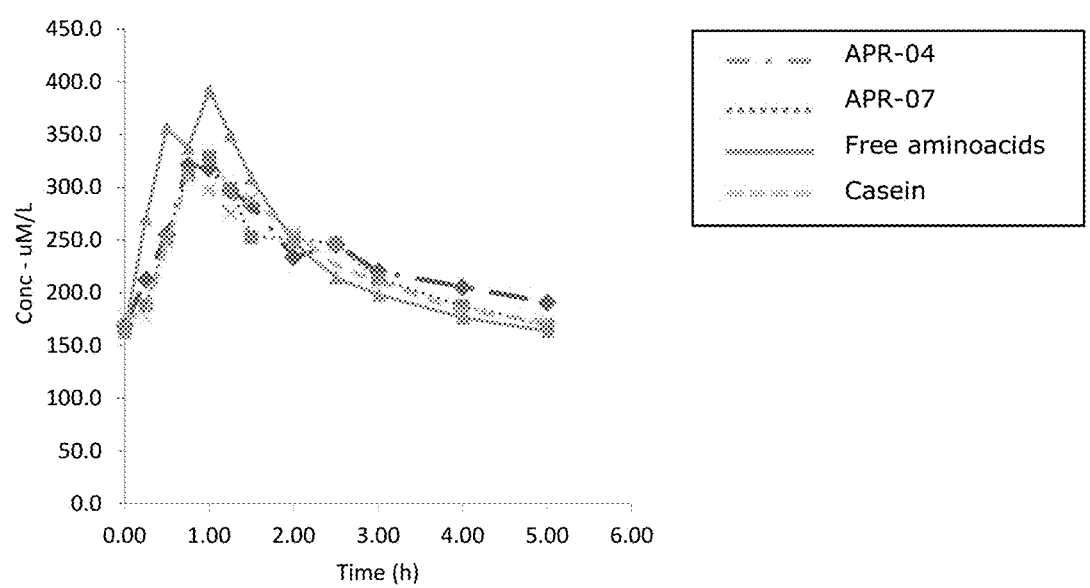
FIG. 16 reports the mean plasma concentrations in pigs of 14 amino acids over time, on an aggregate basis, from two separate modified release amino acid formulations of the present invention, one free amino acid formulation, and casein, as described in Example 14.

The mean plasma concentrations of the 14 amino acids over time, on an aggregate basis, is reported in FIG. 16 and Table 14a. Basal values were not subtracted prior to performing the calculations.

TABLE 14a

| 14 AA (RAW DATA) | APR-04 | APR-07 | Free amino acids | Casein |
|---|---|---|---|---|
| AUC 0-last | 1184.1 | 1141.8 | 1200.7 | 1125.6 |
| $C_{max}$ | 339.0 | 341.9 | 419.2 | 324.8 |
| $C_{last}$ | 190.8 | 168.7 | 163.5 | 172.9 |

The following observations can be made:
The APR Formulations show a lower plasma peak of aggregate amino acids ($C_{max}$) when compared to the free amino acid formulation.
If we consider the curve of the single amino acids, Repeated Measures ANOVA applied to Ln-transformed data show a significant difference (p<0.05) in $C_{max}$ from APR-04 versus Free Amino Acids for Arginine, Isoleucine, Leucine, Tyrosine and Valine.
If we consider the curve of the single amino acids, Repeated Measures ANOVA applied to Ln-transformed data show a significant difference (p<0.05) in $C_{max}$ from APR-07 versus Free Amino Acids for Isoleucine, Leucine, Tyrosine and Valine.
The difference in $C_{max}$ is even more evident is we consider the BC data, in which the basal values of amino acids are subtracted, as shown below in Table 14b, although the difference is not statistically significant for the mean of the entire aggregate of amino acids:

TABLE 14b

| 14 AA (BC DATA) | APR-04 | APR-07 | Free amino acids | Casein |
|---|---|---|---|---|
| AUC 0-last | 332.3 | 302.3 | 382.9 | 258.9 |
| $C_{max}$ | 168.6 | 172.5 | 251.5 | 147.3 |

The higher initial peak plasma concentration of amino acids ($C_{max}$) observed for the Free Amino Acid Formulation rapidly decreases, as evidenced by the "$C_{last}$" parameter. "$C_{last}$" is the amino acid plasma concentration at the last sampling (5 h)
If we compare the curve of the single amino acids, in the group treated with APR-04, the $C_{last}$ is higher (but not statistically significant except for Valine) versus the free Amino Acid Group for Alanine, Arginine, Glutamine, Glycine, Histidine, Isoleucine, Leucine, Lysine, Proline, Serine, Threonine, Tryptophan and Valine (13 amino acids out of 14)
If we compare the curve of the single amino acids, in the group treated with APR-07, the $C_{last}$ is higher (but not statistically significant except for Valine, Isoleucine and Leucine) versus the free Amino Acid Group for Arginine, Histidine, Isoleucine, Leucine, Lysine, Proline, Tryptophan, and Valine (8 amino acids out of 14)
The trend in $C_{max}$ and $C_{last}$ observed in the plasma concentration curve for aggregated amino acids becomes statistically significant if the subgroup of Essential Amino Acids and the subgroup of BCAAs (Branched Chain Amino Acids) is considered (see points 2 and 3).

2) Mean of Analyzed Essential Amino Acid Concentrations (Arginine, Histidine, Isoleucine, Leucine, Threonine, Lysine, Tryptophan and Valine).

Figure 17:
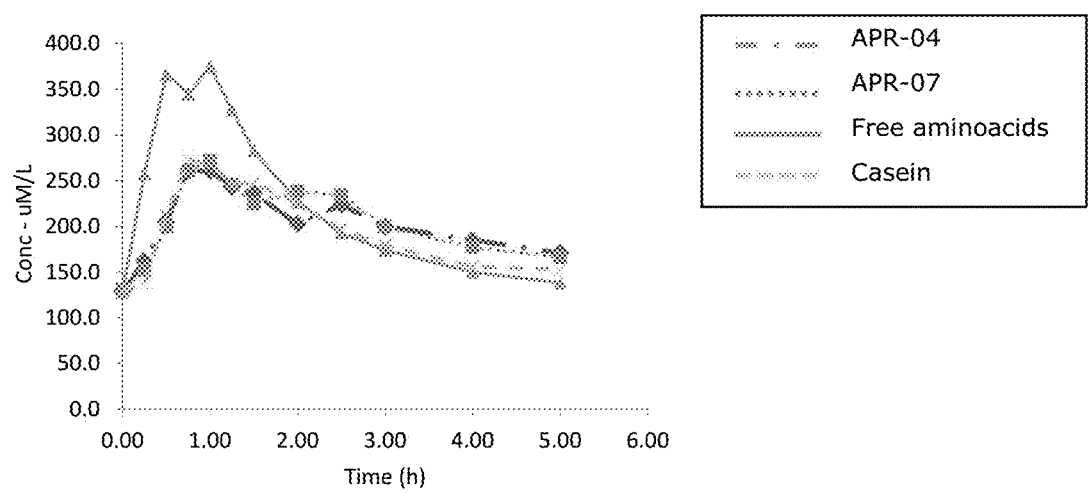
FIG. 17 reports the mean plasma concentrations in pigs of the essential amino acids over time, on an aggregate basis, from two separate modified release amino acid formulations of the present invention, one free amino acid formulation, and casein, as described in Example 14.

The mean plasma concentrations of the essential amino acids tested, on an aggregate basis, is reported in FIG. 17 and Table 14c. The amino acids aggregated together for analysis were Arginine, Histidine, Isoleucine, Leucine, Threonine, Lysine, Tryptophan and Valine. This subgroup was chosen for analysis because these amino acids cannot be endogenously synthesized. As a result, their concentrations in plasma from sampling the jugular vein may be more representative of the intestinal adsorption of the tested formulations than the non-essential amino acids whose presence in blood could be independently generated by the organism.

TABLE 14c

| ESSENTIAL AA (RAW DATA) | APR-04 | APR-07 | Free amino acids | Casein |
|---|---|---|---|---|
| AUC 0-last | 1020.5 | 1029.0 | 1098.5 | 969.9 |
| $C_{max}$ | 277.0 | 292.9 | 409.0 | 299.1 |
| $T_{max}$ | 1.50 | 1.19 | 0.88 | 1.16 |
| $C_{last}$ | 170.7 | 166.2 | 138.2 | 153.0 |

The statistical analysis for the date reported in Table 14c (for AUC, $C_{max}$, and $C_{last}$: one-way repeated measures ANOVA with post hoc analysis with Bonferroni adjustment; for $T_{max}$: Friedman test followed by multiple sign test for pairwise comparison) is reported in Table 14d.

TABLE 14d

| RAW DATA | AUC | $C_{max}$ | $T_{max}$ | $C_{last}$ |
|---|---|---|---|---|
| Free AA vs APR-04 | NS | <0.01 | NS | 0.029 |
| Free AA vs APR-07 | NS | <0.01 | NS | 0.017 |

3) Mean of BCAAs Concentration (Branched Chain Amino Acids: Valine, Isoleucine and Leucine).

Figure 18:
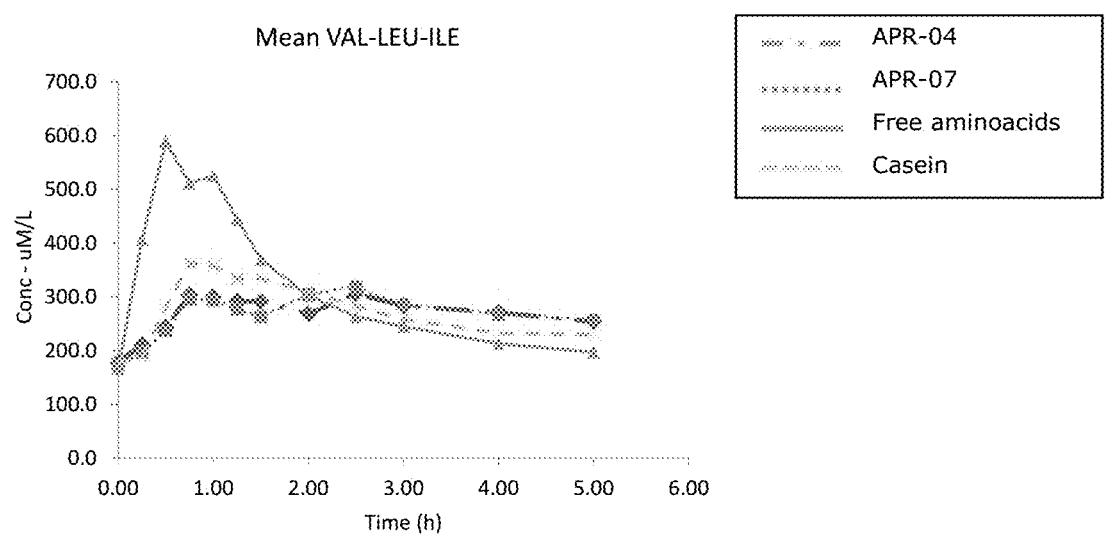
FIG. 18 reports the mean plasma concentrations in pigs of the branched chain amino acids over time, on an aggregate basis, from two separate modified release amino acid formulations of the present invention, one free amino acid formulation, and casein, as described in Example 14.

The mean plasma concentrations of the branched chain amino acids tested, on an aggregate basis, is reported in FIG. 18 and Table 14e. The amino acids aggregated together for analysis were valine, isoleucine and leucine. This subgroup of essential amino acids was chosen for analysis because these essential amino acids are unique among amino acids in that their first catabolic step cannot occur in the liver. As a consequence, they largely escape first-pass splanchnic metabolism (Brosnan et al).

TABLE 14e

| BCAA (RAW DATA) | APR-04 | APR-07 | Free amino acids | Casein |
|---|---|---|---|---|
| AUC 0-last | 1365.8 | 1367.3 | 1556.1 | 1365.3 |
| $C_{max}$ | 350.9 | 335.8 | 628.3 | 401.1 |
| $T_{max}$ | 2.41 | 1.72 | 0.63 | 1.16 |
| $C_{last}$ | 253.7 | 256.2 | 197.0 | 228.7 |

The statistical analysis for the date reported in Table 14e (for AUC, $C_{max}$, and $C_{last}$: one-way repeated measures ANOVA with post hoc analysis with Bonferroni adjustment; for $T_{max}$: Friedman test followed by multiple sign test for pairwise comparison) is reported in Table 14f.

TABLE 14f

| RAW DATA | AUC | $C_{max}$ | $T_{max}$ | $C_{last}$ |
|---|---|---|---|---|
| Free AA vs APR-04 | NS | <0.01 | <0.01 | 0.045 |
| Free AA vs APR-07 | NS | <0.01 | 0.031 | <0.01 |

4) Mean in Total LNAAs Concentration (Large Neutral Amino Acids: Phenylalanine, Tyrosine, tryptophan, threonine, methionine, valine, isoleucine, leucine, histidine).

Figure 19:
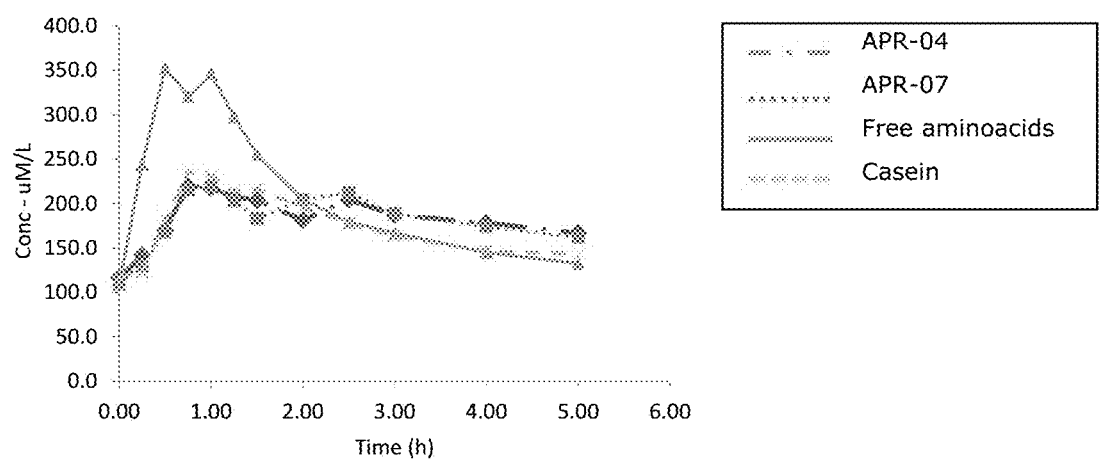
FIG. 19 reports the mean plasma concentrations in pigs of the large neutral chain amino acids over time, on an aggregate basis, from two separate modified release amino acid formulations of the present invention, one free amino acid formulation, and casein, as described in Example 14.

The plasma concentrations of the large neutral amino acids tested, on an aggregate basis, are reported in FIG. 19 and Table 14g. The amino acids aggregated together for analysis were tryptophan, threonine, valine, isoleucine, leucine, histidine. Tyrosine was excluded because of the anomalous behavior it exhibited in the dissolution and in vivo testing, and methionine because it was not stable in the samples. Phenylalanine was excluded from the analysis because it was not present in the formulations tested. This subgroup of essential amino acids was chosen for analysis because LNAA share with phenylalanine a common transport system in order to enter the brain. High plasma concentration of LNAAs may reduce the uptake into the brain (Van Spronsen et al). might thus bring clinical advantages. In particular, if the analysis on the subgroup show an increased $C_{last}$ for the APR formulations versus the free amino acid formulations, it can be speculated that the patient may have a sort of "prolonged protection/tolerance" to phenylalanine.

TABLE 14g

| LNAA (RAW DATA) | APR-04 | APR-07 | Free amino acids | Casein |
|---|---|---|---|---|
| AUC 0-last | 925.0 | 921.8 | 1028.3 | 868.9 |
| $C_{max}$ | 244.3 | 240.0 | 383.9 | 256.6 |
| $T_{max}$ | 2.16 | 1.22 | 0.69 | 1.16 |
| $C_{last}$ | 166.9 | 161.8 | 132.5 | 143.0 |

The statistical analysis for the date reported in Table 14g (for AUC, $C_{max}$, and $C_{last}$: one-way repeated measures ANOVA with post hoc analysis with Bonferroni adjustment; for $T_{max}$: Friedman test followed by multiple sign test for pairwise comparison) is reported in Table 14 h.

TABLE 14h

| RAW DATA | AUC | $C_{max}$ | $T_{max}$ | $C_{last}$ |
|---|---|---|---|---|
| Free AA vs APR-04 | NS | <0.01 | <0.01 | 0.031 |
| Free AA vs APR-07 | NS | <0.01 | NS (0.070) | <0.01 |

Throughout this application. various publications are referenced. The disclosures of these publications are hereby incorporated by reference in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only. with a true scope and spirit of the invention being indicated by the following claims.

CITED REFERENCES

AMIDON G. L. LENNERNÄS H. SHAH V. P. CRISON J. R. A theoretical basis for a biopharmaceutical drug classification: the correlation of in vitro drug product dissolution and in vivo bioavailability. Pharm. Res. 12:414-420 (1995)

BARACOS V. E. Animal models of amino acids metabolism: a focus on the intestine. J. Nutria. 134:1656S-1659S (2004)

BROSNAN J T. BROSNAN M E. Branched-chain amino acids: enzyme and substrate regulation. J Nutr. 2006 January; 136(1 Suppl):207S-11S.

CYNOBER L A. Plasma amino acid levels with a note on membrane transport: characteristics. regulation. and metabolic significance. Nutrition. 2002 September; 18(9): 761-6.

DIOGUARDI F. S. Clinical use of amino acids as dietary supplement: pros and cons. J. Cochexia Sarcopenia Muscle. 2:75-80 (2011)

EMA 2010. Guideline on the investigation of bioequivalence CPMP/EWP/QWP/1401/98 Rev. 1. London. 20 Jan. 2010

GIOVANNINI M. RIVA E. SALVATICI E. CEFALO G. RADAELLI G. Randomized controlled trial of a protein substitute with prolonged release on the protein statatus of children with phenylketonuria. J. Am. Coll. Nutr. 33. 103-110 (2014)

GROPPER S. S. ACOSTA P. B. Effect of simultaneous ingestion of L-amino acids and whole protein on plasma amino acid and urea nitrogen concentrations in humans. J. Parenteral Enteral Nutr. 15:48-53 (1991)

KEOHANE P. P. GRIMBLE G. K. BROWN B. SPILLER R. C. Influence of protein composition and hydrolysis method on intestinal absorption of protein in man. Gut. 26:907-913 (1985)

MONTGOMERY R. DRYER R. L. CONWAY T. W. SPECTOR A. A. Biochimica. Aspetti medico biologici. Translation by Berra B. Ragnotti G. Tettamanti G. Edi-Ermes. Milan. 1988
  Chapter 1: Nutrizione. pp. 1-47
  Chapter 2: Struttura delle proteine. pp. 49-121
  Chapter 10: Metabolismo degli amminoacidi. pp. 584-639.

NEY D. M. BLANK R. D. HANSEN K. E. Advances in the nutritional and pharmacological management of phenylketonuria. Co-Clinical Nutrition. Com. 17:61-68 (2014)

NEY D M. Does the PKU diet contribute to impaired renal function? J Inherit Metab Dis. 2013 September; 36(5): 903-4.

PENA M J. ROCHA J C AND BORGES N. Amino Acids. Glucose Metabolism and Clinical Relevance for Phenylketonuria Management. Ann Nutr Disord & Ther—Volume 2 Issue 3-2015

VAN SPRONSEN F J. D E GROOT M J. HOEKSMA M. REIJNGOUD D J. VAN RIJN M. Large neutral amino acids in the treatment of PKU: from theory to practice. J Inherit Metab Dis. 2010 December; 33(6):671-6.

VLIET D. VAN. DERKS T. G. J. RIJN M. VAN. DE GROOT M. J. MCDONALD A. et al. Single amino acid supplementation in aminoacidopatients: a systemic review. Orphanet J. Rare Dis. 9:1-14 (2014)

WAISBREN S. E. NOEL K. FAHRDACH K. CELLA C. FRAME D. DORENBAUM A. LEVY H. Phenylalanine blood levels and clinical outcomes in phenylketonuria: a systemic literature review and meta-analysis. Mol. Genet. Metab. 92:63-70 (2007)

Branched Chain Amino Acids in Clinical Nutrition—Volume 1. Rajendram. R; Preedy. V. R.; Patel. V. B. (Eds) 2015. XXViii. 270 p. 91 illus. in color. Hardcover WHANG K. Y. AND EASTER R. A. Asian-Aus. J. Anim. Sci. 2000 Vol. 13. No 6:811-816

The invention claimed is:

1. An orally administered amino acid formulation comprising:
   a) one or more modified release amino acids;
   b) hydroxymethylpropyl cellulose or ethylcellulose or a combination thereof integrally mixed with said amino acids; or
   c) a coating on said modified release amino acids comprising ethylcellulose or a combination of ethylcellulose and glyceryl dibehenate;
   wherein the formulation comprising 2 g of the modified release amino acids comprises a release profile releasing no more than 70% of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, and said modified release is defined by said release profile.

2. The formulation of claim 1, comprising five or more of the following amino acids as modified release amino acids in the recited weight parts:

| Amino Acid | Weight Parts |
| --- | --- |
| L-Alanine | 2.0-12.0 |
| L-Arginine | 3.0-10.5 |
| L-Aspartic Acid | 5.0-10.5 |
| L-Cystine | 1.5-4.0 |
| L-Glutamic Acid + Glutamine | 7.0-25.0 |
| Glycine | 3.5-15.0 |
| L-Histidine | 2.0-6.5 |
| L-Isoleucine | 2.0-8.5 |
| L-Leucine | 8.0-15.0 |
| L-Lysine | 4.5-10.5 |
| L-Methionine | 1.0-3.0 |
| L-Phenylalanine | 4.0-7.5 |
| L-Proline | 3.5-15.0 |
| L-Serine | 2.0-8.5 |
| L-Threonine | 4.0-7.5 |
| L-Tryptophan | 1.0-4.0 |
| L-Tyrosine | 2.5-14.0 |
| L-Valine | 2.5-10.0 |
| L-Carnitine | 0.0-0.2 |
| Taurine | 0.05-1.0. |

3. The formulation of claim 2, comprising ten or more of the recited amino acids as modified release amino acids in the recited weight parts.

4. The formulation of claim 2, comprising fifteen or more of the recited amino acids as modified release amino acids in the recited weight parts.

5. The formulation of claim 2, comprising the recited essential amino acids, branched chain amino acids, and large neutral amino acids as modified release amino acids in the recited weight parts.

6. The formulation of claim 1, comprising five or more of the following amino acids as modified release amino acids in the recited weight parts:

| Amino Acid | Weight Parts |
| --- | --- |
| L-Alamine | 2.0-12.0 |
| L-Arginine | 3.0-10.5 |
| L-Aspartic Acid | 5.0-10.5 |
| L-Cystine | 1.5-4.0 |
| L-Glutamic Acid + Glutamine | 7.0-25.0 |
| Glycine | 3.5-15.0 |
| L-Histidine | 2.0-6.5 |
| L-Isoleucine | 2.0-8.5 |
| L-Leucine | 8.0-15.0 |
| L-Lysine | 4.5-10.5 |
| L-Methionine | 1.0-3.0 |
| L-Phenylalanine | 4.0-7.5 |
| L-Proline | 3.5-15.0 |
| L-Serine | 2.0-8.5 |
| L-Threonine | 4.0-7.5 |
| L-Tryptophan | 1.0-4.0 |
| L-Tyrosine | 2.5-14.0 |

| Amino Acid | Weight Parts |
| --- | --- |
| L-Valine | 2.5-10.0 |
| L-Carnitine | 0.0-0.2 |
| Taurine | 0.05-1.0 | comprising 0.0 weight parts L-phenylalanine.

7. The formulation of claim 1, comprising five or more of the following amino acids as modified release amino acids in the recited weight parts

| Amino Acid | Weight Parts |
| --- | --- |
| L-Alamine | 2.0-12.0 |
| L-Arginine | 3.0-10.5 |
| L-Aspartic Acid | 5.0-10.5 |
| L-Cystine | 1.5-4.0 |
| L-Glutamic Acid + Glutamine | 7.0-25.0 |
| Glycine | 3.5-15.0 |
| L-Histidine | 2.0-6.5 |
| L-Isoleucine | 2.0-8.5 |
| L-Leucine | 8.0-15.0 |
| L-Lysine | 4.5-10.5 |
| L-Methionine | 1.0-3.0 |
| L-Phenylalanine | 4.0-7.5 |
| L-Proline | 3.5-15.0 |
| L-Serine | 2.0-8.5 |
| L-Threonine | 4.0-7.5 |
| L-Tryptophan | 1.0-4.0 |
| L-Tyrosine | 2.5-14.0 |
| L-Valine | 2.5-10.0 |
| L-Carnitine | 0.0-0.2 |
| Taurine | 0.05-1.0 | comprising 0.0 weight parts L-phenylalanine and 0.0 weight parts L-tyrosine.

8. The formulation of claim 1 wherein the formulation is a powder or granulate.

9. The formulation of claim 1 in the form of a tablet, a pill, a soft or hard gelatin capsule, a powder, a granulate, a microsphere, a lozenge, a sachet of packaged powders or granulates or microspheres, an elixir, a suspension, an emulsion, a chewable tablet, or a syrup.

10. The formulation of claim 1, wherein the formulation further comprises one or more additional ingredients selected from the group consisting of:
   a) vitamins, minerals and carbohydrates; or
   b) choline, inositol, vitamin A, vitamin D, vitamin E, vitamin K, vitamin C, thiamin, riboflavin, niacin, vitamin B6, folate, vitamin B12, biotin, pantothenic acid, potassium, calcium, magnesium, iron, zinc, copper, manganese, selenium, chromium, molybdenum, iodine, sodium, sulfur, phosphorus, docosahexaenoic acid, eicosapentaenoic acid, arachidonic acid, and lutein, and salts, chelates, and esters thereof.

11. The formulation of claim 1 wherein the formulation comprising 2 g of the modified release amino acids comprises a release profile releasing no more than 60% of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, and said modified release is defined by said release profile.

12. An orally administered amino acid formulation comprising one or more modified release amino acids wherein the formulation comprising 2 g of the modified release amino acids comprises a release rate releasing no more than 70% of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein said modified release is defined by said release profile, wherein the modified release amino acids are granulates coated by from 5 wt % to 25 wt % of one or more release modifying excipients based on the weight of the amino acids, wherein each of the granulates comprise a plurality of modified release amino acids, and wherein said formulation comprises:
   a) hydroxymethylpropyl cellulose or ethylcellulose or a combination thereof integrally mixed with said amino acids; or
   b) a coating on said modified release amino acids comprising ethylcellulose or a combination of ethylcellulose and glyceryl dibehenate.

13. The formulation of claim 12 further comprising one or more release modifying excipients selected from ethylcellulose and a combination of ethylcellulose and glyceryl dibehenate.

14. The formulation of claim 12 further comprising:
   a) a bulking agent selected from lactose, sucrose, dextrose, sorbitol, fructose, and cellulose powder;
   b) a disintegrating agent selected from microcrystalline cellulose, starches, crospovidone, sodium starch glycolate, and crosscarmellose sodium;
   c) a glidant or lubricant selected from talc, corn starch, silicon dioxide, sodium lauryl sulfate, magnesium stearate, calcium stearate, sodium stearate, stearic acid, sodium stearyl fumarate, hydrogenated cotton seed oil, talc, waxes, cetyl alcohol, glyceryl stearate, glyceryl palmitate, glyceryl behenate, hydrogenated vegetable oils, and stearyl alcohol;
   d) a taste-masking agent selected from cellulose hydroxypropyl ethers (HPC); low-substituted hydroxypropyl ethers (L-HPC); cellulose hydroxypropyl methyl ethers (HPMC); methylcellulose polymers; Ethylcelluloses (EC) and mixtures thereof; Polyvinyl alcohol (PVA); hydroxyethylcelluloses; carboxymethylcelluloses and salts of carboxymethylcelluloses (CMC); polyvinyl alcohol and polyethylene glycol co-polymers; monoglycerides, triglycerides, polyethylene glycols, modified food starch, acrylic polymers and mixtures of acrylic polymers with cellulose ethers; cellulose acetate phthalate; sepifilms such as mixtures of HPMC and stearic acid, cyclodextrins, and mixtures thereof;
   e) a flavoring agent selected from acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, raspberry, root beer, rum, saccharin, safrole, sorbitol, spearmint, spearmint cream, strawberry, strawberry cream, *stevia*, sucralose, sucrose, sodium saccharin, saccharin, aspartame, neotame, acesulfame potassium, mannitol, talin, xylitol, sucralose, sorbitol, swiss cream, tagatose, tangerine, thaumatin, tutti fruitti, vanilla, walnut, watermelon, wild cherry, wintergreen, xylitol, or a combination thereof;

f) one or more release modifying excipients selected from the group consisting of ethylcellulose, glyceryl dibehenate, cellulose acetate, vinyl acetate/vinyl chloride copolymers, acrylate/methacrylate copolymers, polyethylene oxide, hydroxypropyl methylcellulose, carrageenan, alginic acid and salts thereof, hydroxyethyl cellulose, hydroxypropyl cellulose, karaya gum, acacia gum, tragacanth gum, locust bean gum, guar gum, sodium carboxymethyl cellulose, methyl cellulose, beeswax, carnauba wax, cetyl alcohol, hydrogenated vegetable oils, stearyl alcohol, acrylic acid copolymers, sodium alginate, carrageenan, alginic acid, pectin, sodium carboxymethyl cellulose, a starch derivative, or a combination thereof; or g) a binder selected from polyvinyl pyrrollidone, starch, methylcellulose, hydroxypropyl methylcellulose, carboxymethyl cellulose, sucrose solution, dextrose solution, guar gum, xanthan gum, acacia, tragacanth, locust bean gum and sodium alginate, or an alginic acid salt.

15. The formulation of claim 12 further comprising a binder selected from sodium alginate or an alginic acid salt.

16. The formulation of claim 1, wherein tyrosine in the formulation is not coated by a modified release coating.

17. A method of making a formulation of claim 12 comprising:
   a) providing a first mixture comprising a plurality of amino acids;
   b) contacting the mixture with a wetting agent and a binder to form a wet mixture;
   c) optionally passing the wet mixture through a sieve to form a uniform wet granulate;
   d) drying the uniform wet granulate to form a dry granulate;
   e) optionally passing the dry granulate through a sieve to form a uniform dry granulate; and
   f) coating the uniform dry granulate with a modified release composition.

18. An orally administered amino acid formulation comprising one or more modified release amino acids wherein the formulation comprising 2 g of the modified release amino acids comprises a release profile releasing no more than 70% of the modified release amino acids in 30 minutes of dissolution testing performed in a <711> USP 39 NF 34, paddle apparatus, at 37° C., in 450 or 500 mL, 0.1 N hydrochloric acid (pH 1.2), paddle speed 50 rpm, wherein said modified release is defined by said release profile, wherein the modified release amino acids are granulates coated by from 5 wt % to 25 wt % of one or more release modifying excipients based on the weight of the amino acids, and wherein each of the granulates comprise a plurality of modified release amino acids, further comprising one or more release modifying excipients selected from ethylcellulose and a combination of ethylcellulose and glyceryl dibehenate.

19. The formulation of claim 18 further comprising a binder selected from sodium alginate or an alginic acid salt.

20. The formulation of claim 18, wherein tyrosine in the formulation is not coated by a modified release coating.

21. The formulation of claim 18 comprising granulates having a size ranging from 0.1 to 1.5 mm.

* * * * *